(12) United States Patent
Chen et al.

(10) Patent No.: US 12,325,703 B2
(45) Date of Patent: Jun. 10, 2025

(54) FUSED RING COMPOUND AS FGFR AND VEGFR DUAL INHIBITOR

(71) Applicant: CGENETECH (SUZHOU, CHINA) CO., LTD., Jiangsu (CN)

(72) Inventors: Zhengxia Chen, Shanghai (CN); Haizhong Tan, Shanghai (CN); Yang Zhang, Shanghai (CN); Jian Li, Shanghai (CN); Shuhui Chen, Shanghai (CN)

(73) Assignee: CGeneTech (Suzhou, China) CO., Ltd., Jiangsu (CN)

( * ) Notice: Subject to any disclaimer, the term of this patent is extended or adjusted under 35 U.S.C. 154(b) by 753 days.

(21) Appl. No.: 17/596,531

(22) PCT Filed: Jun. 12, 2020

(86) PCT No.: PCT/CN2020/095864
§ 371 (c)(1),
(2) Date: Dec. 13, 2021

(87) PCT Pub. No.: WO2020/249096
PCT Pub. Date: Dec. 17, 2020

(65) Prior Publication Data
US 2022/0315581 A1 Oct. 6, 2022

(30) Foreign Application Priority Data

| Jun. 14, 2019 | (CN) | 201910516134.1 |
| Oct. 30, 2019 | (CN) | 201911044514.6 |
| Jan. 13, 2020 | (CN) | 202010033842.2 |

(51) Int. Cl.
  *C07D 471/04* (2006.01)
  *A61P 35/00* (2006.01)
  *C07D 487/04* (2006.01)

(52) U.S. Cl.
  CPC ........... *C07D 471/04* (2013.01); *A61P 35/00* (2018.01); *C07D 487/04* (2013.01)

(58) Field of Classification Search
  CPC ..... C07D 471/04; C07D 487/04; A61P 35/00; A61K 31/437; A61K 31/519; A61K 31/5377
  See application file for complete search history.

(56) References Cited

U.S. PATENT DOCUMENTS

| 7,074,801 B1 | 7/2006 | Yoshida et al. |
| 2004/0220189 A1 | 11/2004 | Sun et al. |
| 2008/0009497 A1 | 1/2008 | Wittman et al. |

FOREIGN PATENT DOCUMENTS

| CN | 101679408 A | 3/2010 | |
| CN | 106046007 A | 10/2016 | |
| EP | 2114941 B1 | 3/2015 | |
| JP | 2002501532 A | 1/2002 | |
| JP | 2002539126 A | 11/2002 | |
| JP | 2010513447 A | 4/2010 | |
| JP | 2010513448 A | 4/2010 | |
| JP | 2014528469 A | 10/2014 | |
| JP | 2016515604 A | 5/2016 | |
| JP | 2018531218 A | 10/2018 | |
| WO | WO-9854093 A1 | 12/1998 | |
| WO | WO-0053605 A1 | 9/2000 | |
| WO | WO-2002088107 A1 | 11/2002 | |
| WO | WO-2008078091 A1 * | 7/2008 | ........... A61K 31/437 |
| WO | WO-2013053983 A1 | 4/2013 | |
| WO | WO-2017024968 A1 | 2/2017 | |
| WO | WO-2020135878 A1 * | 7/2020 | |

OTHER PUBLICATIONS

Feb. 12, 2024 Office Action issued in Korea Application No. 10-2022-7001095.
Jun. 20, 2023 European Extended Search Report issued in European Application No. 20823692.
Nov. 3, 2003 Johns B A et al, "Pyrazolo[1,5-a]pyridines: synthetic approaches to a novel class of antiherpetics", Tetrahedron, Nov. 3, 2003, pp. 9001-9011, vol. 59, No. 45, Elsevier Science Publishers, Amsterdam, NL.
Feb. 14, 2023 First Office Action issued in Japanese Patent Application No. 2021-574346.
Jan. 9, 2023 First Office Action issued in Canadian Patent Application No. 3141424.
Jan. 12, 2023 First Office Action issued in Australian Patent Application No. 2020292664.
Sep. 17, 2020 International Search Report issued in International Patent Application No. PCT/CN2020/095864.
Sep. 17, 2020 Written Opinion of the International Searching Authority issued in International Patent Application No. PCT/CN2020/095864.

(Continued)

*Primary Examiner* — John S Kenyon
*Assistant Examiner* — Sara Elizabeth Bell
(74) *Attorney, Agent, or Firm* — Harness, Dickey & Pierce, P.L.C.

(57) ABSTRACT

A fused ring compound as an FGFR and VEGFR dual inhibitor. Particularly, disclosed is a compound represented by formula (III) or a pharmaceutically acceptable salt thereof.

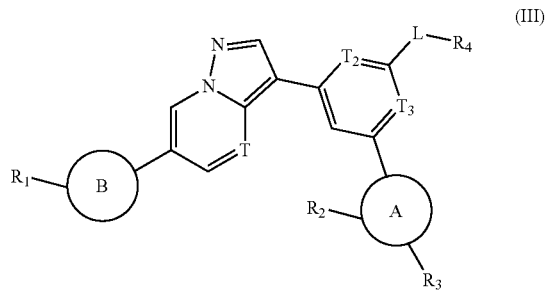

17 Claims, 1 Drawing Sheet

(56) References Cited

OTHER PUBLICATIONS

Mar. 27, 2023 Chinese Search Report issued in Chinese Patent Application No. 2020800435435.
Mar. 27, 2023 Chinese Office Action issued in Chinese Patent Application No. 2020800435435.

\* cited by examiner

FUSED RING COMPOUND AS FGFR AND VEGFR DUAL INHIBITOR

CROSS-REFERENCE TO RELATED APPLICATIONS

This application is a U.S. National Phase Application under 35 U.S.C. 371 of International Application No. PCT/CN2020/095864, filed on Jun. 12, 2020, which claims the benefit of Chinese Patent Application No. 201910516134.1, filed on Jun. 14, 2019, Chinese Patent Application No. 201911044514.6, filed on Oct. 30, 2019, and Chinese Patent Application No. 202010033842.2, filed on Jan. 13, 2020. The entire disclosures of the above applications are incorporated herein by reference.

TECHNICAL FIELD

The present disclosure relates to a fused ring compound as an FGFR and VEGFR dual inhibitor, and particularly relates to a compound represented by formula (III) or a pharmaceutically acceptable salt thereof.

BACKGROUND

FGFRs are a class of biologically active substances that have the functions of transmitting biological signals, regulating cell growth, and participating in tissue repair. In recent years, many members of the FGFR family have been found to play an important role in the occurrence and development of tumors. Fibroblast growth factor receptors (FGFRs) are a class of receptor proteins that specifically bind to fibroblast growth factors (FGFs), which FGFR family includes the following types: FGFR1b, FGFR1c, FGFR2b, FGFR2c, FGFR3b, FGFR3c and FGFR4. Different subtypes of FGFRs bind to different FGFs. The binding of FGFs and FGFRs leads to autophosphorylation of multiple tyrosine residues in the cell. Phosphorylated FGFRs activate downstream signal pathways including MEK/MAPK, PLCy/PKC, PI3K/AKT, STATS, etc. In tumors, such as liver cancer, bladder cancer, lung cancer, breast cancer, endometrial cancer, brain glioma, and prostate cancer, FGFR-activated mutation or ligand/receptor overexpression leads to continuous constitutive activation of FGFRs, which is not only closely related to tumor occurrence, development, and poor prognosis, but also plays an important role in tumor angiogenesis, tumor invasion and metastasis, etc. Therefore, FGFRs are considered to be important anti-tumor targets.

Angiogenesis and lymphangiogenesis are important links in tumor formation and metastasis. Vascular endothelial growth factor (VEGF) and VEGF receptor (VEGFR) families play a major role in these two links. The VEGFR family includes three specific tyrosine kinase receptors: VEGFR-1, VEGFR-2 (KDR) and VEGFR-3. VEGFR-2 is an important regulator of VEGF signaling that causes endothelial cell proliferation, increases vascular permeability and promotes angiogenesis, and has a greater affinity for VEGF than VEGFR-1. Studies have shown that only VEGFR-2 is expressed in endothelial cells, and activating VEGFR-2 can effectively stimulate angiogenesis. Therefore, VEGFR-2 is the main target for the development of anti-angiogenesis drugs.

Under specific experimental conditions, VEGFs can only play its role in promoting angiogenesis in the presence of FGFs, and VEGFR and FGFR pathways work together to activate and generate endothelial cells in angiogenesis. FGFRs and VEGFRs can directly inhibit the growth, survival, proliferation and migration of tumor cells; and can also inhibit tumor angiogenesis and improve the microenvironment. Moreover, the FGFR and VEGFR pathways act synergistically to inhibit tumor immune escape and improve tumor suppression effect.

CONTENT OF THE PRESENT INVENTION

The present disclosure provides a compound represented by formula (III) or a pharmaceutically acceptable salt thereof,

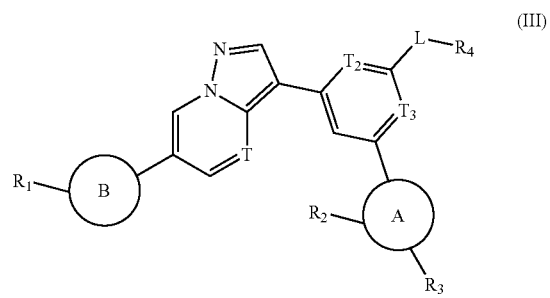

(III)

wherein,

T, $T_2$ and $T_3$ are each independently selected from N and CH;

$R_1$ is selected from H, $C_{1-3}$ alkyl, tetrahydropyranyl, piperidinyl,

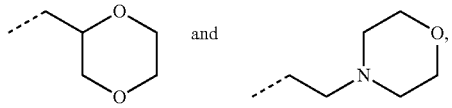

and the $C_{1-3}$ alkyl, tetrahydropyranyl, piperidinyl,

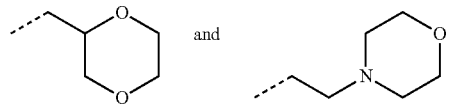

are optionally substituted with 1, 2 or 3 $R_a$; wherein,

⫽ is used to denote a point of attachment;

$R_2$ and $R_3$ are each independently selected from H, F, Cl, Br, I, OH and $NH_2$;

$R_4$ is selected from H, $C_{1-3}$ alkyl, $C_{1-3}$ alkoxy, $C_{3-5}$ cycloalkyl and pyrrolidinyl, and the $C_{1-3}$ alkyl, $C_{1-3}$ alkoxy, $C_{3-5}$ cycloalkyl and pyrrolidinyl are optionally substituted with 1, 2 or 3 $R_b$;

L is selected from $-N(R_5)C(=O)-$, $-N(R_5)S(=O)_2-$, $-N(R_5)C(=O)N(R_6)-$ and $-NR_5-$;

$R_5$ and $R_6$ are each independently selected from H and $C_{1-3}$ alkyl;

ring A is selected from phenyl and pyridyl;

ring B is selected from cyclopropyl, morpholinyl, piperazinyl, tetrahydropyranyl, pyrazolyl, imidazolyl and triazolyl;

$R_a$ and $R_b$ are each independently selected from H, F, Cl, Br, I, OH, $NH_2$, CN, $CH_3$, $N(CH_3)_2$ and $-S(=O)_2CH_3$.

The present disclosure provides a compound represented by formula (III) or a pharmaceutically acceptable salt thereof,

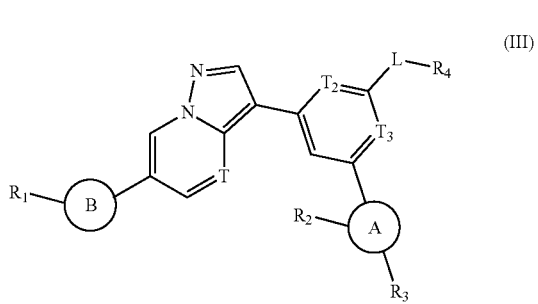

wherein,

T, $T_2$ and $T_3$ are each independently selected from N and CH;

$R_1$ is selected from H, $C_{1-3}$ alkyl, tetrahydropyranyl, piperidinyl,

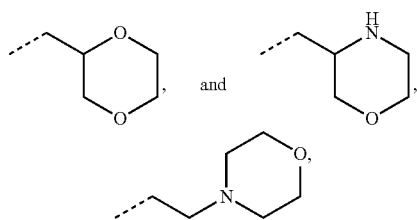

and the $C_{1-3}$ alkyl, tetrahydropyranyl, piperidinyl,

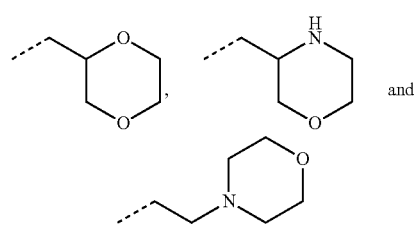

are optionally substituted with 1, 2 or 3 $R_a$; wherein,

⌁ is used to denote a point of attachment;

$R_2$ and $R_3$ are each independently selected from H, F, Cl, Br, I, OH and $NH_2$;

$R_4$ is selected from H, $C_{1-3}$ alkyl, $C_{1-3}$ alkoxy, $C_{3-5}$ cycloalkyl, —$CH_2$-1,3-dioxolanyl and pyrrolidinyl, and the $C_{1-3}$ alkyl, $C_{1-3}$ alkoxy, $C_{3-5}$ cycloalkyl, —$CH_2$-1,3-dioxolanyl and pyrrolidinyl are optionally substituted with 1, 2 or 3 $R_b$;

L is selected from —N($R_5$)C(=O)—, —N($R_5$)S(=O)$_2$—, —N($R_5$)C(=O)N($R_6$)— and —$NR_5$—;

$R_5$ and $R_6$ are each independently selected from H and $C_{1-3}$ alkyl;

ring A is selected from phenyl and pyridyl;

ring B is selected from cyclopropyl, morpholinyl, piperazinyl, tetrahydropyranyl, pyrazolyl, imidazolyl and triazolyl;

$R_a$ and $R_b$ are each independently selected from H, F, Cl, Br, I, OH, $NH_2$, CN, $CH_3$, $N(CH_3)_2$, —S(=O)$_2CH_3$ and benzyl.

The present disclosure provides a compound represented by formula (III) or a pharmaceutically acceptable salt thereof,

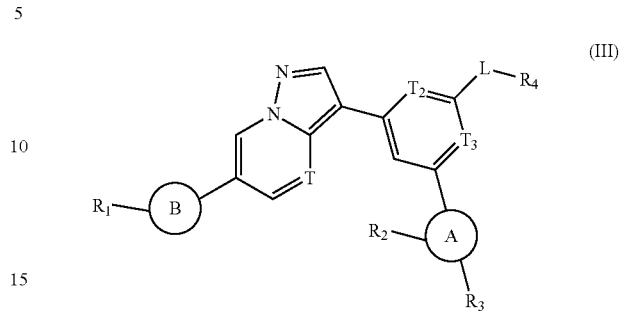

wherein,

T, $T_2$ and $T_3$ are each independently selected from N and CH;

$R_1$ is selected from H, $C_{1-3}$ alkyl, tetrahydropyranyl, piperidinyl,

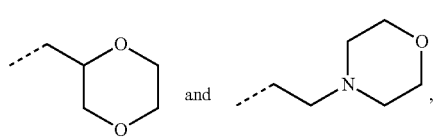

and the $C_{1-3}$ alkyl, tetrahydropyranyl, piperidinyl,

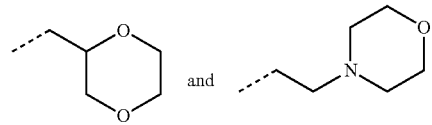

are optionally substituted with 1, 2 or 3 $R_a$;

$R_2$ and $R_3$ are each independently selected from H, F, Cl, Br, I, OH and $NH_2$;

$R_4$ is selected from H, $C_{1-3}$ alkyl, $C_{1-3}$ alkoxy, $C_{3-5}$ cycloalkyl and pyrrolidinyl, and the $C_{1-3}$ alkyl, $C_{1-3}$ alkoxy, $C_{3-5}$ cycloalkyl and pyrrolidinyl are optionally substituted with 1, 2 or 3 $R_b$;

L is selected from —N($R_5$)C(=O)—, —N($R_5$)S(=O)$_2$—, —N($R_5$)C(=O)N($R_6$)— and —$NR_5$—;

$R_5$ and $R_6$ are each independently selected from H and $C_{1-3}$ alkyl;

ring A is selected from phenyl and pyridyl;

ring B is selected from cyclopropyl, morpholinyl, piperazinyl, tetrahydropyranyl, pyrazolyl, imidazolyl and triazolyl;

$R_a$ and $R_b$ are each independently selected from H, F, Cl, Br, I, OH, $NH_2$, CN, $CH_3$, $N(CH_3)_2$ and —S(=O)$_2CH_3$.

The present disclosure provides a compound represented by formula (III) or a pharmaceutically acceptable salt thereof,

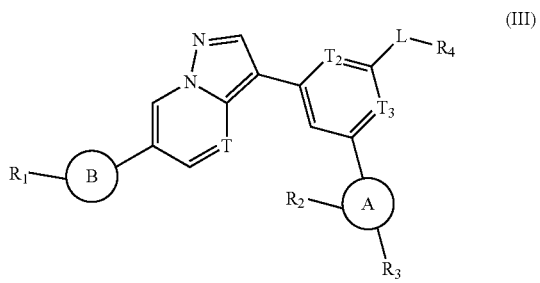

(III)

wherein,

T, T$_2$ and T$_3$ are each independently selected from N and CH;

R$_1$ is selected from H, C$_{1-3}$ alkyl, tetrahydropyranyl, piperidinyl,

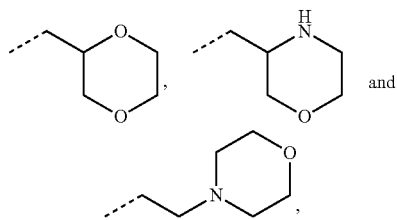
and

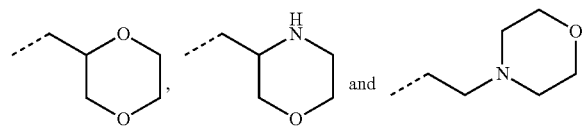

and the C$_{1-3}$ alkyl, tetrahydropyranyl, piperidinyl, are optionally substituted with 1, 2 or 3 R$_a$;

R$_2$ and R$_3$ are each independently selected from H, F, Cl, Br, I, OH and NH$_2$;

R$_4$ is selected from H, C$_{1-3}$ alkyl, C$_{1-3}$ alkoxy, C$_{3-5}$ cycloalkyl, —CH$_2$-1,3-dioxolanyl and pyrrolidinyl, and the C$_{1-3}$ alkyl, C$_{1-3}$ alkoxy, C$_{3-5}$ cycloalkyl, —CH$_2$-1,3-dioxolanyl and pyrrolidinyl are optionally substituted with 1, 2 or 3 R$_b$;

L is selected from —N(R$_5$)C(=O)—, —N(R$_5$)S(=O)$_2$—, —N(R$_5$)C(=O)N(R$_6$)— and —NR$_5$—;

R$_5$ and R$_6$ are each independently selected from H and C$_{1-3}$ alkyl;

ring A is selected from phenyl and pyridyl;

ring B is selected from cyclopropyl, morpholinyl, piperazinyl, tetrahydropyranyl, pyrazolyl, imidazolyl and triazolyl;

R$_a$ and R$_b$ are each independently selected from H, F, Cl, Br, I, OH, NH$_2$, CN, CH$_3$, N(CH$_3$)$_2$, —S(=O)$_2$CH$_3$ and benzyl.

In some embodiments of the present disclosure, the above-mentioned R$_1$ is selected from H, CH$_3$, CH$_2$CH$_3$ and CH$_2$CH$_2$CH$_3$, wherein the CH$_3$, CH$_2$CH$_3$ and CH$_2$CH$_2$CH$_3$ are optionally substituted with 1, 2 or 3 R$_a$, and other variables are as defined in the present disclosure.

In some embodiments of the present disclosure, the above-mentioned R$_1$ is selected from H, CH$_3$, CH$_2$CH$_3$, CH$_2$CH$_2$CH$_3$, tetrahydropyranyl, piperidinyl and

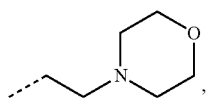, wherein the CH$_3$, CH$_2$CH$_3$, CH$_2$CH$_2$CH$_3$, tetrahydropyranyl, piperidinyl and

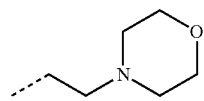

are optionally substituted with 1, 2 or 3 R$_a$, and other variables are as defined in the present disclosure.

In some embodiments of the present disclosure, the above-mentioned R$_1$ is selected from H, CH$_3$, CH$_2$CH$_3$, CH$_2$CH$_2$CH$_3$,

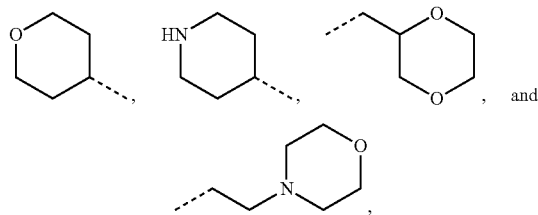

wherein the CH$_3$, CH$_2$CH$_3$, CH$_2$CH$_2$CH$_3$,

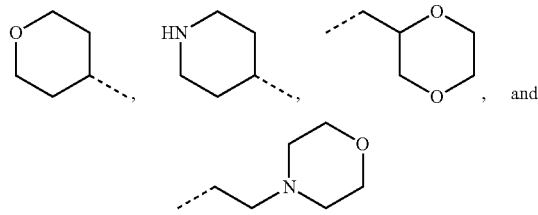

are optionally substituted with 1, 2 or 3 R$_a$, and other variables are as defined in the present disclosure.

In some embodiments of the present disclosure, the above-mentioned R$_1$ is selected from H, CH$_3$, CH$_2$CH$_3$, CH$_2$CH$_2$CH$_3$,

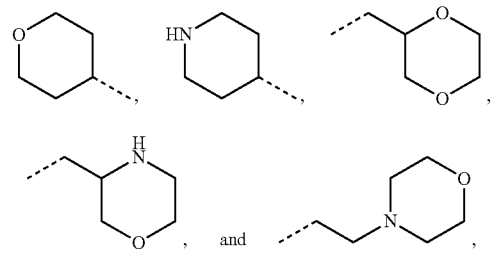

wherein the $CH_3$, $CH_2CH_3$, $CH_2CH_2CH_3$,

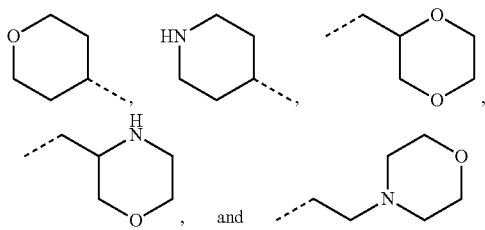

are optionally substituted with 1, 2 or 3 $R_a$, and other variables are as defined in the present disclosure.

In some embodiments of the present disclosure, the above-mentioned $R_1$ is selected from H, $CH_3$, $CH_2CH_3$ and

and other variables are as defined in the present disclosure.

In some embodiments of the present disclosure, the above-mentioned $R_1$ is selected from H, $CH_3$, $CH_2CH_3$,

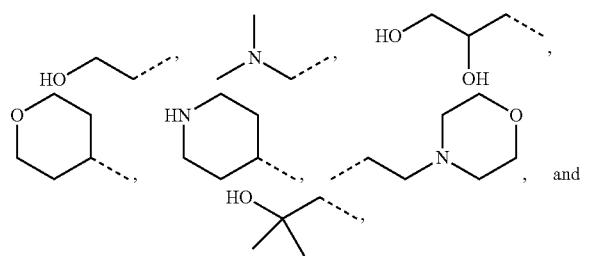

and other variables are as defined in the present disclosure.

In some embodiments of the present disclosure, the above-mentioned $R_1$ is selected from H, $CH_3$, $CH_2CH_3$,

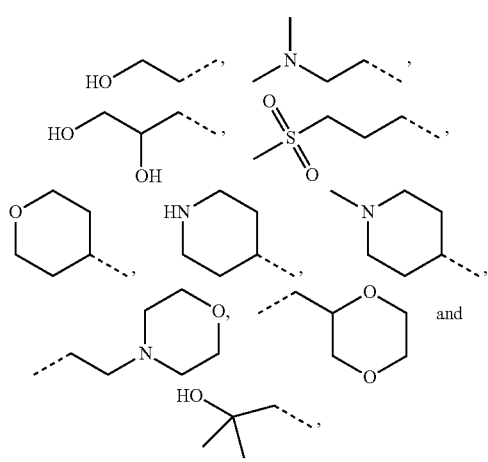

and other variables are as defined in the present disclosure.

In some embodiments of the present disclosure, the above-mentioned $R_4$ is selected from H, cyclopropanyl, $CH_3$, $CH_2CH_3$, $CH(CH_3)_2$, $OCH_3$ and pyrrolidinyl, wherein the cyclopropanyl, $CH_3$, $CH_2CH_3$, $CH(CH_3)_2$, $OCH_3$ and pyrrolidinyl are optionally substituted with 1, 2 or 3 $R_b$, and other variables are as defined in the present disclosure.

In some embodiments of the present disclosure, the above-mentioned $R_4$ is selected from H, cyclopropanyl, $CH_3$, $CH_2CH_3$, $CH(CH_3)_2$, $CH_2CH_2CH_3$, $OCH_3$, —$CH_2$-1, 3-dioxolanyl and pyrrolidinyl, wherein the cyclopropanyl, $CH_3$, $CH_2CH_3$, $CH(CH_3)_2$, $CH_2CH_2CH_3$, $OCH_3$, —$CH_2$-1, 3-dioxolanyl and pyrrolidinyl are optionally substituted with 1, 2 or 3 $R_b$, and other variables are as defined in the present disclosure.

In some embodiments of the present disclosure, the above-mentioned $R_4$ is selected from H, cyclopropanyl, $CH_3$, $CH_2CH_3$, $C(CH_3)_2$, $OCH_3$ and pyrrolidinyl, wherein the cyclopropanyl, $CH_3$, $CH_2CH_3$, $C(CH_3)_2$, $OCH_3$ and pyrrolidinyl are optionally substituted with 1, 2 or 3 $R_b$, and other variables are as defined in the present disclosure.

In some embodiments of the present disclosure, the above-mentioned $R_4$ is selected from H,

$CH_3$, $CH_2CH_3$, $CH(CH_3)_2$, $OCH_3$ and

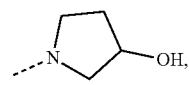

and other variables are as defined in the present disclosure.

In some embodiments of the present disclosure, the above-mentioned $R_4$ is selected from H,

$CH_3$, $CH_2CH_3$, $CH(CH_3)_2$, $OCH_3$,

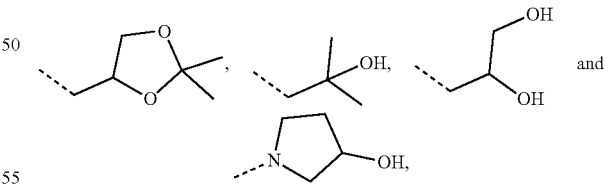

and other variables are as defined in the present disclosure.

In some embodiments of the present disclosure, the above-mentioned $R_4$ is selected from H,

CH₃, CH₂CH₃, C(CH₃)₂, OCH₃ and

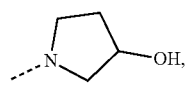

and other variables are as defined in the present disclosure.

In some embodiments of the present disclosure, the above-mentioned R₄ is selected from H,

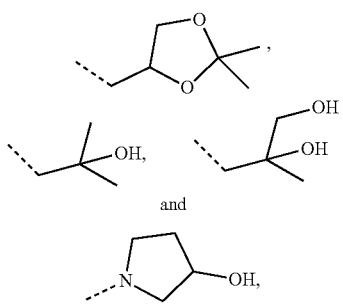

CH₃, CH₂CH₃, C(CH₃)₂, OCH₃, and other variables are as defined in the present disclosure.

In some embodiments of the present disclosure, the above-mentioned R₅ is independently selected from H, CH₃ and CH₂CH₃, and other variables are as defined in the present disclosure.

In some embodiments of the present disclosure, the above-mentioned R₅ and R₆ are each independently selected from H, CH₃ and CH₂CH₃, and other variables are as defined in the present disclosure.

In some embodiments of the present disclosure, the above-mentioned L is selected from —NHC(=O)—, —NHS(=O)₂— and —NH—, and other variables are as defined in the present disclosure.

In some embodiments of the present disclosure, the above-mentioned L is selected from —NHC(=O)—, —NHS(=O)₂—, —NHC(=O)NH— and —NH—, and other variables are as defined in the present disclosure.

In some embodiments of the present disclosure, the above-mentioned -L-R₄ is selected from

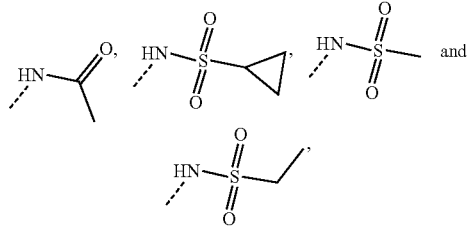

and other variables are as defined in the present disclosure.

In some embodiments of the present disclosure, the above-mentioned -L-R₄ is selected from

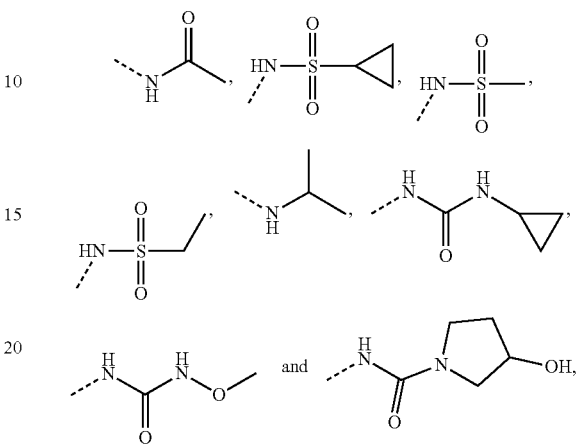

and other variables are as defined in the present disclosure.

In some embodiments of the present disclosure, the above-mentioned -L-R₄ is selected from

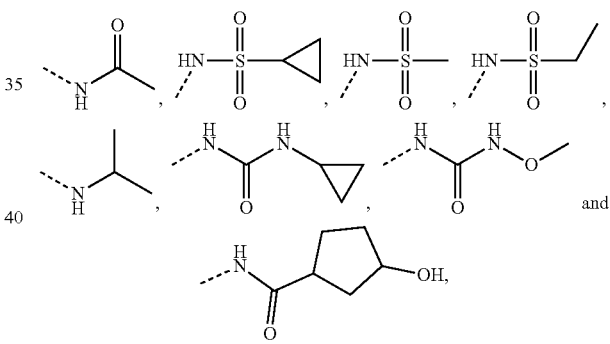

and other variables are as defined in the present disclosure.

In some embodiments of the present disclosure, the above-mentioned -L-R₄ is selected from

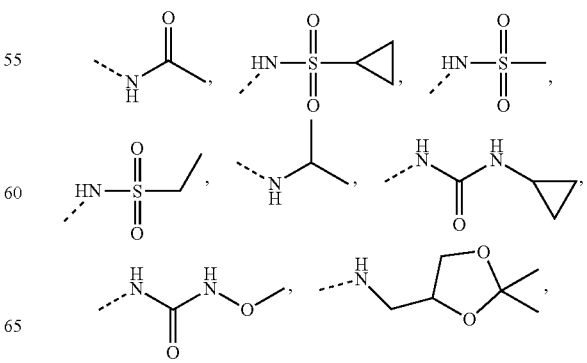

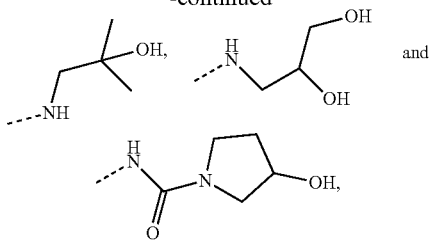

and and other variables are as defined in the present disclosure.

In some embodiments of the present disclosure, the above-mentioned ring A is selected from phenyl and pyridyl, and other variables are as defined in the present disclosure.

In some embodiments of the present disclosure, the above-mentioned structural unit

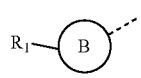

is selected from

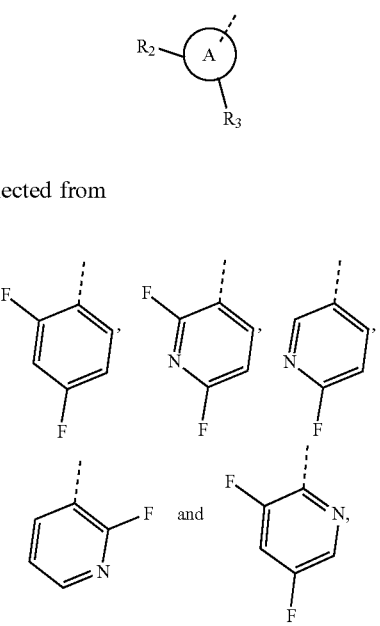

and and other variables are as defined in the present disclosure.

In some embodiments of the present disclosure, the above-mentioned ring B is selected from morpholinyl, piperazinyl, tetrahydropyranyl or pyrazolyl, and other variables are as defined in the present disclosure.

In some embodiments of the present disclosure, the above-mentioned ring B is selected from morpholinyl, piperazinyl, tetrahydropyranyl, pyrazolyl, imidazolyl and triazolyl, and other variables are as defined in the present disclosure.

In some embodiments of the present disclosure, the above-mentioned ring B is selected from

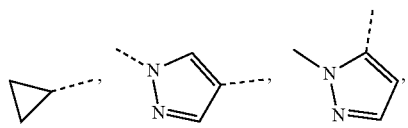

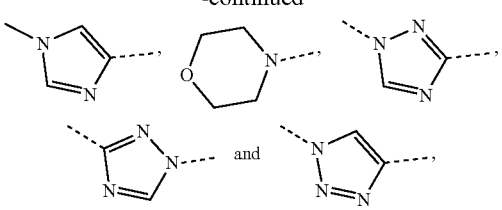

and other variables are as defined in the present disclosure.

In some embodiments of the present disclosure, the above-mentioned structural unit

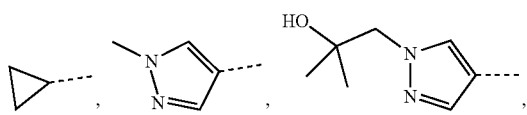

is selected from

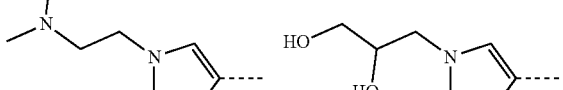

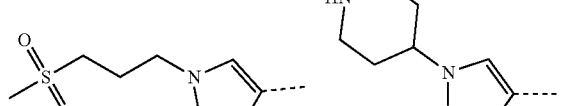

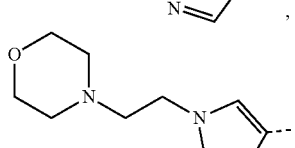

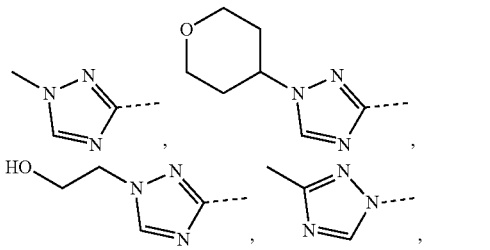

-continued

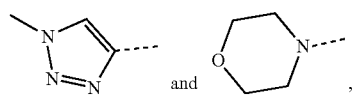 and , and other variables are as defined in the present disclosure.

In some embodiments of the present disclosure, the above-mentioned structural unit

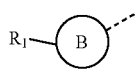

is selected from

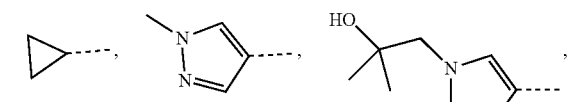
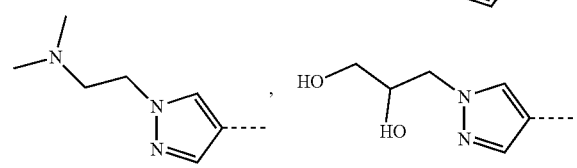
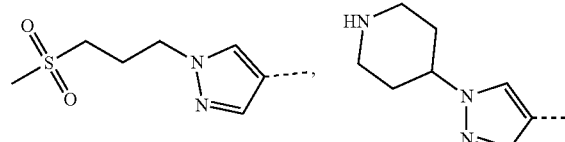
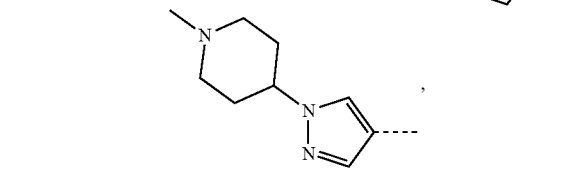
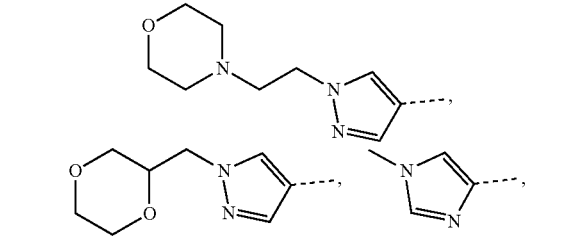
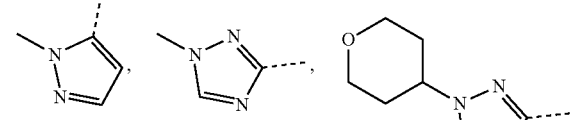
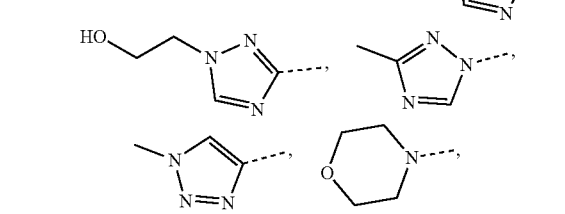

-continued

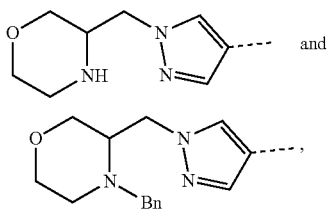 and , and other variables are as defined in the present disclosure.

Other embodiments of the present disclosure are generated by any combination of the above-mentioned variables.

In some embodiments of the present disclosure, the above-mentioned compound or pharmaceutically acceptable salt thereof is selected from

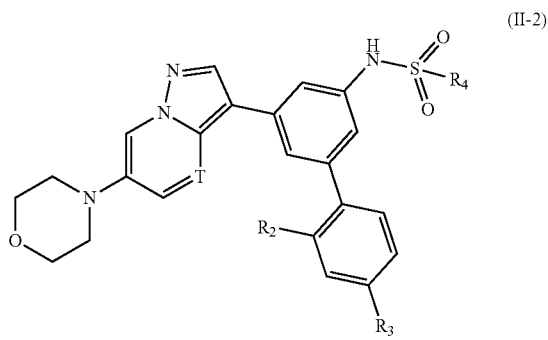
(II-2)

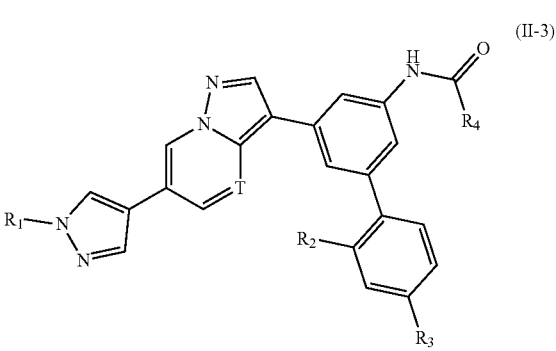
(II-3)

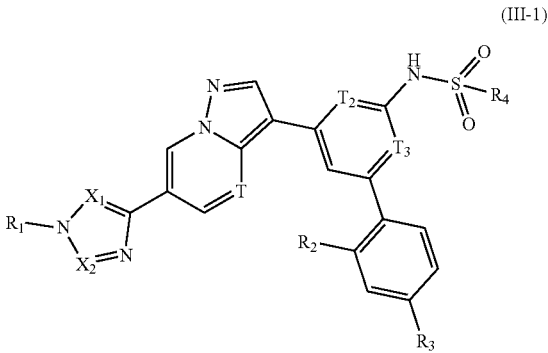
(III-1)

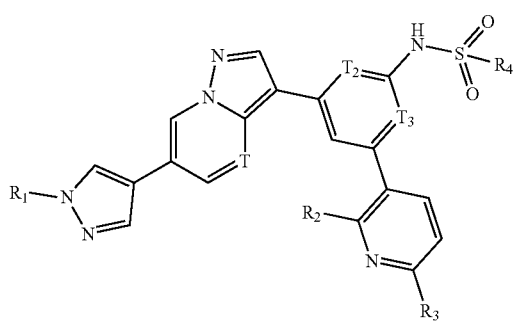
(III-2)
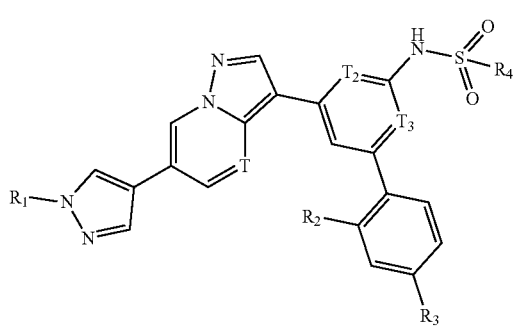
(III-3)
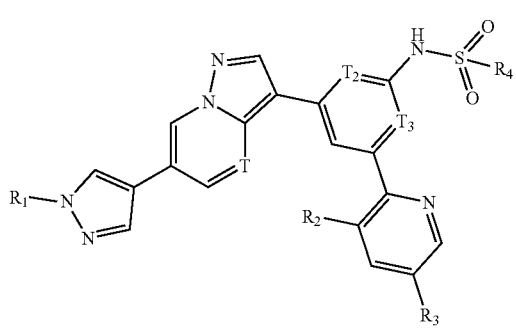
(III-4)
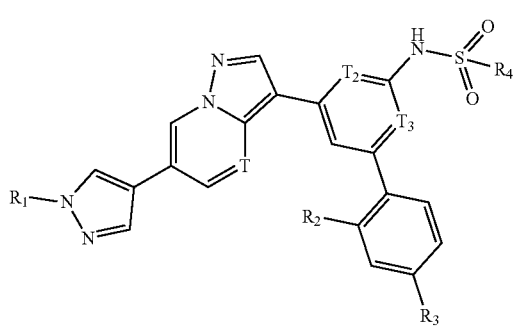
(III-5)
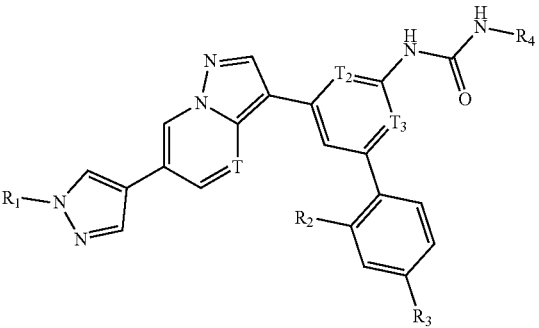
(III-6)
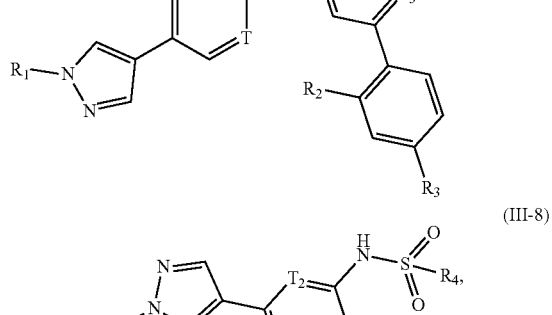
(III-7)
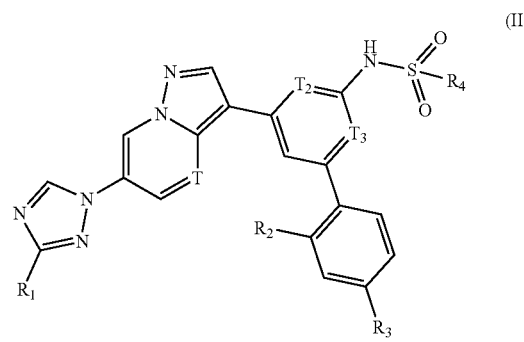
(III-8)
wherein
$X_1$ and $X_2$ are each independently selected from CH and N, and $X_1$ and $X_2$ are not simultaneously selected from N;
$R_1$, $R_2$, $R_3$, $R_4$, T, $T_1$ and $T_2$ are as defined in the present disclosure.
The present disclosure also provides a compound represented by the following formula or a pharmaceutically acceptable salt thereof:
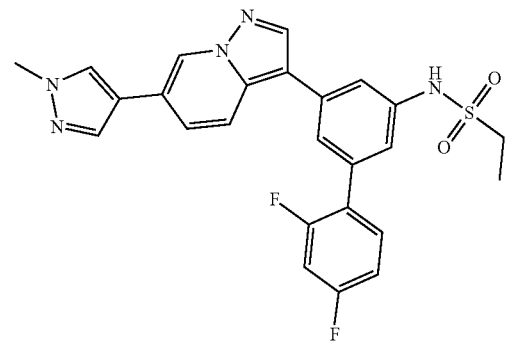

17
-continued
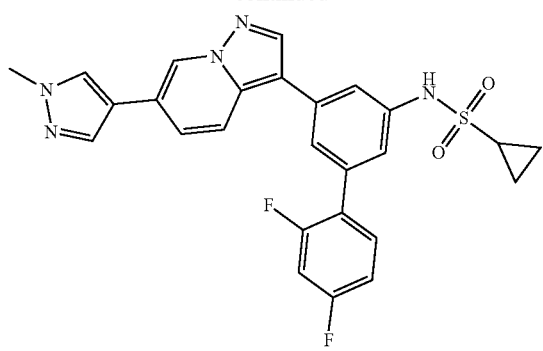
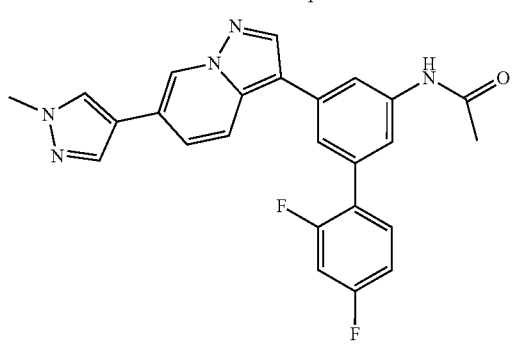
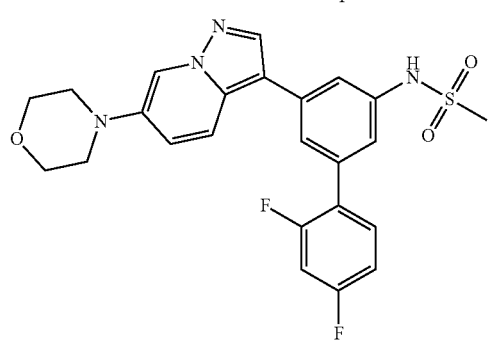
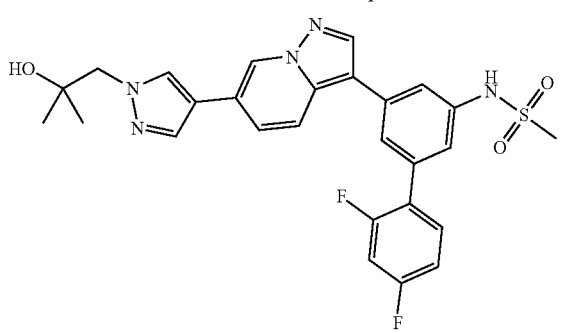
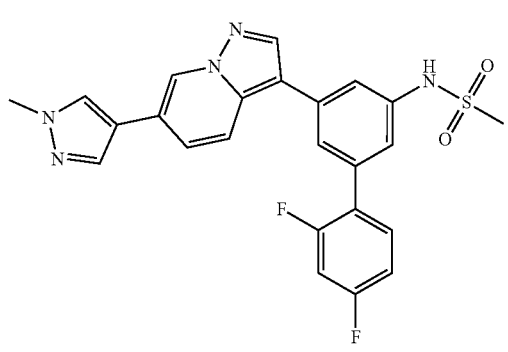
18
-continued
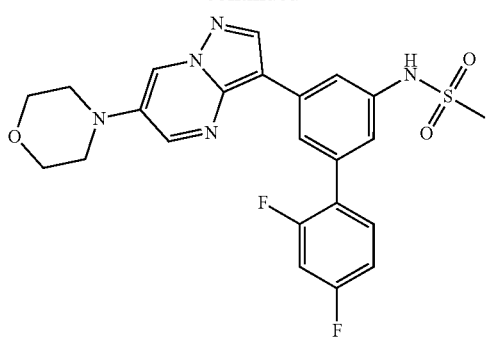
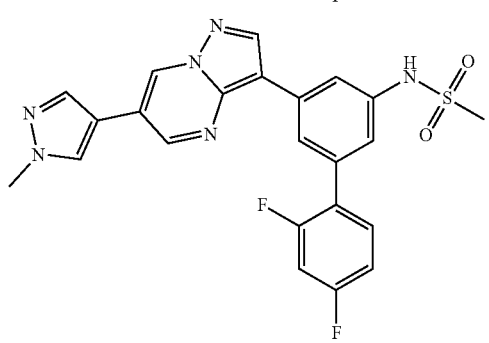
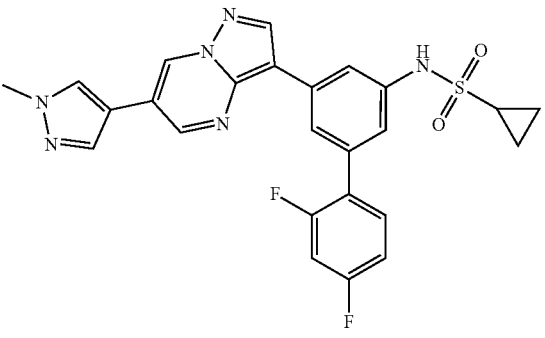
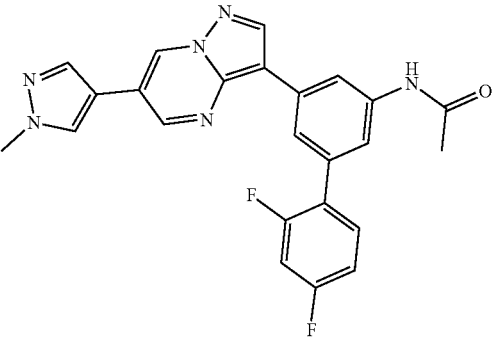
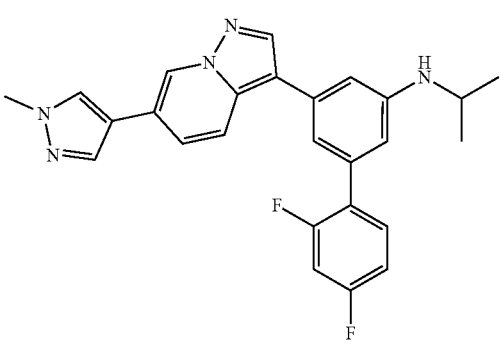

-continued
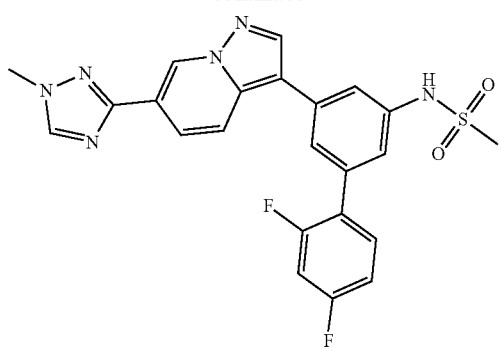
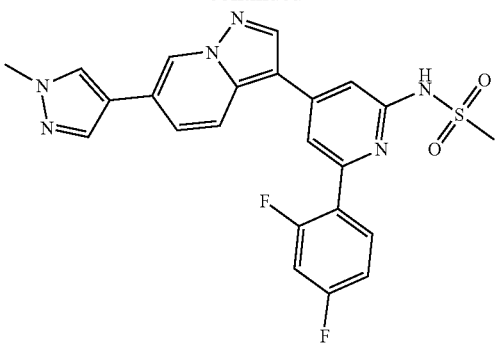
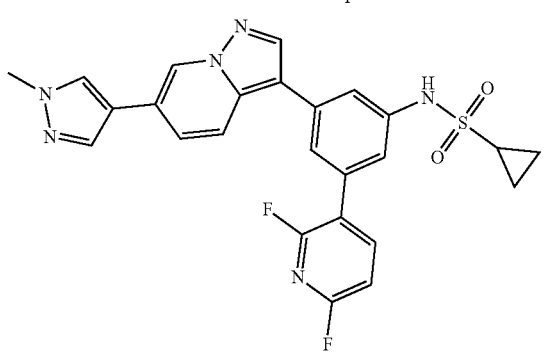
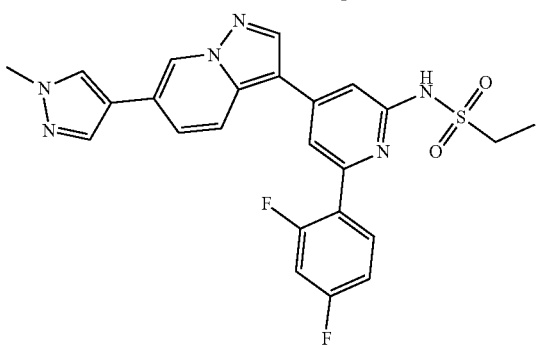
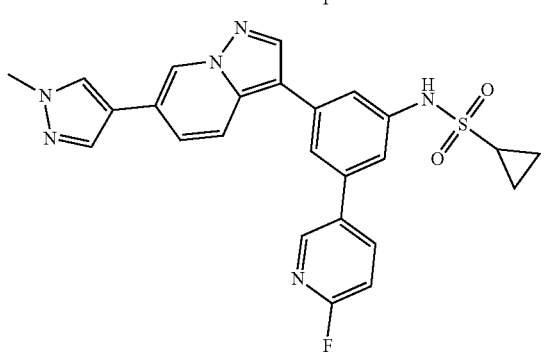
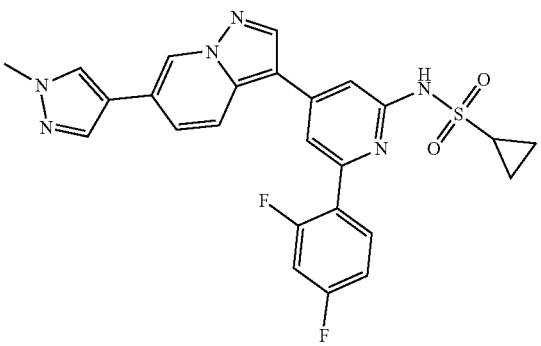
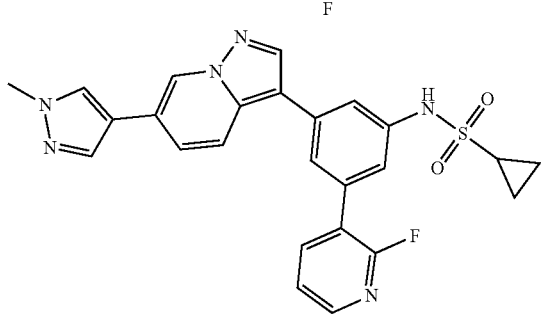
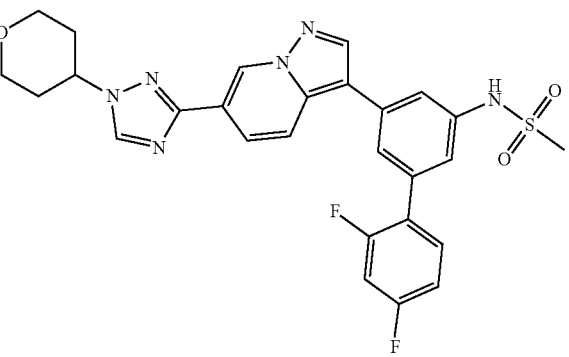
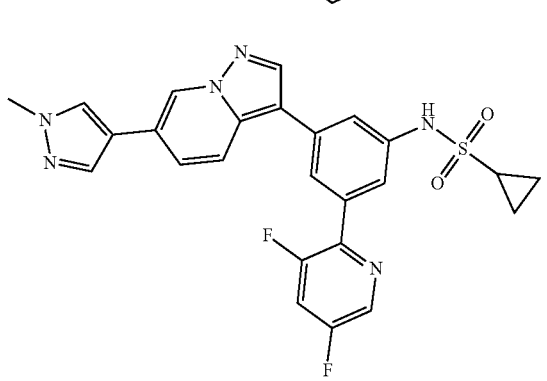
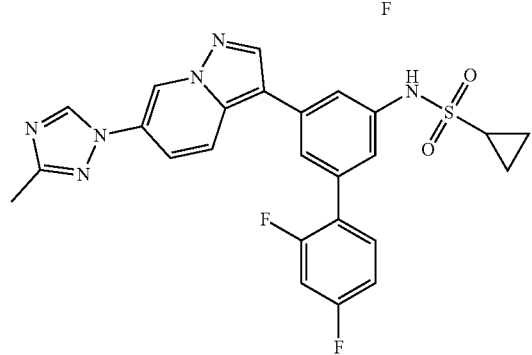

21
-continued
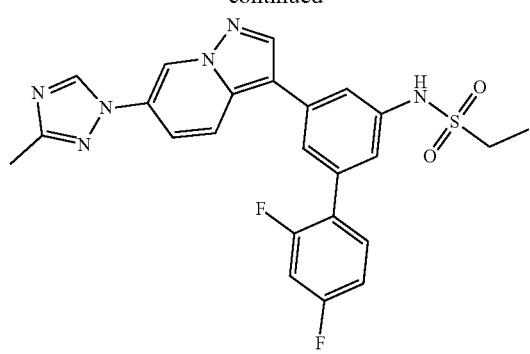
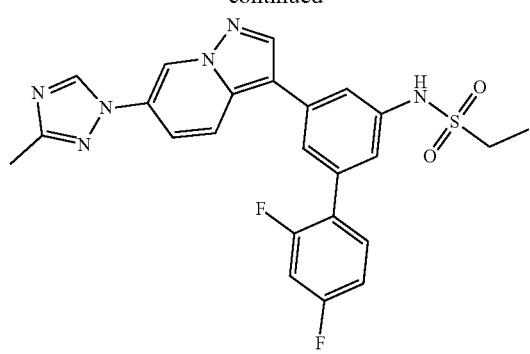
22
-continued
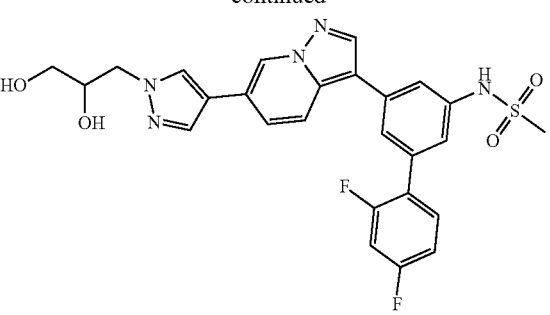
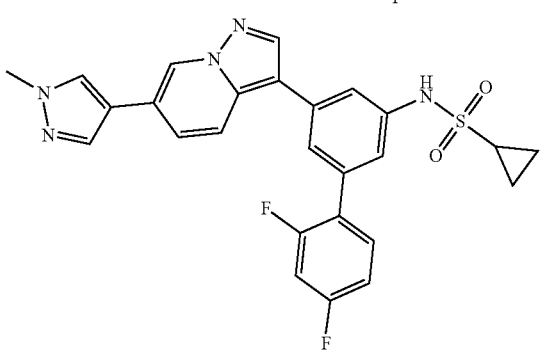
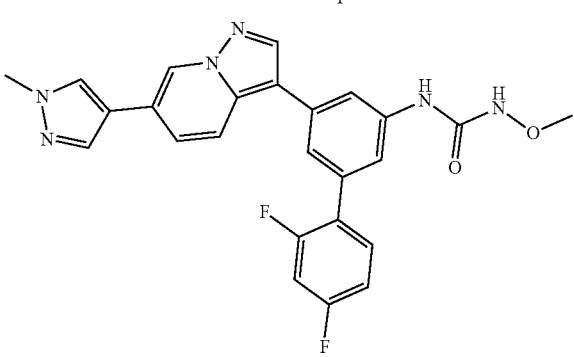
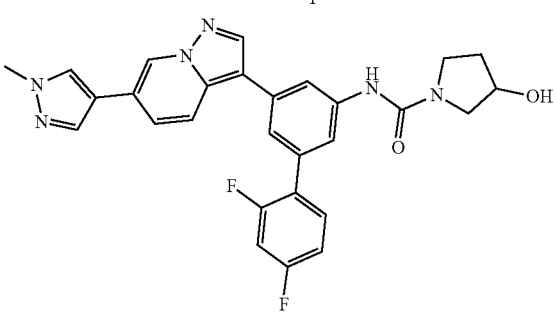
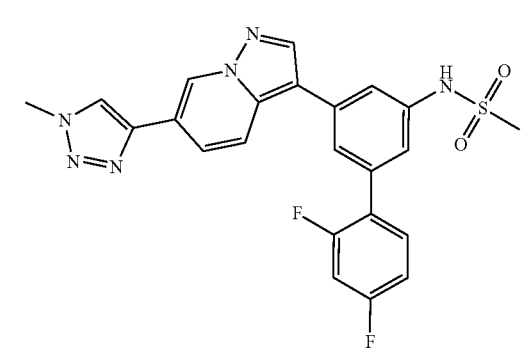

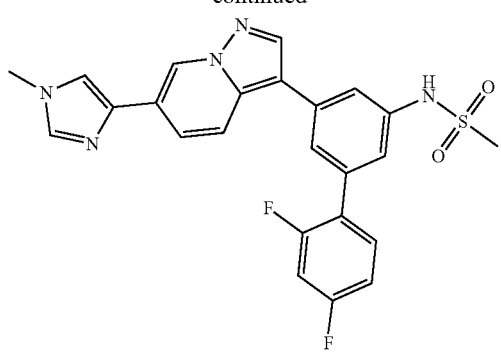
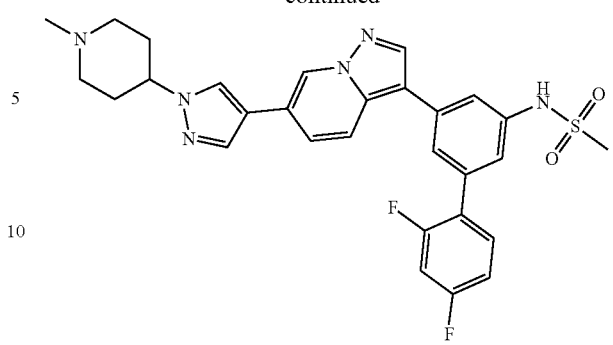
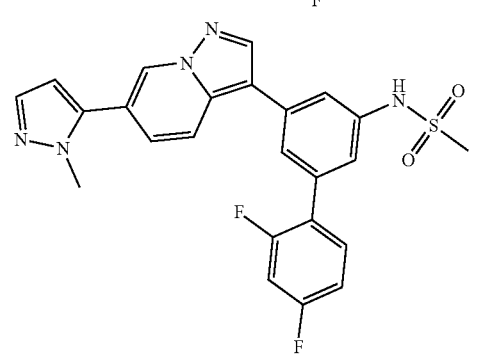
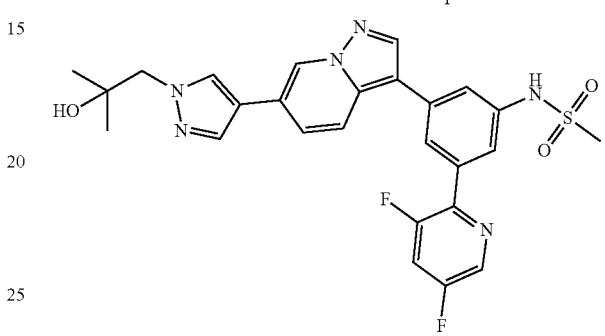
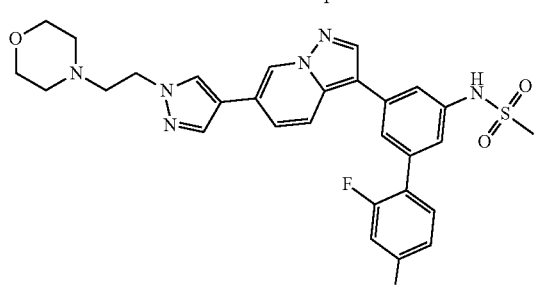
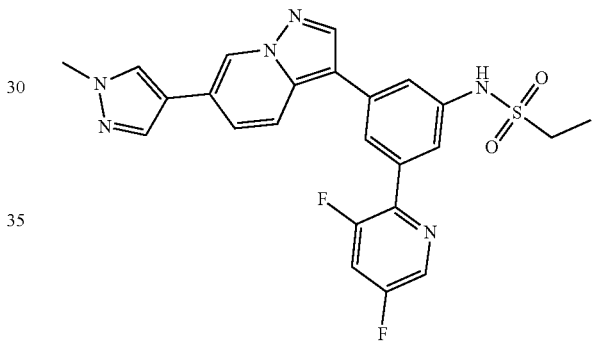
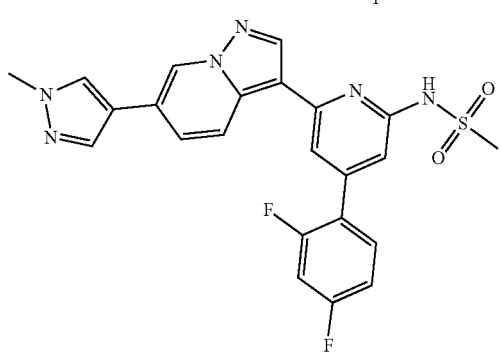
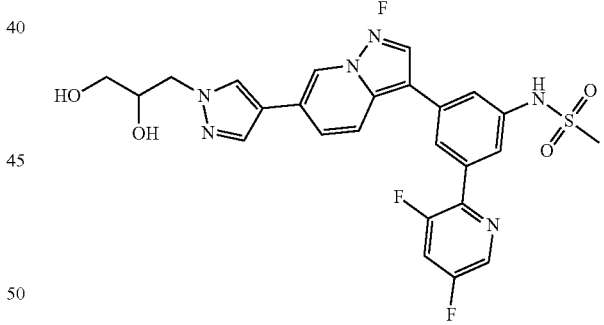
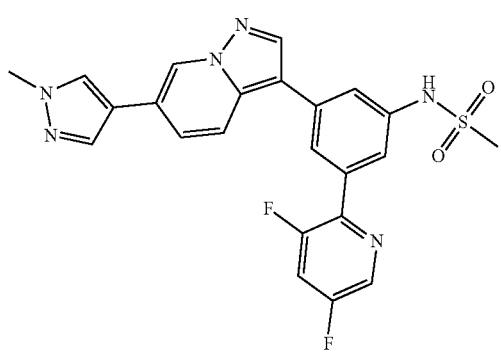
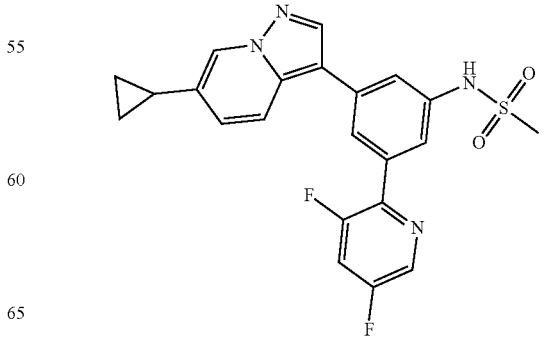

25
-continued
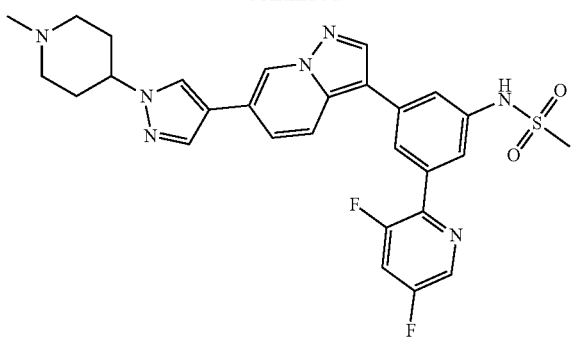
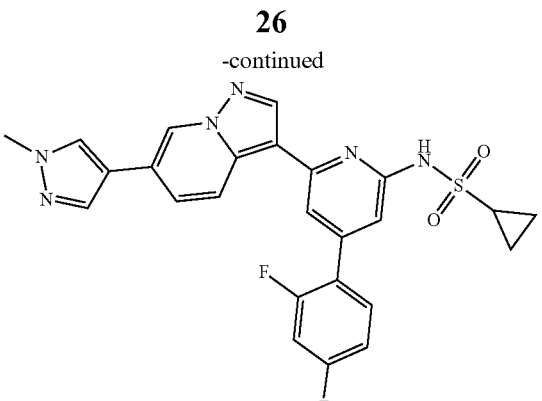
26
-continued
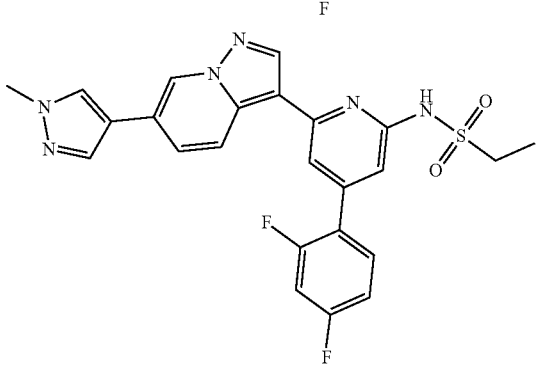
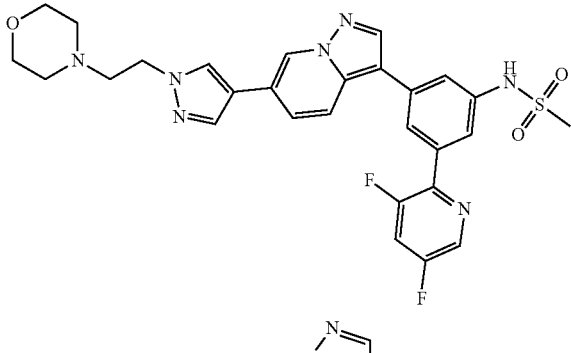
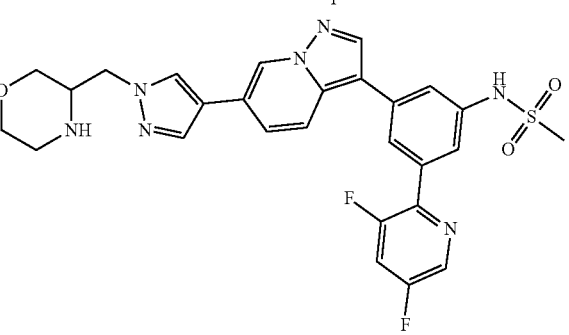
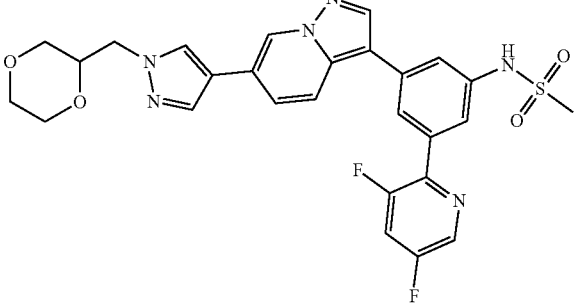
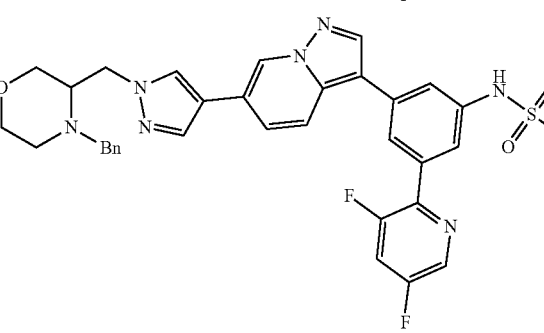
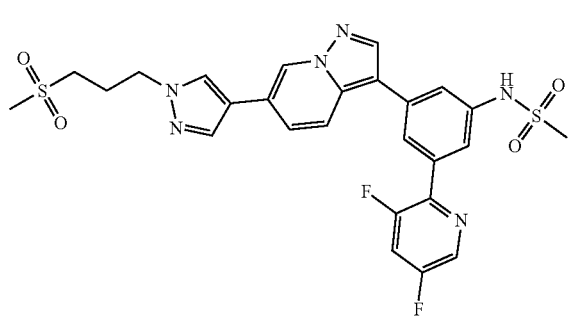
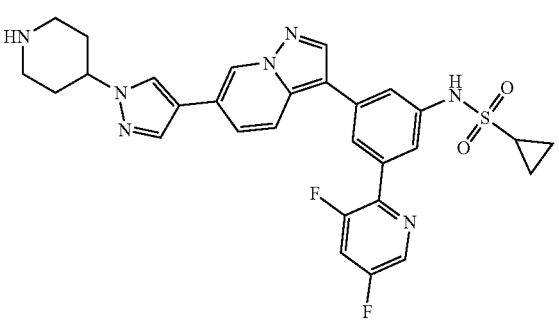

-continued

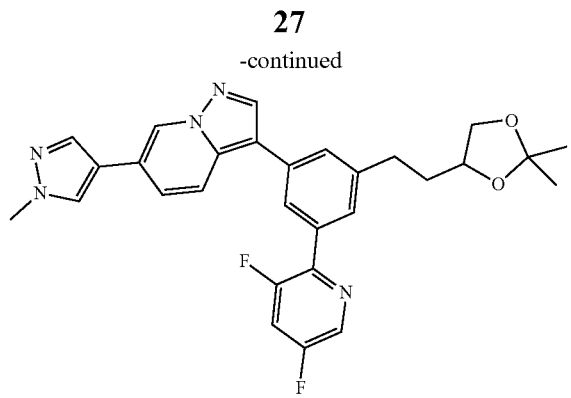

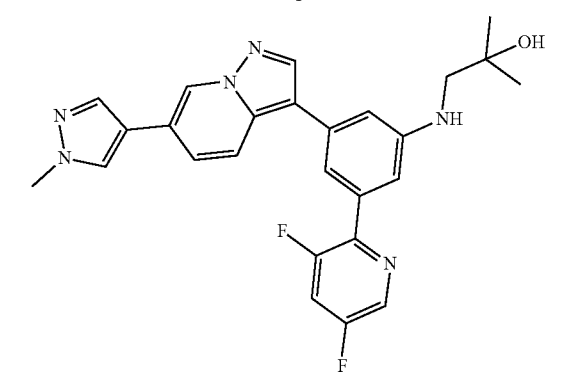

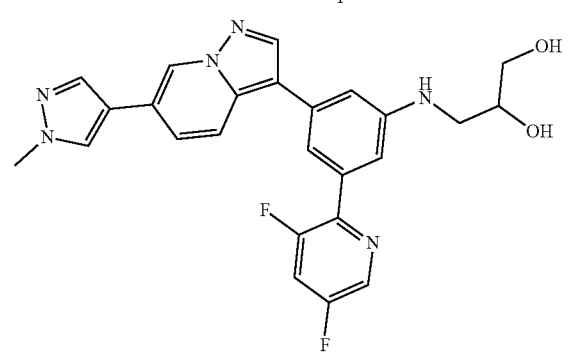

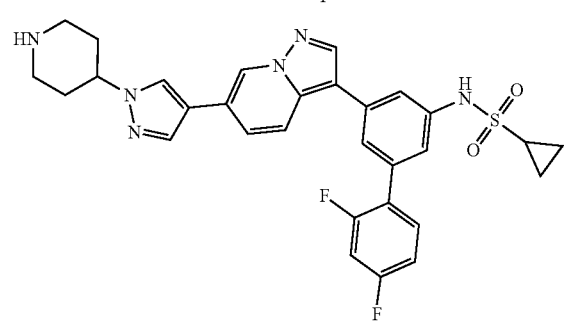

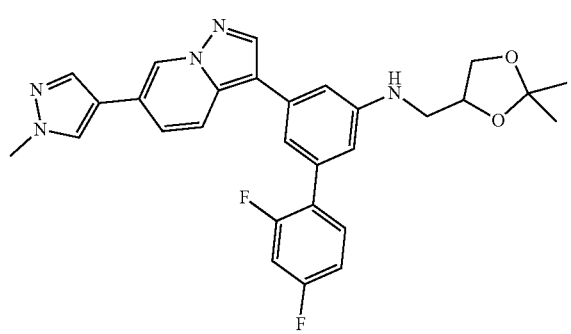

-continued

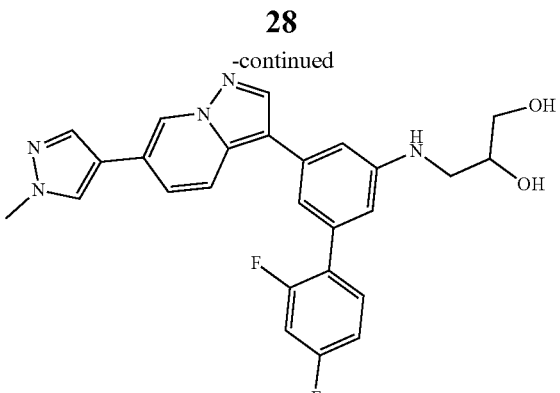

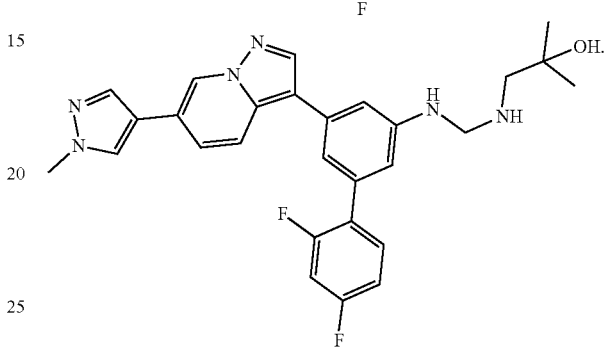

The present disclosure also provides a pharmaceutical composition comprising a therapeutically effective amount of the above-mentioned compound or pharmaceutically acceptable salt thereof as an active ingredient and a pharmaceutically acceptable carrier.

The present disclosure further provides use of the above-mentioned compound or pharmaceutically acceptable salt thereof, or the above-mentioned composition in the preparation of an FGFR and VEGFR dual inhibitor-related medicament.

In some embodiments of the present disclosure, in the above-mentioned use, the FGFR and VEGFR dual inhibitor-related medicament is a medicament for solid tumors.

Definition and Description

Unless otherwise stated, the following terms and phrases used herein are intended to have the following meanings. A specific term or phrase should not be considered uncertain or unclear unless specifically defined, but should be understood in its ordinary meaning. When a trade name appears herein, it is intended to refer to the corresponding commodity or an active ingredient thereof.

The term "pharmaceutically acceptable" as used herein refers to those compounds, materials, compositions and/or dosage forms, which are, within the scope of sound medical judgment, suitable for use in contact with human and animal tissues, without excessive toxicity, irritation, allergic reactions or other problems or complications, which is commensurate with a reasonable benefit/risk ratio.

The term "pharmaceutically acceptable salt" refers to a salt of the compound of the present disclosure, which is prepared from the compound having specific substituents found in the present disclosure with relatively non-toxic acids or bases. When compounds of the present disclosure contain relatively acidic functional groups, base addition salts can be obtained by contacting the neutral form of such compounds with a sufficient amount of base, either in pure solution or a suitable inert solvent. Pharmaceutically acceptable base addition salts include sodium, potassium, calcium, ammonium, organic amine or magnesium salts or similar salts. When compounds of the present disclosure contain relatively basic functional groups, acid addition salts can be obtained by contacting the neutral form of such compounds with a sufficient amount of acid, either in pure solution or a suitable inert solvent. Examples of pharmaceutically acceptable acid addition salts include salts of inorganic acids, which include, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid and phosphorous acid; and salts of organic acids, which include, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid; and also include salts of amino acids (such as arginine), and salts of organic acids such as glucuronic acid. Certain specific compounds of the present disclosure contain basic and acidic functional groups and thus can be converted to any base or acid addition salt.

The pharmaceutically acceptable salts of the present disclosure can be synthesized from a parent compound containing acid radicals or base radicals by conventional chemical methods. In general, the method for preparing such salts comprises: in water or an organic solvent or a mixture of both, reacting these compounds in free acid or base forms with a stoichiometric amount of a suitable base or acid to prepare the salts.

In addition to salt forms, the compounds provided by the present disclosure also exist in prodrug forms. The prodrugs of the compounds described herein are prone to chemical changes under physiological conditions, and thus are converted into the compounds of the present disclosure. In addition, prodrugs can be converted to the compounds of the present disclosure by chemical or biochemical methods in the in vivo environment.

Certain compounds of the present disclosure may exist in unsolvated or solvated forms, including hydrated forms. Generally speaking, the solvated form is equivalent to the unsolvated form, and both are included in the scope of the present disclosure.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers, (D)-isomers, (L)-isomers, and racemic mixtures and other mixtures thereof, such as enantiomerically or diastereomerically enriched mixtures, all of which fall within the scope of the present disclosure. Additional asymmetric carbon atoms may be present in a substituent such as an alkyl group. All these isomers and mixtures thereof are included in the scope of the present disclosure.

Unless otherwise stated, the term "enantiomer" or "optical isomer" refers to stereoisomers that are mirror images of each other.

Unless otherwise stated, the term "cis-trans isomer" or "geometric isomer" is caused by the fact that double bonds or single bonds of ring-forming carbon atoms cannot rotate freely.

Unless otherwise stated, the term "diastereomer" refers to stereoisomers in which molecules have two or more chiral centers and are not mirror images of each other.

The compounds of the present disclosure may exist in specific. Unless otherwise stated, the term "tautomer" or "tautomeric form" means that at room temperature, isomers with different functional groups are in dynamic equilibrium and can be quickly converted to each other. Where tautomerization is possible (such as in solution), a chemical equilibrium of tautomers can be achieved. For example, proton tautomers (also known as prototropic tautomers) include interconversion via migration of a proton, such as keto-enol isomerization and imine-enamine isomerization. Valence tautomers include some interconversions by recombination of some of bond-forming electrons. A specific example of keto-enol tautomerization is the interconversion between two tautomers, pentane-2,4-dione and 4-hydroxypent-3-en-2-one.

Optically active (R)- and (9-isomers and D and L isomers can be prepared using chiral synthesis or chiral reagents or other conventional techniques. If a particular enantiomer of a compound of the present disclosure is desired, it can be prepared by asymmetric synthesis or derivatization with a chiral auxiliary, wherein the resulting diastereomeric mixture is separated and the auxiliary groups are cleaved to provide pure desired enantiomers. Alternatively, where the molecule contains a basic functional group (such as an amino group) or an acidic functional group (such as a carboxyl group), diastereomeric salts can be formed with an appropriate optically active acid or base, followed by resolution of the diastereomers using conventional methods well known in the art, and subsequent recovery of the pure enantiomers. In addition, separation of enantiomers and diastereomers is frequently accomplished using chromatography, which uses chiral stationary phases, optionally in combination with chemical derivatization methods (e.g., formation of carbamates from amines).

The compounds of the present disclosure may contain unnatural proportions of atomic isotopes at one or more of the atoms constituting the compound. For example, the compounds may be radiolabeled with radioactive isotopes, such as tritium ($^3H$), iodine-125 ($^{125}I$) or C-14 ($^{14}C$.)

For another example, the hydrogen can be substituted by heavy hydrogen to form deuterated drugs. The bond formed by deuterium and carbon is stronger than the bond formed by ordinary hydrogen and carbon. Compared with undeuterated drugs, deuterated drugs have reduced toxic side effects, increased drug stability, enhanced efficacy, prolonged biological half-life of drugs and other advantages. All isotopic variations of the compounds of the present disclosure, whether radioactive or not, are intended to be encompassed within the scope of the present disclosure.

The term "optional" or "optionally" means that the subsequently described event or circumstance may, but not necessarily occur, and that the description includes instances where said event or circumstance occurs and instances where said event or circumstance does not occur.

The term "substituted" means that any one or more hydrogen atoms on the designated atom are substituted by a substituent, which may include heavy hydrogen and hydrogen variants, provided that the valence state of the designated atom is normal, and the substituted compound is stable. Where the substituent is oxygen (i.e., =O), it means that two hydrogen atoms are substituted. Oxygen substitution does not occur on aromatic groups. The term "optionally substituted" means that it may or may not be substituted. Unless otherwise specified, the type and number of substituents may be arbitrary on the basis that they can be achieved in chemistry.

Where any variable (such as R) appears more than once in the composition or structure of a compound, its definition in each case is independent. Thus, for example, if a group is substituted with 0-2 R, the group can optionally be substituted with up to two R, and R in each case has independent options. In addition, combinations of substituents and/or variants thereof are permissible only if such combinations result in stable compounds.

When the number of a linking group is 0, such as —(CRR)₀—, it means that the linking group is a single bond.

When the number of a substituent is 0, it means that the substituent does not exist. For example, -A-(R)₀ means that the structure is actually -A.

When a substituent is vacant, it means that the substituent does not exist. For example, when X is vacant in A-X, it means that the structure is actually A.

When one of the variables is selected from a single bond, it means that the two groups to which it is connected are directly connected. For example, when L represents a single bond in A-L-Z, it means that the structure is actually A-Z.

When the bond of a substituent can be cross-connected to more than two atoms on a ring, the substituent can be bonded to any atom on the ring, for example, the structural unit

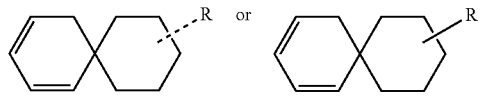

indicates that the substituent R can be substituted at any position on the cyclohexyl or cyclohexadiene. When the substituents listed do not indicate through which atom they are connected to the substituted group, such substituents can be bonded through any of the atoms thereof, for example, pyridyl as a substituent can be attached to the substituted group via any carbon atom on the pyridine ring.

When the linking group listed does not indicate the linking direction thereof, the linking direction is arbitrary, for example, the linking group L is -M-W— in

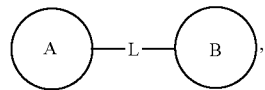

at this situation, -M-W— can connect ring A and ring B in the same direction as the reading order from left to right to form

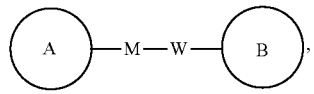

and can also connect ring A and ring B in the opposite direction as the reading order from left to right to form

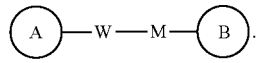

Combinations of the linking groups, substituents, and/or variants thereof are permissible only if such combinations result in stable compounds.

Unless otherwise specified, when a group has one or more connectable sites, any one or more sites of the group can be connected to other groups through chemical bonds. When the connection mode of the chemical bond is not positioned, and there is an H atom at the connectable site, the number of H atoms at the site will decrease correspondingly with the number of chemical bonds connected to become a group with the corresponding valence when the chemical bond is connected. The chemical bonds between the sites and other groups can be represented by a straight solid bond (/), a straight dashed bond (⟋), or a wavy line (

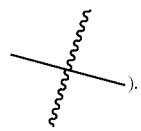).

For example, the straight solid bond in —OCH₃ means that the group is connected to other groups through the oxygen atom in the group; the straight dashed bond in

means that the group is connected to other groups through the two ends of the nitrogen atom in the group; the wavy line in

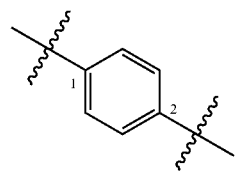 [SMILES: *c1ccc(*)cc1]

means that the group is connected to other groups through the 1 and 2 carbon atoms in the phenyl group;

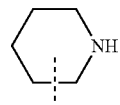

means that any connectable site on the piperidinyl can be connected to other groups through one chemical bond, including at least four connection modes:

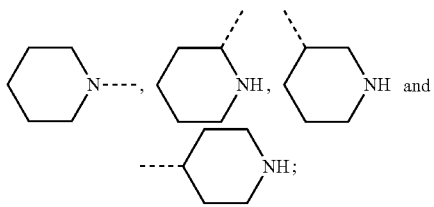

even if the H atom is drawn on —N—,

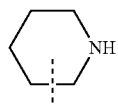

still includes the group of the connection mode but

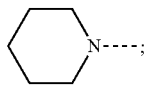

the H at the site will decrease correspondingly by one and become the corresponding monovalent piperidinyl when one chemical bond is connected.

Unless otherwise specified, the term "$C_{1-3}$ alkyl" is used to represent a linear or branched saturated hydrocarbon group consisting of 1 to 3 carbon atoms. The $C_{1-3}$ alkyl includes $C_{1-2}$ alkyl, $C_{2-3}$ alkyl, etc.; and it can be monovalent (such as methyl), divalent (such as methylene) or multivalent (such as methine). Examples of $C_{1-3}$ alkyl include, but are not limited to, methyl (Me), ethyl (Et), propyl (including n-propyl and isopropyl), etc.

Unless otherwise specified, the term "$C_{1-3}$ alkoxy" means those alkyl groups containing 1 to 3 carbon atoms that are connected to the rest of the molecule through one oxygen atom. The $C_{1-3}$ alkoxy includes $C_{1-2}$ alkoxy, $C_{2-3}$ alkoxy, $C_3$ alkoxy, $C_2$ alkoxy, etc. Examples of $C_{1-3}$ alkoxy include, but are not limited to methoxy, ethoxy, propoxy (including n-propoxy and isopropoxy), etc.

Unless otherwise specified, "$C_{3-5}$ cycloalkyl" means a saturated cyclic hydrocarbon group consisting of 3 to 5 carbon atoms, which comprises a monocyclic ring system, and the $C_{3-5}$ cycloalkyl includes $C_{3-4}$ cycloalkyl, $C_{4-5}$ cycloalkyl, etc.; and it can be monovalent, bivalent or multivalent. Examples of $C_{3-5}$ cycloalkyl include, but are not limited to, cyclopropyl, cyclobutyl, cyclopentyl, etc.

Unless otherwise specified, the terms "5- to 6-membered heteroaryl ring" and "5- to 6-membered heteroaryl" of the present disclosure can be used interchangeably, and the term "5- to 6-membered heteroaryl" represents a monocyclic group having a conjugated π-electron system and consisting of 5 to 6 ring atoms, of which 1, 2, 3 or 4 ring atoms are heteroatoms independently selected from O, S and N, and the rest of which are carbon atoms, wherein the nitrogen atom is optionally quaternized, and the nitrogen and sulfur heteroatoms can be optionally oxidized (i.e., NO and $S(O)_p$, wherein p is 1 or 2). The 5- to 6-membered heteroaryl can be connected to the rest of the molecule through a heteroatom or a carbon atom. The 5- to 6-membered heteroaryl includes 5-membered and 6-membered heteroaryl. Examples of the 5- to 6-membered heteroaryl include, but are not limited to, pyrrolyl (including N-pyrrolyl, 2-pyrrolyl, 3-pyrrolyl, etc.), pyrazolyl (including 2-pyrazolyl, 3-pyrazolyl, etc.), imidazolyl (including N-imidazolyl, 2-imidazolyl, 4-imidazolyl, 5-imidazolyl, etc.), oxazolyl (including 2-oxazolyl, 4-oxazolyl, 5-oxazolyl, etc.), triazolyl (1H-1,2,3-triazolyl, 2H-1,2,3-triazolyl, 1H-1,2,4-triazolyl, 4H-1,2,4-triazolyl, etc.), tetrazolyl, isoxazolyl (including 3-isoxazolyl, 4-isoxazolyl, 5-isoxazolyl, etc.), thiazolyl (including 2-thiazolyl, 4-thiazolyl, 5-thiazolyl, etc.), furyl (including 2-furanyl, 3-furanyl, etc.), thienyl (including 2-thienyl, 3-thienyl, etc.), pyridyl (including 2-pyridyl, 3-pyridyl, 4-pyridyl, etc.), pyrazinyl or pyrimidinyl (including 2-pyrimidyl, 4-pyrimidyl, etc.).

Unless otherwise specified, the term "5- to 6-membered heterocycloalkyl" by itself or in combination with other terms respectively represents a saturated cyclic group consisting of 5 to 6 ring atoms, of which 1, 2, 3 or 4 ring atoms are heteroatoms independently selected from O, S and N, and the rest of which are carbon atoms, wherein the nitrogen atom is optionally quaternized, and the nitrogen and sulfur heteroatoms can be optionally oxidized (i.e., NO and $S(O)_p$, wherein p is 1 or 2). It comprises a monocyclic and bicyclic ring system, wherein the bicyclic system includes a spiro ring, a fused ring, and a bridged ring. In addition, in terms of the "5- to 6-membered heterocycloalkyl", the heteroatom may occupy the position at which the heterocycloalkyl is connected to the rest of the molecule. The 5- to 6-membered heterocycloalkyl includes 5-membered and 6-membered heterocycloalkyl. Examples of 5- to 6-membered heterocycloalkyl include, but are not limited to, pyrrolidinyl, pyrazolidinyl, imidazolidinyl, tetrahydrothienyl (including tetrahydrothien-2-yl, tetrahydrothien-3-yl, etc.), tetrahydrofuranyl (including tetrahydrofuran-2-yl), tetrahydropyranyl, piperidinyl (including 1-piperidinyl, 2-piperidinyl, 3-piperidinyl, etc.), piperazinyl (including 1-piperazinyl, 2-piperazinyl, etc.), morpholinyl (including 3-morpholinyl, 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl or homopiperidinyl.

Unless otherwise specified, the term "3- to 6-membered heterocycloalkyl" by itself or in combination with other terms respectively represents a saturated cyclic group consisting of 3 to 6 ring atoms, of which 1, 2, 3 or 4 ring atoms are heteroatoms independently selected from O, S and N, and the rest of which are carbon atoms, wherein the nitrogen atom is optionally quaternized, and the nitrogen and sulfur heteroatoms can be optionally oxidized (i.e., NO and $S(O)_p$, wherein p is 1 or 2). It comprises a monocyclic and bicyclic ring system, wherein the bicyclic system includes a spiro ring, a fused ring, and a bridged ring. In addition, in terms of the "3- to 6-membered heterocycloalkyl", the heteroatom may occupy the position at which the heterocycloalkyl is connected to the rest of the molecule. The 3- to 6-membered heterocycloalkyl includes 4- to 6-membered, 5- to 6-membered, 4-membered, 5-membered, 6-membered heterocycloalkyl, etc. Examples of 3- to 6-membered heterocycloalkyl include, but are not limited to, azetidinyl, oxetanyl, thiatanyl, pyrrolidinyl, pyrazolidinyl, imidazolidinyl, tetrahydrothienyl (including tetrahydrothien-2-yl, tetrahydrothien-3-yl, etc.), tetrahydrofuranyl (including tetrahydrofuran-2-yl, etc.), tetrahydropyranyl, piperidinyl (including 1-piperidinyl, 2-piperidinyl, 3-piperidinyl, etc.), piperazinyl (including 1-piperazinyl, 2-piperazinyl, etc.), morpholinyl (including 3-morpholinyl, 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl or homopiperidinyl.

The term "leaving group" refers to a functional group or atom that can be substituted by another functional group or atom through a substitution reaction (e.g., an affinity substitution reaction). For example, representative leaving groups include trifluoromethanesulfonate; chlorine, bromine and iodine; sulfonates, such as methanesulfonate, tosylate, p-bromobenzenesulfonate, and p-toluenesulfonate; and acyloxy, such as acetoxy and trifluoroacetoxy.

The term "protecting group" includes, but is not limited to, "amino protecting group", "hydroxy protecting group" or "mercapto protecting group". The term "amino protecting group" refers to a protecting group suitable for preventing side reactions occurring at the nitrogen atom of an amino group. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), triphenyl methyl (Tr), 1,1-bis-(4'-methoxyphenyl)methyl; silyl, such as trimethylsilyl (TMS) and tert-butyldimethylsilyl (TBS). The term "hydroxyl protecting group" refers to a protecting group suitable for preventing side reactions of a hydroxyl group. Representative hydroxyl protecting groups include, but are not limited to: alkyl, such as methyl, ethyl and tert-butyl; acyl, such as alkanoyl (e.g., acetyl); aryl methyl, such as benzyl (Bn), p-methoxybenzyl (PMB), 9-fluorenylmethyl (Fm) and diphenylmethyl (DPM); silyl, such as trimethylsilyl (TMS) and tert-butyldimethylsilyl (TBS).

The compounds of the present disclosure can be prepared by various synthetic methods well known to a person skilled in the art, including the specific embodiments listed below, the embodiments formed by the combination with other chemical synthesis methods, and equivalent alternative embodiments well known to a person skilled in the art, wherein the preferred embodiments include but are not limited to the examples of the present disclosure.

The solvents used in the present disclosure are commercially available.

The present disclosure uses the following abbreviations: aq represents water; eq represents equivalent; DCM represents dichloromethane; PE represents petroleum ether; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amine protecting group; BOC represents tert-butoxycarbonyl, which is an amine protecting group; HOAc represents acetic acid; r.t. represents room temperature; O/N represents overnight; THF represents tetrahydrofuran; Boc$_2$O represents di-tert-butyl dicarbonate; TFA represents trifluoroacetic acid; DIPEA represents diisopropylethylamine; SOCl$_2$ represents thionyl chloride; NIS represents N-iodosuccinimide; iPrOH represents 2-propanol; mp represents melting point; Xantphos represents 4,5-bisdiphenylphosphino-9,9-dimethylxanthene; LiAlH$_4$ represents lithium aluminium tetrahydride; Pd(dba)$_2$ represents tris(dibenzylideneacetone)dipalladium; Pd(dppf)Cl$_2$ represents [1,1'-bis(diphenylphosphino)ferrocene]palladium dichloride.

Compounds are named according to conventional naming principles in the field or using ChemDraw® software, and commercially available compounds are named using supplier catalog names.

Technical Effects

Compared with Example 5 in patent WO 2013053983 (comparative example 1 in the present patent), the multiple compounds of the present disclosure with a fused ring core structure show a significant increase in the kinase activity of FGFR1 or FGFR2 and VEGFR2. In terms of the activity of SNU-16 cells, the compound of the present disclosure has an activity that is 2-10 times higher than that of the control compound 1, and is very likely to demonstrate a better therapeutic effect at a clinically lower dose. In addition, the compound of the present disclosure has an excellent hERG safety. The compound of the present disclosure has an excellent druggability, a stable in vivo metabolism, and a high oral drug absorption and bioavailability. The compound of the present disclosure demonstrates excellent tumor treatment effects at lower doses in preclinical animal models.

DETAILED DESCRIPTION OF THE PREFERRED EMBODIMENT

Comparative Example 1

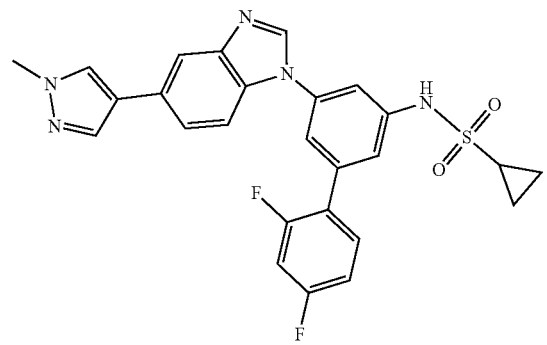 [SMILES: Cn1cc(-c2ccc3c(c2)ncn3-c2cc(NS(=O)(=O)C3CC3)cc(-c3ccc(F)cc3F)c2)cn1]

Synthetic Route

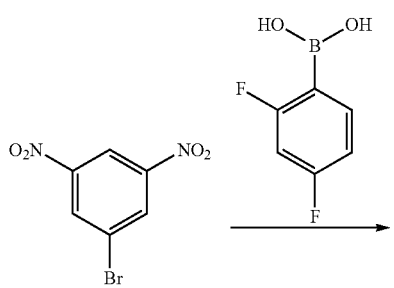

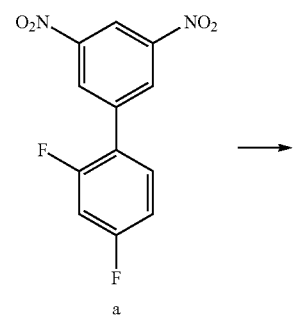

a

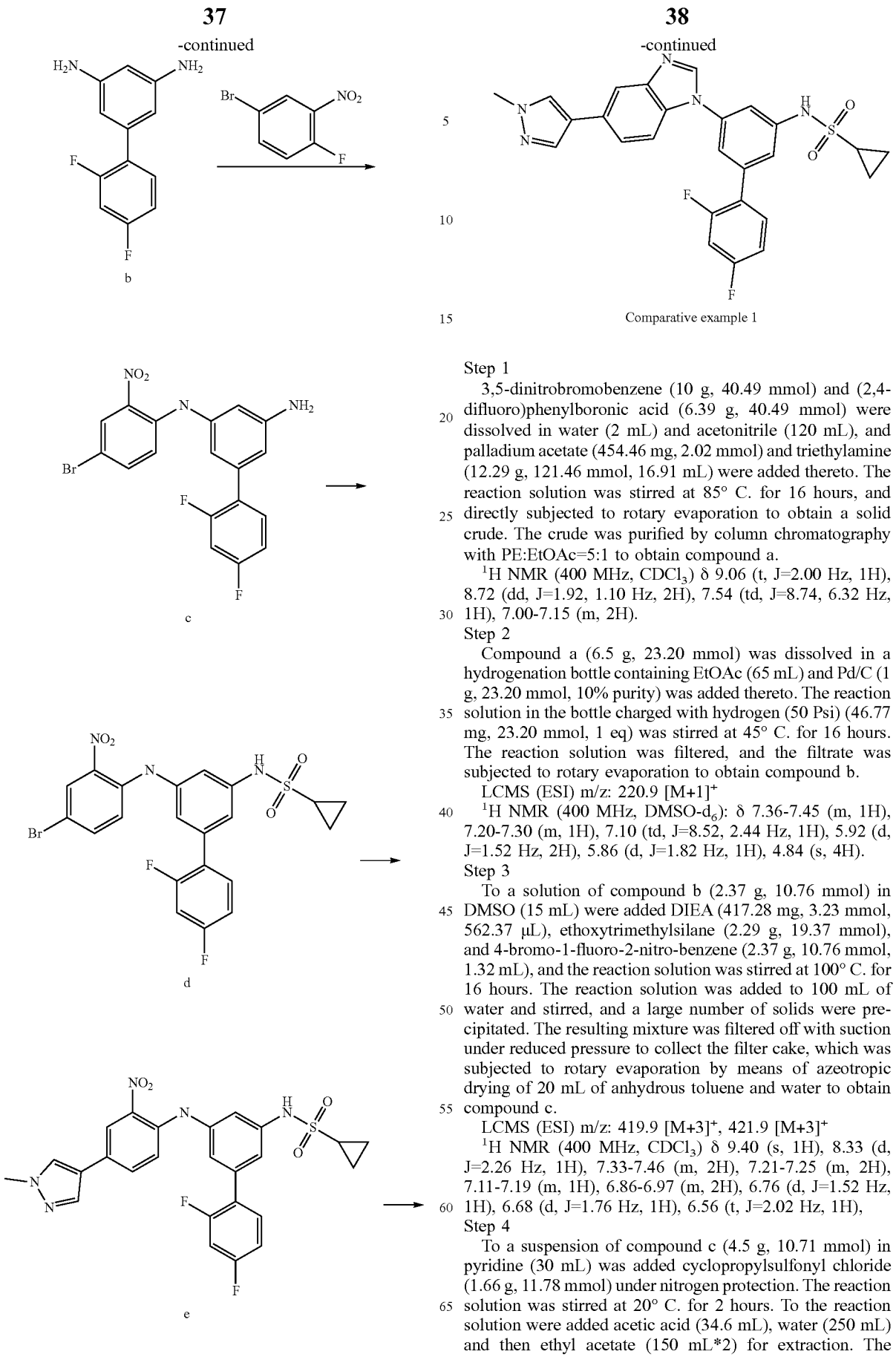

Comparative example 1

Step 1

Figure 1:
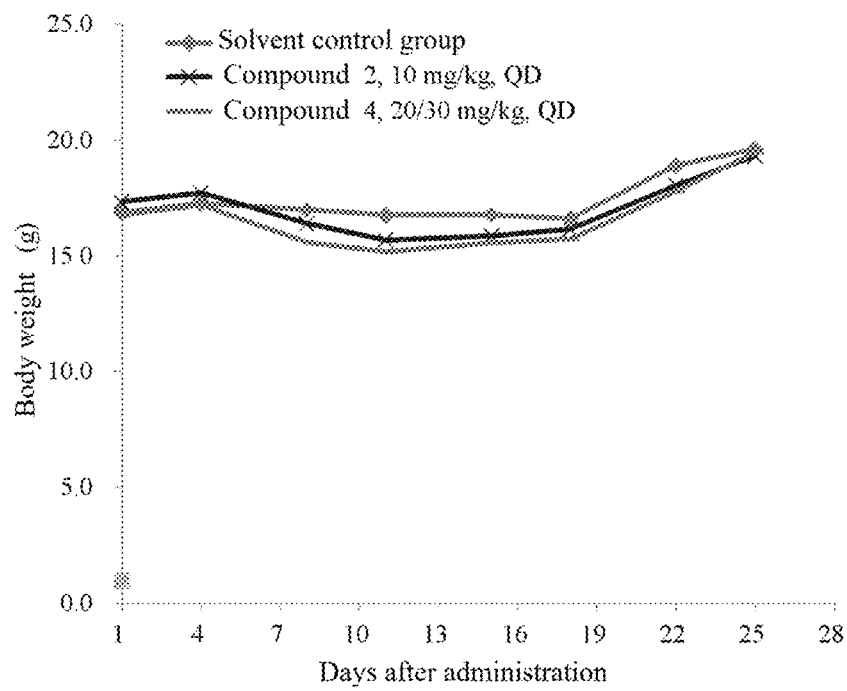
FIG. 1 is the tumor growth inhibition curve.

3,5-dinitrobromobenzene (10 g, 40.49 mmol) and (2,4-difluoro)phenylboronic acid (6.39 g, 40.49 mmol) were dissolved in water (2 mL) and acetonitrile (120 mL), and palladium acetate (454.46 mg, 2.02 mmol) and triethylamine (12.29 g, 121.46 mmol, 16.91 mL) were added thereto. The reaction solution was stirred at 85° C. for 16 hours, and directly subjected to rotary evaporation to obtain a solid crude. The crude was purified by column chromatography with PE:EtOAc=5:1 to obtain compound a.

$^1$H NMR (400 MHz, CDCl$_3$) δ 9.06 (t, J=2.00 Hz, 1H), 8.72 (dd, J=1.92, 1.10 Hz, 2H), 7.54 (td, J=8.74, 6.32 Hz, 1H), 7.00-7.15 (m, 2H).

Step 2

Compound a (6.5 g, 23.20 mmol) was dissolved in a hydrogenation bottle containing EtOAc (65 mL) and Pd/C (1 g, 23.20 mmol, 10% purity) was added thereto. The reaction solution in the bottle charged with hydrogen (50 Psi) (46.77 mg, 23.20 mmol, 1 eq) was stirred at 45° C. for 16 hours. The reaction solution was filtered, and the filtrate was subjected to rotary evaporation to obtain compound b.

LCMS (ESI) m/z: 220.9 [M+1]$^+$ $^1$H NMR (400 MHz, DMSO-d$_6$): δ 7.36-7.45 (m, 1H), 7.20-7.30 (m, 1H), 7.10 (td, J=8.52, 2.44 Hz, 1H), 5.92 (d, J=1.52 Hz, 2H), 5.86 (d, J=1.82 Hz, 1H), 4.84 (s, 4H).

Step 3

To a solution of compound b (2.37 g, 10.76 mmol) in DMSO (15 mL) were added DIEA (417.28 mg, 3.23 mmol, 562.37 μL), ethoxytrimethylsilane (2.29 g, 19.37 mmol), and 4-bromo-1-fluoro-2-nitro-benzene (2.37 g, 10.76 mmol, 1.32 mL), and the reaction solution was stirred at 100° C. for 16 hours. The reaction solution was added to 100 mL of water and stirred, and a large number of solids were precipitated. The resulting mixture was filtered off with suction under reduced pressure to collect the filter cake, which was subjected to rotary evaporation by means of azeotropic drying of 20 mL of anhydrous toluene and water to obtain compound c.

LCMS (ESI) m/z: 419.9 [M+3]$^+$, 421.9 [M+3]$^+$ $^1$H NMR (400 MHz, CDCl$_3$) δ 9.40 (s, 1H), 8.33 (d, J=2.26 Hz, 1H), 7.33-7.46 (m, 2H), 7.21-7.25 (m, 2H), 7.11-7.19 (m, 1H), 6.86-6.97 (m, 2H), 6.76 (d, J=1.52 Hz, 1H), 6.68 (d, J=1.76 Hz, 1H), 6.56 (t, J=2.02 Hz, 1H),

Step 4

To a suspension of compound c (4.5 g, 10.71 mmol) in pyridine (30 mL) was added cyclopropylsulfonyl chloride (1.66 g, 11.78 mmol) under nitrogen protection. The reaction solution was stirred at 20° C. for 2 hours. To the reaction solution were added acetic acid (34.6 mL), water (250 mL) and then ethyl acetate (150 mL*2) for extraction. The organic phases were combined, dried over anhydrous sodium sulfate, and concentrated under reduced pressure to obtain compound d.

LCMS (ESI) m/z: 523.8 [M+1]+, 525.8 [M+3]+

Step 5

To a solution of compound d (5.6 g, 10.68 mmol) and 1-methyl-4-pyrazole borate (2.78 g, 13.35 mmol) in dimethyl sulfoxide (110 mL)/water (30 mL) were added triphenylphosphine (1.40 g, 5.34 mmol), palladium acetate (359.67 mg, 1.60 mmol), and potassium carbonate (3.84 g, 27.77 mmol). The reaction solution was stirred at 100° C. for 16 hours under nitrogen protection. The reaction solution was added to stirring water (200 mL), and a solid was precipitated. The resulting mixture was filtered off with suction under reduced pressure to collect the filter cake, which was transferred to a single-necked bottle with dichloromethane, and then concentrated under reduced pressure to obtain a crude. The crude was purified by column (flash silica gel column chromatography) with PE/EtOAc=0/1 to obtain compound e.

LCMS (ESI) m/z: 526.4 [M+3]+

$^1$H NMR (400 MHz, CDCl$_3$) δ 9.45 (s, 1H), 8.29 (d, J=2.02 Hz, 1H), 7.73 (s, 1H), 7.62 (s, 1H), 7.53-7.58 (m, 1H), 7.37-7.48 (m, 2H), 7.16-7.24 (m, 3H), 6.90-7.01 (m, 2H), 6.71 (s, 1H), 3.96 (s, 3H), 2.52-2.65 (m, 1H), 1.22-1.26 (m, 2H), 0.98-1.11 (m, 2H).

Step 6

To a solution of compound e (2.8 g, 5.33 mmol, 1 eq) in formic acid (30 mL) was added Pd/C (1 g, 5.33 mmol, 10% purity), and the reaction solution was stirred at 30° C. for 16 hours under a hydrogen balloon (15 psi) atmosphere. The reaction solution was filtered through celite after the reaction was complete, and the filtrate was concentrated under reduced pressure to obtain a crude. The crude was purified by high performance liquid chromatography (chromatographic column: YMC-Triart Prep C18 150*40 mm*7 μm; mobile phase: [water (0.1% trifluoroacetic acid)-acetonitrile]; B (acetonitrile) %: 35%-50%, 10 min) to obtain the trifluoroacetate salt of comparative example 1.

LCMS (ESI) m/z: 506.0 [M+1]+

$^1$H NMR (400 MHz, DMSO-d$_6$) δ 10.25 (br s, 1H), 8.65 (s, 1H), 8.19 (s, 1H), 7.99 (s, 1H), 7.94 (s, 1H), 7.71-7.81 (m, 1H), 7.64-7.70 (m, 1H), 7.55-7.63 (m, 3H), 7.40-7.51 (m, 2H), 7.27 (br t, J=7.53 Hz, 1H), 3.88 (s, 3H), 2.81-2.93 (m, 1H), 0.98-1.08 (m, 4H).

The trifluoroacetate salt of comparative example 1 was added to a sodium bicarbonate solution, and extracted with ethyl acetate. The organic phase was dried over anhydrous sodium sulfate, and concentrated under reduced pressure to obtain comparative example 1.

Example 1

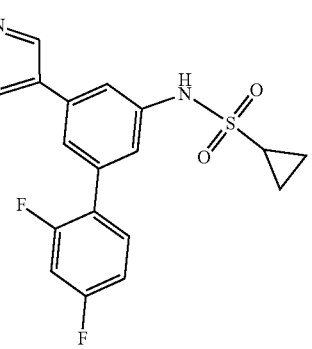

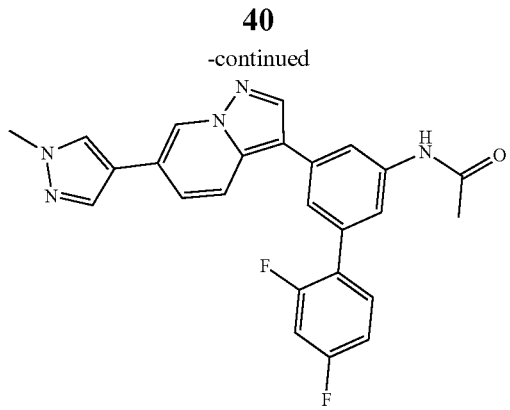

Synthetic Route

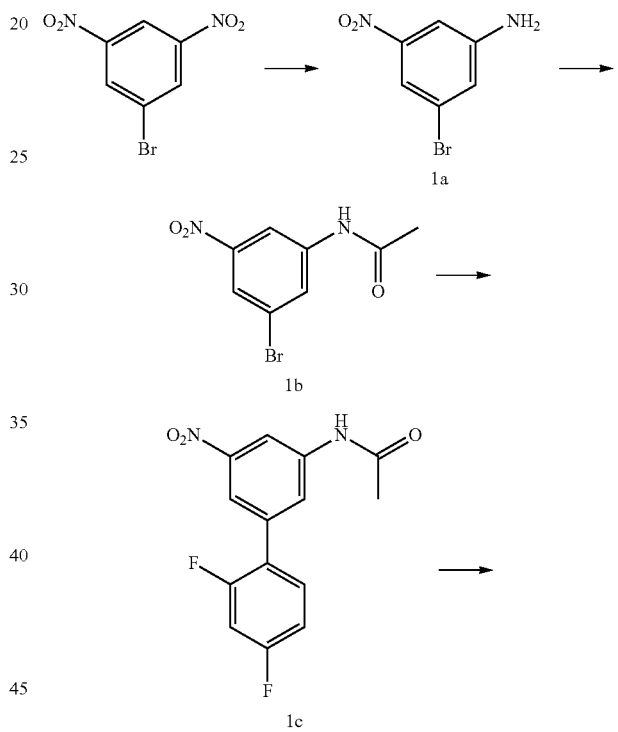

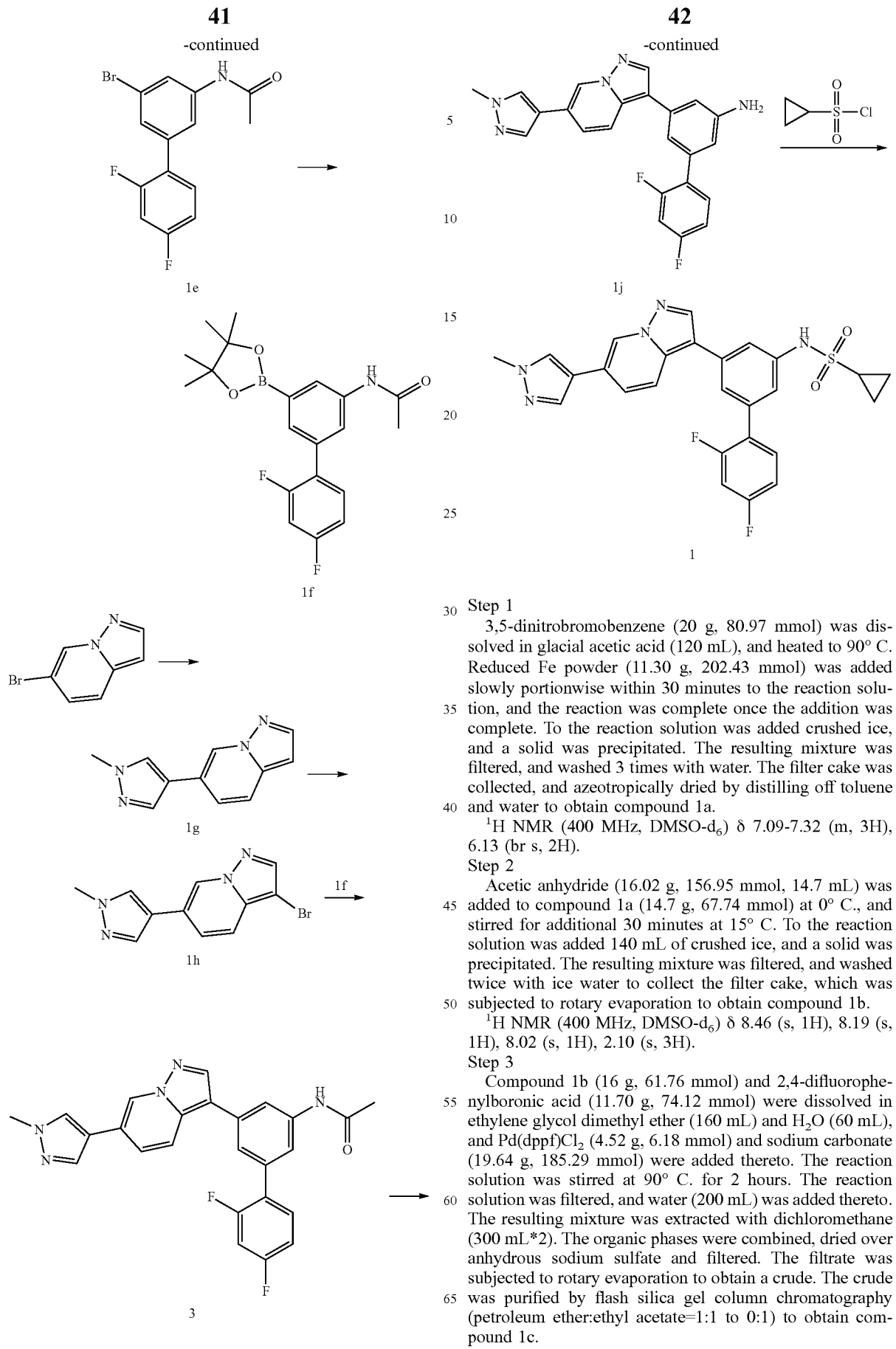

Step 1

3,5-dinitrobromobenzene (20 g, 80.97 mmol) was dissolved in glacial acetic acid (120 mL), and heated to 90° C. Reduced Fe powder (11.30 g, 202.43 mmol) was added slowly portionwise within 30 minutes to the reaction solution, and the reaction was complete once the addition was complete. To the reaction solution was added crushed ice, and a solid was precipitated. The resulting mixture was filtered, and washed 3 times with water. The filter cake was collected, and azeotropically dried by distilling off toluene and water to obtain compound 1a.

$^{1}$H NMR (400 MHz, DMSO-$d_6$) δ 7.09-7.32 (m, 3H), 6.13 (br s, 2H).

Step 2

Acetic anhydride (16.02 g, 156.95 mmol, 14.7 mL) was added to compound 1a (14.7 g, 67.74 mmol) at 0° C., and stirred for additional 30 minutes at 15° C. To the reaction solution was added 140 mL of crushed ice, and a solid was precipitated. The resulting mixture was filtered, and washed twice with ice water to collect the filter cake, which was subjected to rotary evaporation to obtain compound 1b.

$^{1}$H NMR (400 MHz, DMSO-$d_6$) δ 8.46 (s, 1H), 8.19 (s, 1H), 8.02 (s, 1H), 2.10 (s, 3H).

Step 3

Compound 1b (16 g, 61.76 mmol) and 2,4-difluorophenylboronic acid (11.70 g, 74.12 mmol) were dissolved in ethylene glycol dimethyl ether (160 mL) and H$_2$O (60 mL), and Pd(dppf)Cl$_2$ (4.52 g, 6.18 mmol) and sodium carbonate (19.64 g, 185.29 mmol) were added thereto. The reaction solution was stirred at 90° C. for 2 hours. The reaction solution was filtered, and water (200 mL) was added thereto. The resulting mixture was extracted with dichloromethane (300 mL*2). The organic phases were combined, dried over anhydrous sodium sulfate and filtered. The filtrate was subjected to rotary evaporation to obtain a crude. The crude was purified by flash silica gel column chromatography (petroleum ether:ethyl acetate=1:1 to 0:1) to obtain compound 1c.

Step 4

Compound 1c (4 g, 13.69 mmol) was dissolved in ethyl acetate (25 mL) and methanol (50 mL), and dry Pd/C (0.5 g, 13.69 mmol) was added thereto. The air was replaced with nitrogen twice and hydrogen twice, and finally the reaction solution was stirred at 30° C., 50 psi for 8 hours. The reaction solution was filtered, and the filtrate was subjected to rotary evaporation to obtain product 1d.

$^1$H NMR (400 MHz, DMSO-$d_6$) δ 9.75 (s, 1H), 7.14-7.48 (m, 3H), 6.98 (s, 1H), 6.85 (s, 1H), 6.38 (s, 1H), 5.31 (s, 2H), 2.01 (s, 3H).

Step 5

Tert-butyl nitrite (786.41 mg, 7.63 mmol) was added to a solution of compound 1d (1 g, 3.81 mmol) in acetonitrile (30 mL) at 0° C., and stirred at 0° C. for 30 minutes. Then cuprous bromide (1.09 g, 7.63 mmol) was added thereto, stirred at 25° C. for 30 minutes, and then stirred at 60° C. for 1 hour. To the reaction solution were added water (50 mL) and then ethyl acetate (50 mL*2) for extraction. The organic phases were combined, dried over anhydrous sodium sulfate, and concentrated under reduced pressure to obtain a crude. The crude was separated by silica gel column chromatography (petroleum ether:ethyl acetate=1:1) to obtain compound 1e.

Step 6

To a solution of compound 1e (100 mg, 306.62 μmol) and bis(pinacolato)diboron (116.79 mg, 459.93 μmol) in dioxane (5 mL) were added Pd(dppf)Cl$_2$ (22.44 mg, 30.66 μmol) and KOAc (60.18 mg, 613.24 μmol). The reaction solution was stirred at 100° C. for 3 hours under nitrogen protection. The reaction solution was filtered and subjected to rotary evaporation to obtain crude compound 1f.

LCMS (ESI) m/z: 374.2 [M+1]$^+$

Step 7

To a solution of 6-bromopyrazolo[1,5-a]pyridine (1 g, 5.08 mmol) and 1-methyl-4-pyrazoleboronic acid pinacol ester (1.27 g, 6.09 mmol) in dioxane (30 mL)/H$_2$O (10 mL) were added Pd(dppf)Cl$_2$ (371.36 mg, 507.53 μmol) and K$_3$PO$_4$ (2.15 g, 10.15 mmol). The reaction solution was stirred at 85° C. for 16 hours under nitrogen protection. To the reaction solution were added water (30 mL) and then ethyl acetate (50 mL*3) for extraction. The organic phases were combined, dried over anhydrous sodium sulfate, and concentrated under reduced pressure to obtain a crude. The crude was separated by silica gel column chromatography (petroleum ether:ethyl acetate=1:1) to obtain compound 1g.

LCMS (ESI) m/z: 198.9 [M+1]$^+$

Step 8

To a solution of compound 1g (920 mg, 4.64 mmol) in dichloromethane (30 mL) was added bromosuccinimide (826.06 mg, 4.64 mmol), and the reaction solution was stirred at 20° C. for 16 hours. To the reaction solution were added water (30 mL) and then dichloromethane (30 mL*3) for extraction. The organic phases were combined, dried over anhydrous sodium sulfate, and concentrated under reduced pressure to obtain a crude. The crude was separated by silica gel column chromatography (petroleum ether:ethyl acetate=1:1) to obtain compound 1h.

LCMS (ESI) m/z: 276.8 [M+1]$^+$

Step 9

To a solution of compound 11 (0.4 g, 1.44 mmol) and compound 1f (538.69 mg, 1.44 mmol) in dioxane (10 mL)/H$_2$O (3 mL) were added Pd(dppf)Cl$_2$ (105.62 mg, 144.34 μmol) and K$_3$PO$_4$ (612.78 mg, 2.89 mmol). The reaction solution was stirred at 90° C. for 16 hours under nitrogen protection. To the reaction solution were added water (50 mL) and then ethyl acetate (50 mL*2) for extraction. The organic phases were combined, dried over anhydrous sodium sulfate, and concentrated under reduced pressure to obtain a crude. The crude was separated by silica gel column chromatography (DCM:MeOH=10:1) to obtain a product. 50 mg of the product was purified by preparative high performance liquid chromatography (chromatographic column: Boston Green ODS 150*30 mm*5 μm; mobile phase: [water (0.075% trifluoroacetic acid)-acetonitrile]; B (acetonitrile) %: 43%-73%, 8 min) to obtain compound 3.

LCMS (ESI) m/z: 444.0 [M+1]$^+$ $^1$H NMR (400 MHz, DMSO-$d_6$) δ 10.15 (s, 1H), 9.06 (s, 1H), 8.37 (s, 1H), 8.29 (s, 1H), 8.04 (s, 1H), 7.97 (d, J=8.78 Hz, 2H), 7.58-7.73 (m, 3H), 7.34-7.51 (m, 2H), 7.18-7.27 (m, 1H), 3.89 (s, 3H), 2.10 (s, 3H).

Step 10

HCl (20.40 g, 207.02 mmol, 20 mL, 37% purity) was added to compound 3 (220 mg, 496.11 μmol) in a single-necked bottle, and the reaction solution was stirred at 85° C. for 16 hours. A 4M NaOH solution was added to the reaction solution to adjust the pH to 8, and the mixture was extracted with ethyl acetate (30 mL*3). The organic phases were combined, dried over anhydrous sodium sulfate, and concentrated under reduced pressure to obtain crude 1j without further purification.

LCMS (ESI) m/z: 401.9 [M+1]$^+$

Step 11

To a solution of compound 1j (0.11 g, 274.03 μmol) in pyridine (2.94 g, 37.17 mmol, 3 mL) was added cyclopropylsulfonyl chloride (92.46 mg, 657.68 μmol), and the reaction solution was stirred at 15° C. for 4 hours. To the reaction solution were added acetic acid (6 mL) to adjust the pH to 5, water (10 mL) and then ethyl acetate (10 mL*2) for extraction. The organic phases were combined, dried over anhydrous sodium sulfate, and concentrated under reduced pressure to obtain a crude. The crude was separated by preparative high performance liquid chromatography (chromatographic column: Boston Green ODS 150*30 mm*5 μm; mobile phase: [water (0.075% trifluoroacetic acid)-acetonitrile]; B (acetonitrile) %: 45%-75%, 9 min) to obtain compound 1.

LCMS (ESI) m/z: 506.0 [M+1]$^+$ $^1$H NMR (400 MHz, DMSO-$d_6$) δ 9.94 (s, 1H), 9.07 (s, 1H), 8.40 (s, 1H), 8.29 (s, 1H), 8.04 (s, 1H), 7.95 (d, J=9.04 Hz, 1H), 7.63-7.75 (m, 2H), 7.60 (s, 1H), 7.53 (s, 1H), 7.36-7.45 (m, 1H), 7.30 (s, 1H), 7.24 (br t, J=8.42 Hz, 1H), 3.88 (s, 3H), 2.72-2.81 (m, 1H), 0.93-1.03 (m, 4H).

Example 2

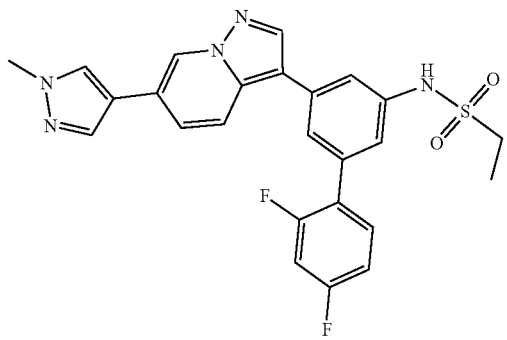 [SMILES: CCS(=O)(=O)Nc1cc(-c2ccc(F)cc2F)cc(-c2cnn3cc(-c4cnn(C)c4)ccc23)c1]

Synthetic Route

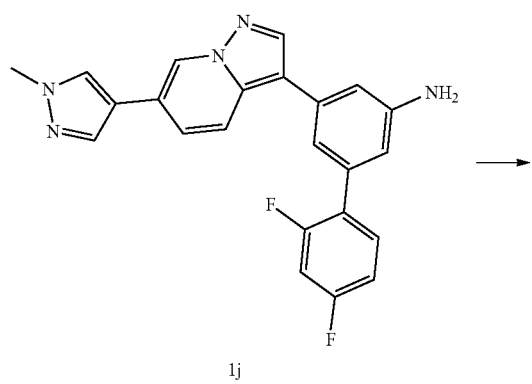

1j

Example 4

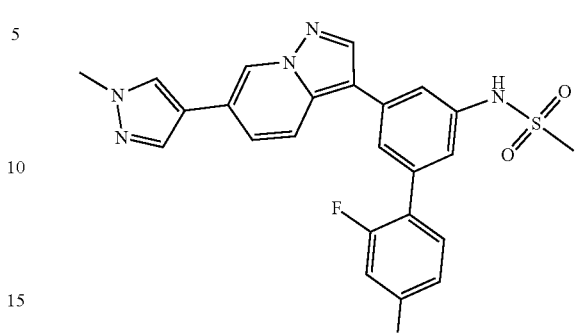

Synthetic Route

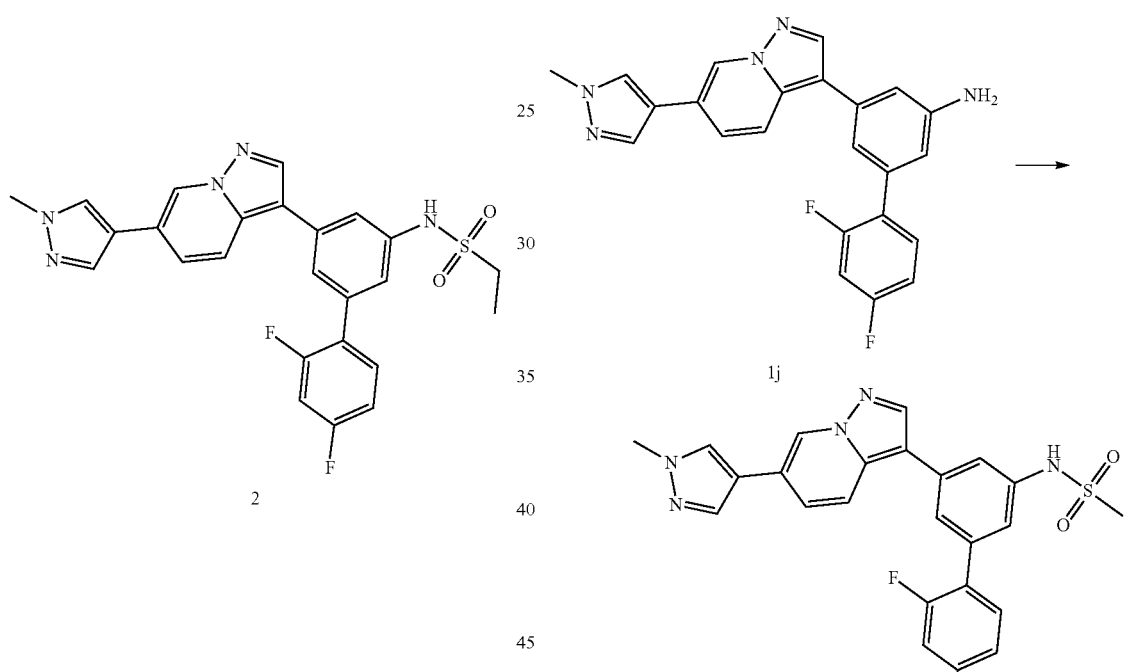

Step 1

To a solution of compound 1j (0.11 g, 274.03 μmol) in pyridine (2 mL) was added ethylsulfonyl chloride (42.28 mg, 328.84 μmol), and the reaction solution was stirred at 15° C. for 16 hours. To the reaction solution were added acetic acid (6 mL) to adjust the pH to 5, water (10 mL) and then ethyl acetate (10 mL*2) for extraction. The organic phases were combined and concentrated under reduced pressure to obtain a crude. The crude was separated by preparative high performance liquid chromatography (chromatographic column: Boston Green ODS 150*30 mm*5 μm; mobile phase: [water (0.075% trifluoroacetic acid)-acetonitrile]; B (acetonitrile) %: 47%-77%, 8 min) to obtain compound 2.

LCMS (ESI) m/z: 493.8 [M+1]$^+$ $^1$H NMR (400 MHz, DMSO-d$_6$) δ 10.00 (s, 1H), 9.07 (s, 1H), 8.40 (s, 1H), 8.29 (s, 1H), 8.05 (s, 1H), 7.95 (d, J=9.30 Hz, 1H), 7.64-7.74 (m, 2H), 7.59 (s, 1H), 7.52 (s, 1H), 7.34-7.45 (m, 1H), 7.19-7.30 (m, 2H), 3.89 (s, 3H), 3.21 (q, J=7.28 Hz, 2H), 1.25 (t, J=7.28 Hz, 3H).

Step 1

To a solution of compound 1j (0.23 g, 572.98 μmol) in pyridine (2 mL) was added methylsufonyl chloride (78.76 mg, 687.58 μmol), and the reaction solution was stirred at 20° C. for 2 hours. To the reaction solution were added acetic acid (10 mL) to adjust the pH to 5, water (10 mL) and then ethyl acetate (15 mL*2) for extraction. The organic phases were combined and concentrated under reduced pressure to obtain a crude. The crude was separated by preparative high performance liquid chromatography (chromatographic column: Boston Green ODS 150*30 mm*5 μm; mobile phase: [water (0.075% trifluoroacetic acid)-acetonitrile]; B (acetonitrile) %: 43%-63%, 12 min) to obtain compound 4.

LCMS (ESI) m/z: 480.0 [M+1]$^+$ $^1$H NMR (400 MHz, DMSO-d$_6$) δ 9.95 (s, 1H), 9.03-9.17 (m, 1H), 9.07 (s, 1H), 8.40 (s, 1H), 8.29 (s, 1H), 8.04 (s, 1H), 7.96 (br d, J=9.30 Hz, 1H), 7.62-7.77 (m, 2H), 7.56 (br d, J=15.32 Hz, 2H), 7.41 (br t, J=10.04 Hz, 1H), 7.20-7.30 (m, 2H), 3.89 (s, 3H), 3.10 (s, 3H)
Example 5
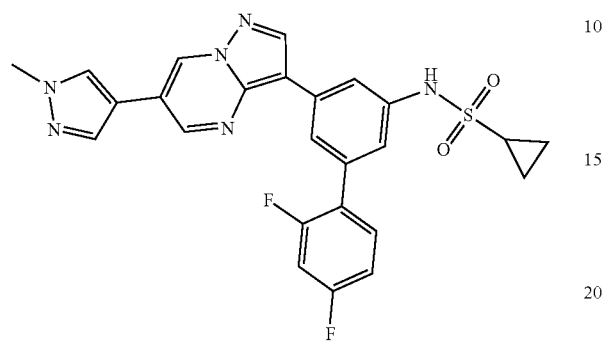
Synthetic Route
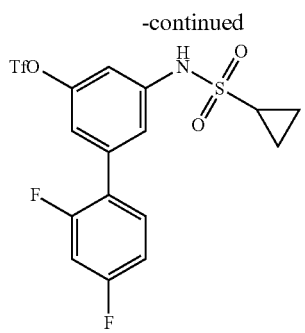
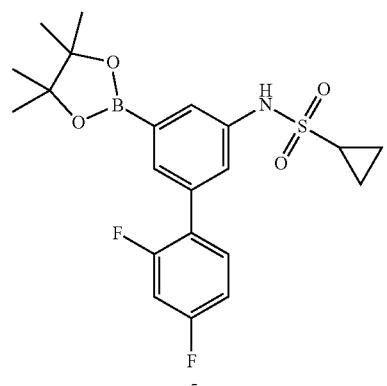
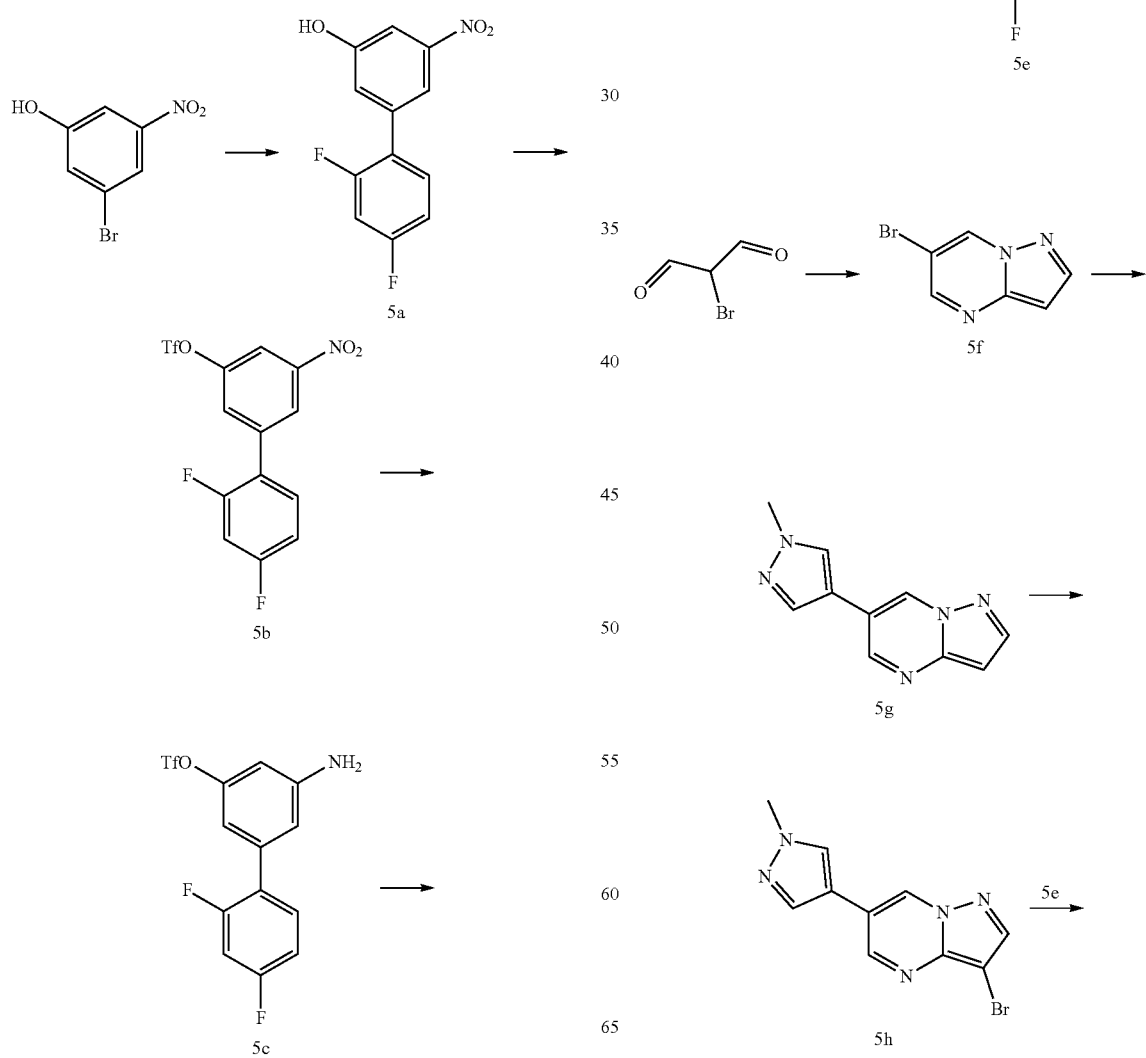

-continued

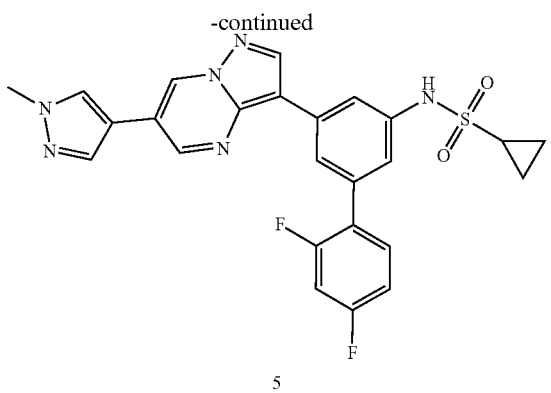

5

Step 1

To a solution of 3-bromo-5-nitro-phenol (10 g, 45.87 mmol) and 2,4-difluorophenylboronic acid (8.69 g, 55.04 mmol) in tetrahydrofuran (100 mL) and water (50 mL) were added Pd(dppf)Cl$_2$ (3.36 g, 4.59 mmol) and potassium phosphate (24.34 g, 114.68 mmol). The reaction solution was stirred at 90° C. for 16 hours under nitrogen protection. To the reaction solution was added water (250 mL), and then ethyl acetate (250 mL*3). The resulting mixture was dried over anhydrous sodium sulfate and filtered. The filtrate was subjected to rotary evaporation to obtain a crude. The crude was purified by flash silica gel column chromatography (petroleum ether:ethyl acetate=5:1) to obtain compound 5a.

$^1$H NMR (400 MHz, DMSO-d$_6$) δ 10.68 (br s, 1H), 7.76 (d, J=1.76 Hz, 1H), 7.62-7.71 (m, 1H), 7.59 (t, J=2.14 Hz, 1H), 7.36-7.47 (m, 1H), 7.32-7.36 (m, 1H), 7.18-7.27 (m, 1H)

Step 2

To a solution of compound 5a (10 g, 39.81 mmol) in DMF (100 mL) were added DIEA (15.44 g, 119.43 mmol, 20.80 mL) and N-phenylbis(trifluoromethanesulfonyl)imide (21.33 g, 59.72 mmol), and the reaction solution was stirred at 20° C. for 16 hours. To the reaction solution was added 500 mL of water and then ethyl acetate (350 mL*2) for extraction. The organic phases were combined, dried over anhydrous sodium sulfate, and filtered. The filtrate was subjected to rotary evaporation to obtain a crude. The crude was purified by flash silica gel column chromatography (PE:EtOAc=3:1) to obtain compound 5b.

Step 3

To a solution of compound 5b (7.5 g, 19.57 mmol) in ethanol (50 mL) and water (10 mL) were added zinc powder (12.80 g, 195.70 mmol) and ammonium chloride (10.47 g, 195.70 mmol), and the reaction solution was stirred at 80° C. for 16 hours. The reaction solution was directly filtered through celite, and the filtrate was concentrated under reduced pressure to obtain crude compound 5c.

LCMS (ESI) m/z: 353.8 [M+1]$^+$

Step 4

To a solution of compound 5c (6.9 g, 19.53 mmol) in pyridine (67.62 g, 854.87 mmol, 69.00 mL) was added cyclopropylsulfonyl chloride (3.30 g, 23.44 mmol), and the reaction solution was stirred at 20° C. for 16 hours. To the reaction solution were added acetic acid (80 mL), water (250 mL) and then ethyl acetate (200 mL*3) for extraction. The organic phases were combined, dried over anhydrous sodium sulfate, and filtered. The filtrate was subjected to rotary evaporation to obtain crude compound 5d.

Step 5

To a solution of compound 5d (8 g, 17.49 mmol) and bis(pinacolato)diboron (4.44 g, 17.49 mmol) in dioxane (80 mL) were added Pd(dppf)Cl$_2$ (1.28 g, 1.75 mmol) and potassium acetate (3.43 g, 34.98 mmol). The reaction solution was stirred at 90° C. for 16 hours under nitrogen protection. The reaction solution was filtered off with suction through celite, and the filtrate was concentrated under reduced pressure to obtain a crude. The crude was purified by flash silica gel column chromatography (PE:EtOAc=3:1) to obtain compound 5e.

Step 6

To a solution of 2-bromomalonaldehyde (15.1 g, 100.03 mmol) in ethanol (120 mL) were added 5-amino-pyrazole (8.31 g, 100.03 mmol) at 0° C., and then HCl (10.13 g, 100.03 mmol, 9.93 mL, 36% purity) at 0° C., and the reaction solution was stirred at 20° C. for 2 hours. The reaction solution was filtered directly, and the filter cake was washed with an aqueous saturated sodium bicarbonate solution (300 mL), and then washed with water (300 mL). The filter cake was azeotropically dried by distilling off toluene and water to obtain compound 5f.

LCMS (ESI) m/z: 197.7 [M+1]$^+$, 199.7 [M+3]$^+$ $^1$H NMR (400 MHz, DMSO-d$_6$) δ 9.60 (dd, J=0.88, 2.14 Hz, 1H), 8.62 (d, J=2.26 Hz, 1H), 8.24 (d, J=2.52 Hz, 1H), 6.80 (dd, J=0.75, 2.26 Hz, 1H)

Step 7

To a solution of compound 5f (2 g, 10.10 mmol) and 1-methyl-4-pyrazoleboronic acid pinacol ester (2.52 g, 12.12 mmol) in tetrahydrofuran (30 mL) and water (10 mL) were added Pd(dppf)Cl$_2$ (739.02 mg, 1.01 mmol) and potassium phosphate (4.29 g, 20.20 mmol). The reaction solution was stirred at 90° C. for 16 hours under nitrogen protection. To the reaction solution were added water (50 mL) and then ethyl acetate (60 mL*3) for extraction. The organic phases were combined, dried over anhydrous sodium sulfate, and filtered. The filtrate was concentrated to obtain a crude. The crude was separated by silica gel column chromatography (petroleum ether:ethyl acetate=0:1) to obtain compound 5g.

LCMS (ESI) m/z: 200.1 [M+1]$^+$ $^1$H NMR (400 MHz, CD$_3$OD) δ 9.02-9.16 (m, 1H), 8.78 (d, J=2.02 Hz, 1H), 8.08-8.16 (m, 2H), 7.96 (s, 1H), 6.69 (d, J=1.76 Hz, 1H), 3.97 (s, 3H).

Step 8

To a solution of compound 5g (200 mg, 1.00 mmol) in dichloromethane (10 mL) was added bromosuccinimide (196.56 mg, 1.10 mmol), and the reaction solution was stirred at 25° C. for 3 hours. To the reaction solution was added 30 mL of water and then dichloromethane (20 mL*2) for extraction. The organic phases were combined, dried over anhydrous sodium sulfate, and filtered. The filtrate was concentrated under reduced pressure to obtain crude compound 5h.

LCMS (ESI) m/z: 277.7 [M+1]$^+$, 279.7 [M+3]$^+$

Step 9

To a solution of compound 5h (100 mg, 359.57 μmol) and compound 5e (187.82 mg, 431.49 μmol) in tetrahydrofuran (10 mL) and water (3.5 mL) were added Pd(dppf)Cl$_2$ (26.31 mg, 35.96 μmol) and potassium phosphate (152.65 mg, 719.15 μmol). The reaction solution was stirred at 90° C. for 16 hours under nitrogen protection. To the reaction solution were added water (20 mL) and then ethyl acetate (25 mL*2) for extraction. The organic phases were combined, dried over anhydrous sodium sulfate, and filtered. The filtrate was concentrated under reduced pressure to obtain a crude. The crude was separated by preparative thin-layer chromatography silica gel plate (PE:EA=0:1) to obtain compound 5.

LCMS (ESI) m/z: 529.0 [M+23]$^+$ $^1$H NMR (400 MHz, DMSO-d$_6$) δ 9.93 (s, 1H), 9.47 (d, J=2.26 Hz, 1H), 9.02 (d, J=2.26 Hz, 1H), 8.72 (s, 1H), 8.38 (s, 1H), 8.08-8.15 (m, 2H), 7.98 (s, 1H), 7.59-7.71 (m, 1H), 7.37-7.47 (m, 1H), 7.22-7.31 (m, 2H), 3.91 (s, 3H), 2.70-2.80 (m, 1H), 0.93-1.06 (m, 4H).

Example 6

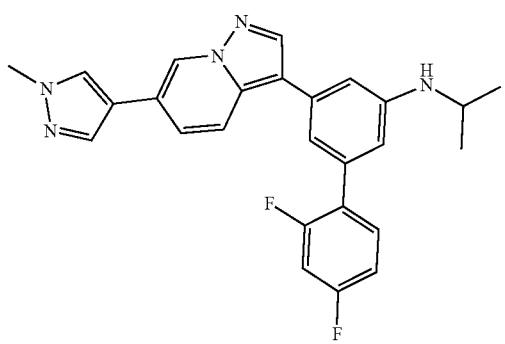 [SMILES: CC(C)Nc1cc(-c2ccc(F)cc2F)cc(-c2cnn3cc(-c4cnn(C)c4)ccc23)c1]

Synthetic Route

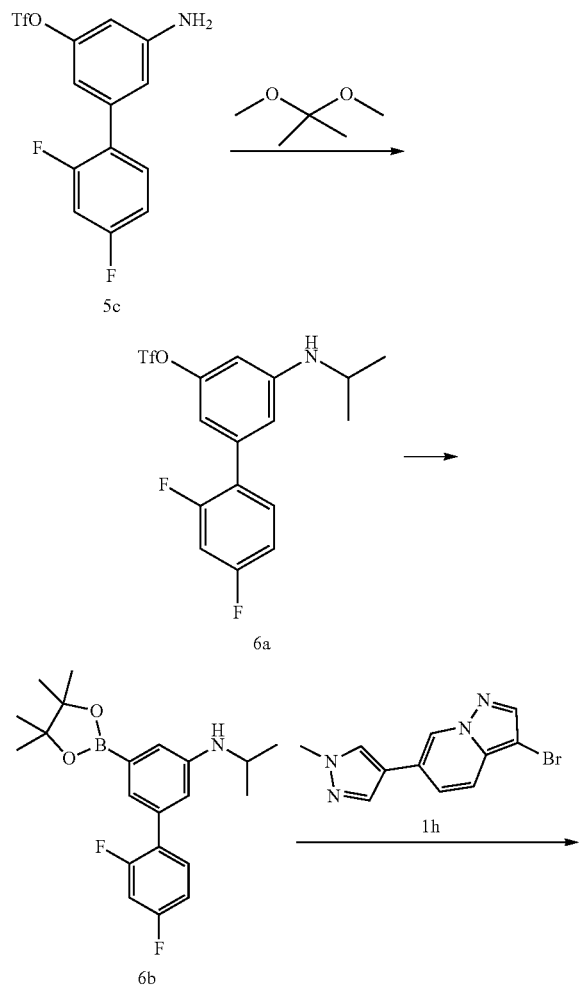

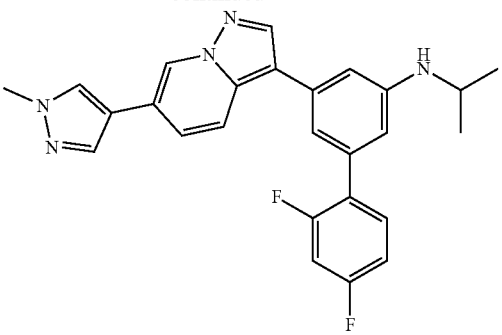

6

Step 1

Compound 5c (2 g, 5.66 mmol) and 2,2-dimethoxypropane (1.18 g, 11.32 mmol, 1.39 mL) were added to 1,2-dichloroethane (30 mL), and then sodium triacetoxyborohydride (3.60 g, 16.98 mmol) and glacial acetic acid (1.02 g, 16.98 mmol, 971.35 μL) were added thereto. The reaction solution was stirred at 25° C. for 2 hours. The reaction solution was subjected to rotary evaporation and purified by column chromatography to obtain compound 6a.

LCMS (ESI) m/z: 396.1 [M+1]$^+$

Step 2

Compound 6a (0.5 g, 1.26 mmol), bis(pinacolato)diboron (481.74 mg, 1.90 mmol), potassium acetate (248.24 mg, 2.53 mmol) and Pd(dppf)Cl$_2$ (92.54 mg, 126.47 μmol) were added to dioxane (10 mL). The air was replaced with nitrogen three times, and then the reaction solution was stirred at 100° C. for 3 hours. To the reaction solution were added ethyl acetate (100 mL) and water (100 mL) for extraction and phase separation. The organic phase was dried, filtered and subjected to rotary evaporation to obtain a crude, which was then purified by column chromatography to obtain compound 6b.

LCMS (ESI) m/z: 374.3 [M+1]$^+$

Step 3

Compound 6b (0.3 g, 803.77 μmol), compound 1h (289.56 mg, 1.04 mmol), potassium phosphate (341.23 mg, 1.61 mmol) and Pd(dppf)Cl$_2$ (58.81 mg, 80.38 μmol) were added to dioxane (10 mL) and water (3 mL). The reaction solution was bubbled with nitrogen, and then stirred for 1 hour at 100° C. under microwave (7 bar) conditions. To the reaction solution were added ethyl acetate (100 mL) and water (100 mL) for extraction and phase separation. The organic phase was dried, filtered and concentrated to obtain a crude. The crude was purified by column and preparative high performance liquid chromatography (chromatographic column: Welch Xtimate C18 150*25 mm*5 μm; mobile phase: [water (10 mM ammonium carbonate)-acetonitrile]; B (acetonitrile) %: 50%-80%, 10.5 min) to obtain compound 6.

LCMS (ESI) m/z: 444.3 [M+1]$^+$ $^1$H NMR (400 MHz, DMSO-d$_6$) δ 9.00-9.08 (m, 1H), 8.24-8.35 (m, 2H), 8.01-8.09 (m, 1H), 7.88-7.97 (m, 1H), 7.53-7.74 (m, 2H), 7.30-7.38 (m, 1H), 7.14-7.26 (m, 1H), 6.87-6.97 (m, 2H), 6.57-6.65 (m, 1H), 5.62-5.72 (m, 1H), 3.82-3.99 (m, 3H), 3.60-3.76 (m, 1H), 1.12-1.31 (m, 6H)

Example 7

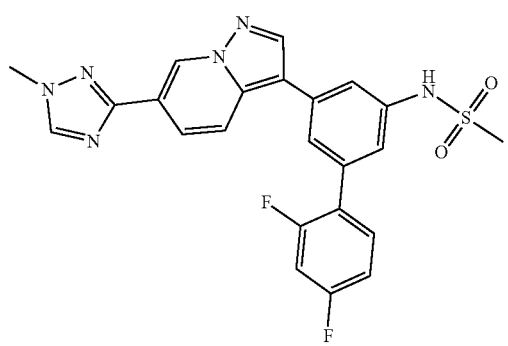

Synthetic Route

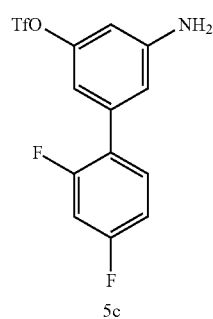

5c

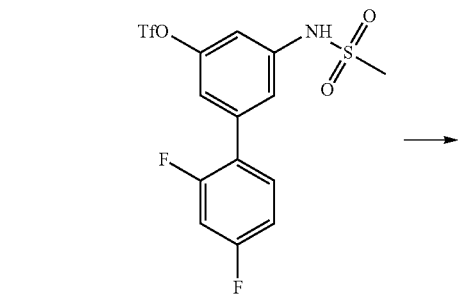

5i

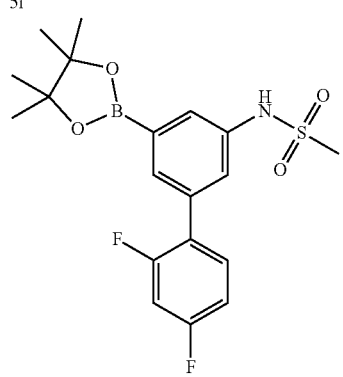

5j

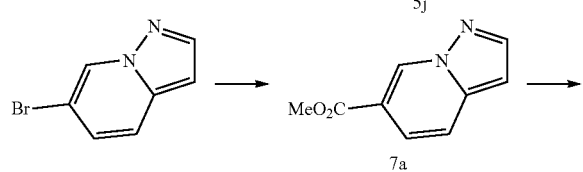

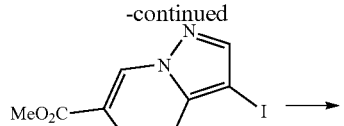

7b

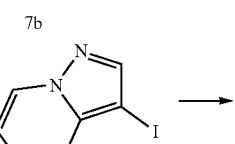

7c

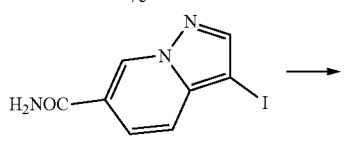

7d

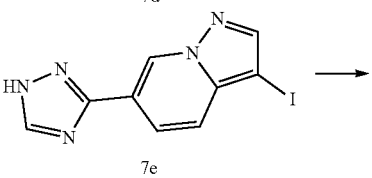

7e

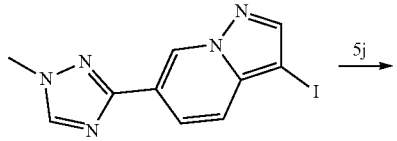

7f

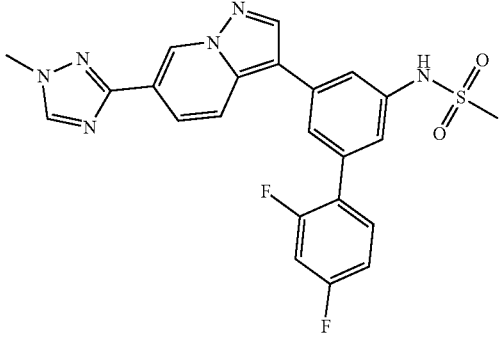

7

Step 1

To a solution of compound 5c (16.5 g, 46.71 mmol) in pyridine (75 mL) was added methylsufonyl chloride (8.03 g, 70.06 mmol), and the reaction solution was stirred at 30° C. for 3 hours. After the reaction was complete, to the reaction solution were added water (100 mL) and then ethyl acetate (80 mL*3) for extraction. The organic phases were combined, dried over anhydrous sodium sulfate, and concentrated under reduced pressure with an oil pump to obtain compound 5i.

Step 2

Compound 5i (11.52 g, 26.7 mmol) and bis(pinacolato) diboron (8.12 g, 31.99 mmol) were dissolved in dioxane (200 mL), and Pd(dppf)Cl₂ (1.95 g, 2.67 mmol) and potassium acetate (5.23 g, 53.32 mmol) were added thereto. The reaction solution was stirred at 100° C. for 16 hours. The reaction solution was filtered through celite, and the filtrate was collected and concentrated under reduced pressure to obtain a crude. The crude was separated by silica gel column chromatography (PE:EtOAc=5:1) to obtain compound 5j.

LCMS (ESI) m/z: 409.13 [M+1]$^+$ $^1$H NMR (400 MHz, DMSO-d$_6$) δ 7.93 (s, 1H), 7.54-7.55 (m, 1H), 7.50 (s, 2H), 7.48-7.46 (m, 1H), 7.33-7.42 (m, 1H), 7.20 (br d, J=2.24 Hz, 1H), 3.01 (s, 3H), 1.26-1.35 (m, 12H).

Step 3

Triethylamine (770.36 mg, 7.61 mmol, 1.06 mL) was added dropwise to a solution of 6-bromopyrazolo[1,5-a]pyridine (0.5 g, 2.54 mmol), palladium acetate (113.94 mg, 507.53 μmol) and 1,1'-bis(diphenylphosphine)ferrocene (281.36 mg, 507.53 μmol) in methanol (5 mL)/dioxane (5 mL). The reaction solution was then heated to 70° C. and reacted for 12 hours under 50 psi carbon monoxide. The reaction solution was cooled to room temperature and filtered. The filtrate was concentrated and purified by column chromatography to obtain compound 7a.

LCMS (ESI) m/z: 177.1 [M+1]$^+$

Step 4

N-iodosuccinimide (646.20 mg, 2.87 mmol) was added to a solution of compound 7a (0.44 g, 2.50 mmol) in dry N,N-dimethylformamide (6 mL), and the reaction solution was stirred at 25° C. for 1 hour under nitrogen protection. The reaction solution was quenched with sodium thiosulfate/a saturated sodium bicarbonate solution (1:1, 30 mL). The reaction solution was stirred at 25° C. for 15 minutes, and then extracted with ethyl acetate/water (30 mL/20 mL) for phase separation. The organic phase was washed with water (30 mL) and saturated brine (30 mL), dried over anhydrous sodium sulfate, filtered and concentrated to obtain a crude, which was purified by column chromatography to obtain compound 7b.

LCMS (ESI) m/z: 303.0 [M+1]$^+$

Step 5

Lithium hydroxide monohydrate (138.92 mg, 3.31 mmol) was added to a solution of compound 7b (500 mg, 1.66 mmol) in methanol (2 mL)/tetrahydrofuran (2 mL)/water (2 mL), and the reaction solution was stirred at 25° C. for 12 hours. The reaction solution was concentrated and adjusted to pH 4 with 0.2 M HCl, and then extracted with ethyl acetate/water (30 mL/20 mL) for phase separation. The organic phase was washed with brine (30 mL), dried over anhydrous sodium sulfate, filtered and concentrated to obtain compound 7c.

LCMS (ESI) m/z: 288.9 [M+1]$^+$

Step 6

Compound 7c (0.42 g, 1.46 mmol) was added to tetrahydrofuran (5 mL), and the reaction solution was cooled to 0° C. Oxalyl chloride (370.15 mg, 2.92 mmol, 255.27 μL) and N,N-dimethylformamide (21.32 mg, 291.62 μmol, 22.44 μL) were added dropwise thereto, and the reaction solution was stirred for 0.5 hour and subjected to rotary evaporation after the reaction was complete. Ammonia gas (880.90 mg, 51.73 mmol) was introduced into THF (5 mL) at −78° C. The reaction solution with gas was added dropwise to the concentrated and dried crude at 0° C., and the reaction solution was reacted at 25° C. for 0.5 hour. The reaction solution was concentrated to dryness and used directly in the next step without purification to obtain compound 7d.

LCMS (ESI) m/z: 288.0 [M+1]$^+$

Step 7

A mixture of compound 7d (0.4 g, 1.39 mmol) and N,N-dimethylformamide dimethylacetal (3.32 g, 27.87 mmol, 3.70 mL) was heated to 95° C., and stirred for 28 minutes to obtain a clear solution. The reaction solution was cooled to 25° C., and 1,2-dichloroethane (5 mL) was added thereto, so that the reaction solution was concentrated to remove excess N,N-dimethylformamide dimethylacetal. The obtained crude was dissolved in the prepared ice ethanol solution. Ethanol (5 mL) and glacial acetic acid (1.5 mL) were added to a bottle, and cooled to 0° C. Hydrazine hydrate (697.56 mg, 13.93 mmol, 677.25 μL) was added dropwise to the bottle, and after 2 minutes, a crude solution of N,N-dimethylformamide dimethylacetal in ice ethanol was added thereto. The reaction solution was warmed to 25° C. and stirred for 2 hours. The reaction solution was concentrated without purification to obtain compound 7e.

LCMS (ESI) m/z: 312.0 [M+1]$^+$

Step 8

Compound 7e (0.09 g, 289.31 μmol) and potassium carbonate (119.95 mg, 867.94 μmol) were added to N,N-dimethylformamide (3 mL). The reaction solution was cooled to 0° C., and after 5 minutes, methyl iodide (55.44 mg, 390.57 μmol, 24.31 μL) and N,N-dimethylformamide (1 mL) were added dropwise thereto. After the dropwise addition was complete, the reaction solution was slowly warmed to 25° C. and reacted for 2 hours and 20 minutes. To the reaction solution was added 20 mL of 5% aqueous ammonia, and the mixture was extracted with ethyl acetate (10 mL*2). The combined organic phase was washed with 20 mL saturated brine, dried over anhydrous sodium sulfate, and filtered. Then the organic phase was concentrated to obtain a crude, which was purified by preparative thin-layer chromatography silica gel plate to obtain compound 7f.

LCMS (ESI) m/z: 325.9, 326.8[M+1]$^+$

Step 9

Compound 7f (25 mg, 76.90 μmol), compound 5j (56.65 mg, 138.42 μmol), potassium phosphate (32.65 mg, 153.80 μmol) and Pd(dppf)Cl$_2$ (5.63 mg, 7.69 μmol) were added to water (1 mL) and dioxane (3 mL). The reaction solution was bubbled with nitrogen, and then stirred for 30 minutes at 100° C. under microwave (2 bar) conditions. To the reaction solution were added water (100 mL) and ethyl acetate (100 mL) for extraction and phase separation. The organic phase was dried, filtered and concentrated to obtain a crude. The crude was purified by preparative thin-layer chromatography silica gel plate (using ethyl acetate as a developing solvent) to obtain compound 7.

LCMS (ESI) m/z: 481.1 [M+1]$^+$ $^1$H NMR (400 MHz, DMSO-d$_6$) δ 9.06-9.10 (m, 1H), 8.54-8.59 (m, 1H), 8.39-8.54 (m, 1H), 7.96-8.03 (m, 1H), 7.70-7.90 (m, 2H), 7.59-7.66 (m, 1H), 7.41-7.47 (m, 1H), 7.29-7.38 (m, 2H), 7.13-7.24 (m, 2H), 3.88-3.95 (m, 3H) 2.90-2.98 (m, 3H).

Example 8

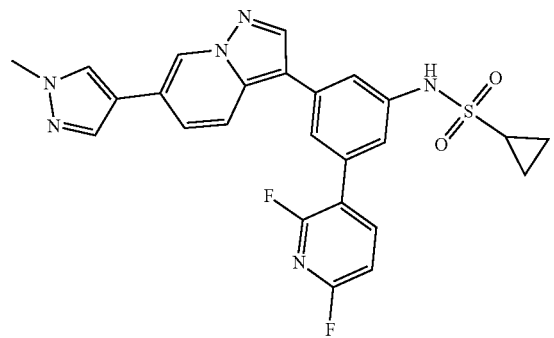 [SMILES: Cn1cc(-c2ccc3c(-c4cc(NS(=O)(=O)C5CC5)cc(-c5ccc(F)nc5F)c4)cnn3c2)cn1]

Synthetic Route

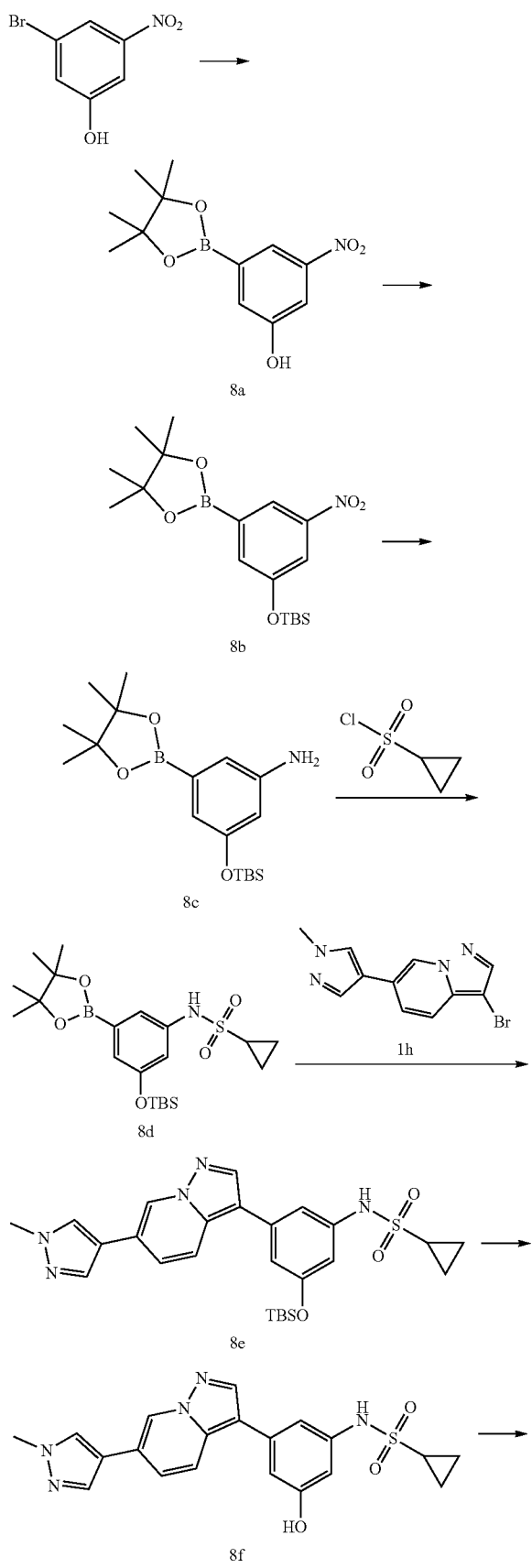

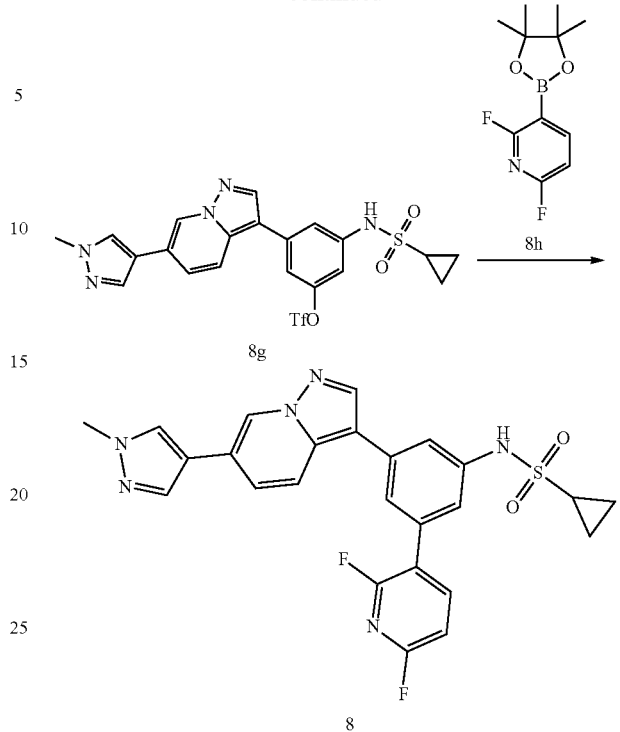

Step 1

3-bromo-5-nitro-phenol (20 g, 91.74 mmol) and bis(pinacolato)diboron (25.63 g, 100.92 mmol) were dissolved in dioxane (200 mL), and KOAc (18.01 g, 183.48 mmol) and Pd(dppf)Cl$_2$ (3.36 g, 4.59 mmol) were added thereto. The reaction solution was stirred at 90° C. for 16 hours under nitrogen protection. The reaction solution was directly filtered through celite, and the filter cake was washed twice with ethyl acetate. The filtrate was collected and subjected to rotary evaporation to obtain a crude. The crude was purified by column chromatography with PE/EtOAc=5/1 to obtain compound 8a.

$^1$H NMR (400 MHz, CDCl$_3$) δ 8.17 (d, J=1.52 Hz, 1H), 7.76 (t, J=2.26 Hz, 1H), 7.57 (d, J=2.02 Hz, 1H), 7.00 (br s, 1H), 1.35 (s, 12H).

Step 2

Compound 8a (3 g, 11.32 mmol) and dimethyl tert-butylchlorosilane (2.05 g, 13.58 mmol, 1.66 mL) were dissolved in DMF (30 mL), and imidazole (1.93 g, 28.29 mmol) and 4-N,N-dimethylaminopyridine (138.27 mg, 1.13 mmol) were added thereto. The reaction solution was stirred at room temperature 30° C. for 16 hours. The reaction solution was extracted with 3 mL of water, and the organic phase was collected, dried over anhydrous sodium sulfate, and subjected to rotary evaporation to obtain compound 8b.

$^1$H NMR (400 MHz, DMSO-d$_6$) δ 8.01 (d, J=1.24 Hz, 1H), 7.69 (t, J=2.12 Hz, 1H), 7.45 (d, J=1.52 Hz, 1H), 1.32 (s, 12H), 0.98 (s, 9H), 0.24 (s, 6H).

Step 3

Compound 8b (2.8 g, 7.38 mmol) was dissolved in ethanol (120 mL) and water (20 mL), and ammonium chloride (3.95 g, 73.81 mmol) and zinc powder (4.83 g, 73.81 mmol) were added thereto. The reaction solution was stirred at room temperature 30° C. for 16 hours. The reaction solution was directly filtered. The filter cake was washed twice with absolute ethanol, and the filtrate was subjected to rotary evaporation to obtain a crude. The crude was purified by column chromatography with PE/EtOAc=5/1 to obtain compound 8c.

LCMS (ESI) m/z: 350.0 [M+1]+

Step 4

Compound 8c (1.9 g, 5.44 mmol) was dissolved in pyridine (5 mL), and cyclopropylsulfonyl chloride (917.55 mg, 6.53 mmol) was added thereto. The reaction solution was stirred at 30° C. for 16 hours. To the reaction solution were added 10 mL of water and then 15 mL of ethyl acetate for extraction. The organic phase was washed twice with 10 mL of water, dried over anhydrous sodium sulfate, and subjected to rotary evaporation to obtain a crude. The crude was purified by column chromatography with PE/EtOAc=5/1 to 1/1 to obtain compound 8d.

LCMS (ESI) m/z: 454.1 [M+1]+

Step 5

Compound 8d (500 mg, 1.10 mmol) and compound 1h (203.70 mg, 735.07 μmol) were dissolved in water (5 mL) and tetrahydrofuran (2.5 mL), and potassium phosphate (312.06 mg, 1.47 mmol) and Pd(dppf)Cl$_2$ (53.79 mg, 73.51 μmol) were added thereto. The reaction solution was stirred at 90° C. for 0.5 hour under microwave and nitrogen protection. The reaction solution was extracted twice with 8 mL of water and 8 mL of ethyl acetate, and the organic phase was dried over anhydrous sodium sulfate and subjected to rotary evaporation to obtain a crude. The crude was purified by column chromatography with PE/EtOAc=1/1 to 0/1 to obtain compound 8e.

LCMS (ESI) m/z: 524.1 [M+1]+

Step 6

Compound 8e (10 mg, 19.09 μmol) was dissolved in EtOAc (0.5 mL), and HCl/EtOAc (4 M, 250.00 μL) was added thereto. The reaction solution was stirred at room temperature 30° C. for 16 hours. The reaction solution was directly subjected to rotary evaporation to obtain a crude, which was not purified to obtain compound 8f directly.

LCMS (ESI) m/z: 409.9 [M+1]+

Step 7

Compound 8f (20 mg, 48.84 μmol) was dissolved in DMF (2 mL), and DIEA (25.25 mg, 195.38 μmol, 34.03 μL) and N-phenylbis(trifluoromethanesulfonyl)imide (26.17 mg, 73.27 μmol) were added thereto. The reaction solution was stirred at room temperature 30° C. for 1 hour. The reaction solution was extracted with 2 mL of water and 2 mL of ethyl acetate, and the organic phase was washed 3 times with 2 mL of water and subjected to rotary evaporation to obtain a crude, which was not purified to obtain compound 8g directly.

LCMS (ESI) m/z: 542.0 [M+1]+

Step 8

Compound 8g (20 mg, 36.93 μmol) and compound 8h (13.35 mg, 55.40 μmol) were dissolved in dioxane (1 mL) and water (0.5 mL), and Pd(dppf)Cl$_2$ (2.70 mg, 3.69 μmol) and potassium phosphate (15.68 mg, 73.87 μmol) were added thereto. The reaction solution was stirred at 90° C. for 16 hours under nitrogen protection. The reaction solution was extracted with 2 mL of water and 2 mL of ethyl acetate, and the organic phase was dried over anhydrous sodium sulfate and subjected to rotary evaporation to obtain a crude. The crude was dissolved in methanol and purified by preparative high performance liquid chromatography (chromatographic column: Phenomenex Gemini-NX 80*40 mm*3 μm; mobile phase: [water (0.05% aqueous ammonia+ 10 mM ammonium bicarbonate)-acetonitrile]; B (acetonitrile) %: 42%-58%, 8 min) to obtain compound 8.

LCMS (ESI) m/z: 507.0 [M+1]+

$^1$H NMR (400 MHz, CD$_3$OD) δ 8.83-8.85 (m, 1H), 8.28-8.32 (m, 2H), 8.10-8.13 (m, 1H), 7.97-8.02 (m, 1H), 7.96 (s, 1H), 7.69 (s, 1H), 7.64 (br d, J=7.78 Hz, 3H), 7.42 (s, 1H), 7.14 (s, 1H), 3.99 (s, 3H), 2.69 (s, 1H), 1.13 (br s, 2H), 1.03 (br d, J=8.04 Hz, 2H).

The compounds in Table 1 can be prepared by referring to the steps and methods similar to those in the route for the aforementioned example 8. Particularly, in the process of synthesizing compound 33, cyclopropylsulfonyl chloride was replaced with intermediate 33a in the steps of synthesizing 8c to 8d, and intermediate 8h was replaced with intermediate 33b in the last step to synthesize compound 33 by referring to the synthetic route of example 8. The trifluoroacetate salt of the obtained compound was added to a sodium bicarbonate solution, and extracted with ethyl acetate. The organic phase was dried over anhydrous sodium sulfate, and concentrated under reduced pressure to obtain the compound.

TABLE 1

| Product no. | Product structure | Raw material A | Product LCMS m/z: [M + 1]+ | Product $^1$H NMR |
|---|---|---|---|---|
| Example 9 | 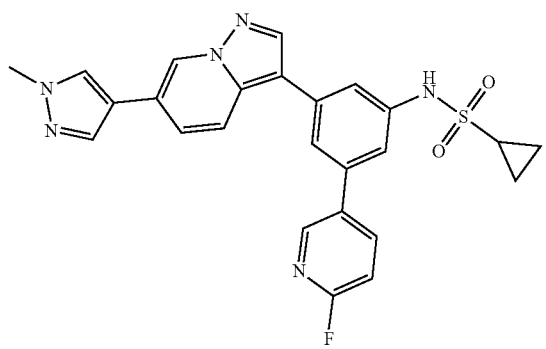 [SMILES: Cn1cc(-c2ccc3c(-c4cc(NS(=O)(=O)C5CC5)cc(-c5ccc(F)nc5)c4)cnn3c2)cn1] | 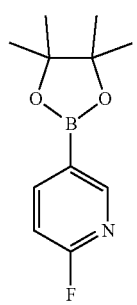 | 489.0 | Trifluoroacetate salt of compound 9: $^1$H NMR (400 MHz, CD$_3$OD) δ 8.68-8.73 (m, 1H), 8.43 (d, J = 2.02 Hz, 1H), 8.14-8.24 (m, 2H), 7.99 (s, 1H), 7.89 (d, J = 9.28 Hz, 1H), 7.83 (s, 1H), 7.57 (d, J = 1.52 Hz, 2H), 7.44-7.54 (m, 2H), 7.32 (s, 1H), 7.11 (dd, J = 2.38, 8.42 Hz, 1H), 3.87 (s, 3H), 2.54-2.64 (m, 1H), 0.99-1.05 (m, 2H), 0.88-0.95 (m, 2H). |

TABLE 1-continued
| Product no. | Product structure | Raw material A | Product LCMS m/z: [M + 1]+ | Product 1H NMR |
|---|---|---|---|---|
| Example 10 | | | 489.0 | Trifluoroacetate salt of compound 10: $^1$H NMR (400 MHz, CD$_3$OD) δ 8.82-8.85 (m, 1H), 8.29-8.31 (m, 1H), 8.24-8.27 (m, 1H), 8.15-8.21 (m, 1H), 8.10-8.13 (m, 1H), 7.98-8.03 (m, 1H), 7.94-7.97 (m, 1H), 7.68-7.72 (m, 1H), 7.64-7.68 (m, 2H), 7.46-7.51 (m, 1H), 7.43-7.46 (m, 1H), 3.99 (s, 3H), 1.62 (br s, 1H), 1.13 (br s, 2H), 1.01-1.07 (m, 2H). |
| Example 33 | | 33a 33b | 495.0 | Trifluoroacetate salt of compound 33: $^1$H NMR (400 MHz, CD$_3$OD) δ 8.79 (s, 1H), 8.54 (d, J = 4.0 Hz, 1H), 8.24 (s, 1H), 8.09 (s, 1H), 7.90-7.97 (m, 3H), 7.71-7.77 (m, 2H), 7.67 (s, 1H), 7.59 (d, J = 8.0 Hz, 1H), 3.97 (s, 3H), 3.20-3.26 (m, 2H), 1.39 (t, J = 8.0 Hz, 3H). |
Example 11
Synthetic Route
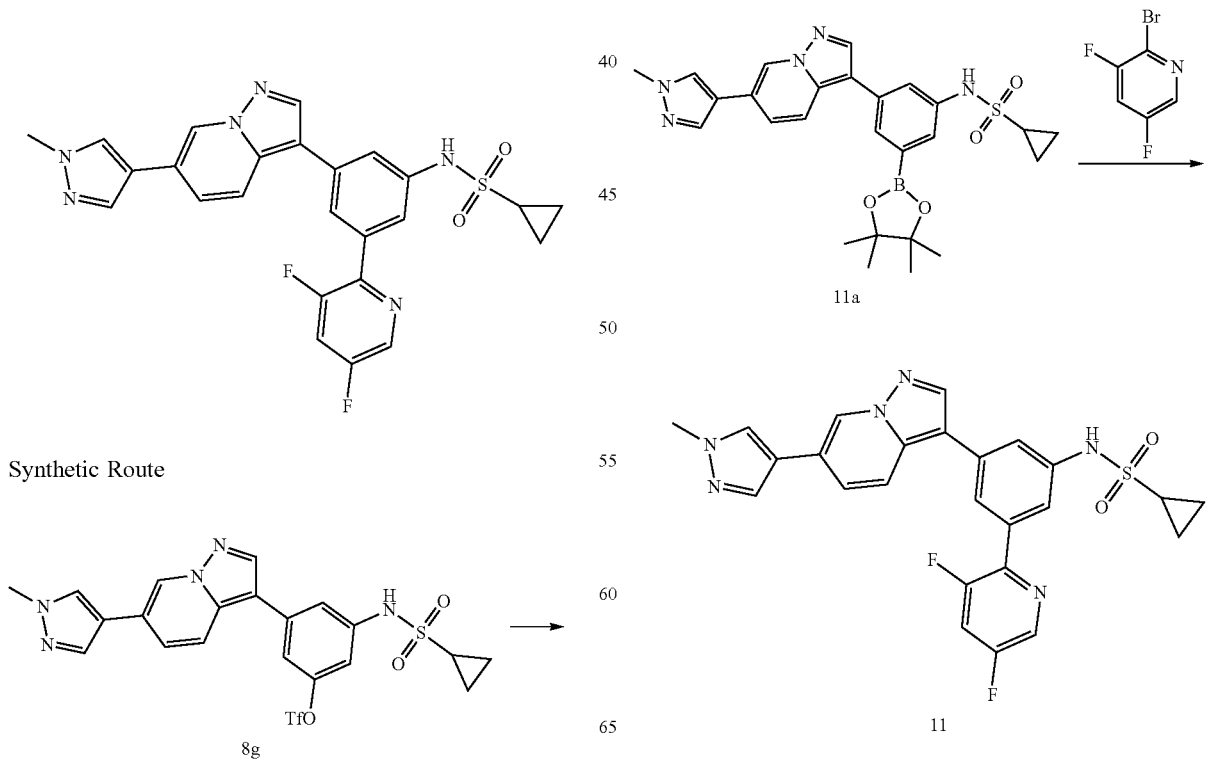

Compound 8g (90 mg, 166.20 μmol) and bis(pinacolato)diboron (50.64 mg, 199.44 μmol) were dissolved in dioxane (1.5 mL), and Pd(dppf)Cl₂ (12.16 mg, 16.62 μmol) and KOAc (48.93 mg, 498.59 μmol) were added thereto. The reaction solution was stirred at 90° C. for 16 hours under nitrogen protection. The reaction solution was directly filtered, and the filtrate was subjected to rotary evaporation to obtain a crude. The crude was purified by preparative thin-layer chromatography silica gel plate to obtain compound 11a.

LCMS (ESI) m/z: 520.1 [M+1]⁺

Step 2

Compound 11a (70 mg, 134.77 μmol) and 2-bromo-3,5-difluoro-pyridine (17.43 mg, 89.84 μmol) were dissolved in dioxane (2 mL) and water (1 mL), and Pd(dppf)Cl₂ (6.57 mg, 8.98 μmol) and potassium sulfate (38.14 mg, 179.69 μmol) were added thereto. The reaction solution was stirred at 90° C. for 16 hours under nitrogen protection. To the reaction solution were added 4 mL of water and then 4 mL of ethyl acetate for extraction. The organic phase was dried over anhydrous sodium sulfate and subjected to rotary evaporation to obtain a crude. The crude was purified by preparative high performance liquid chromatography (chromatographic column: Boston Green ODS 150*30 mm*5 μm; mobile phase: [water (0.075% trifluoroacetic acid)-acetonitrile]; B (acetonitrile) %: 40%-70%, 8 min) to obtain the trifluoroacetate salt of compound 11.

LCMS (ESI) m/z: 507.0 [M+1]⁺

¹H NMR (400 MHz, CD₃OD) δ 8.83 (s, 1H), 8.55 (d, J=2.26 Hz, 1H), 8.28 (s, 1H), 8.12 (s, 1H), 8.00 (d, J=9.54 Hz, 1H), 7.96 (s, 2H), 7.75-7.80 (m, 2H), 7.71 (s, 1H), 7.63 (br d, J=8.28 Hz, 1H), 3.99 (s, 3H), 2.66-2.72 (m, 1H), 1.13 (br s, 2H), 0.98-1.06 (m, 2H).

The trifluoroacetate salt of compound 11 was added to a sodium bicarbonate solution, and extracted with ethyl acetate. The organic phase was dried over anhydrous sodium sulfate and concentrated under reduced pressure to obtain compound 11.

Example 12

Synthetic Route

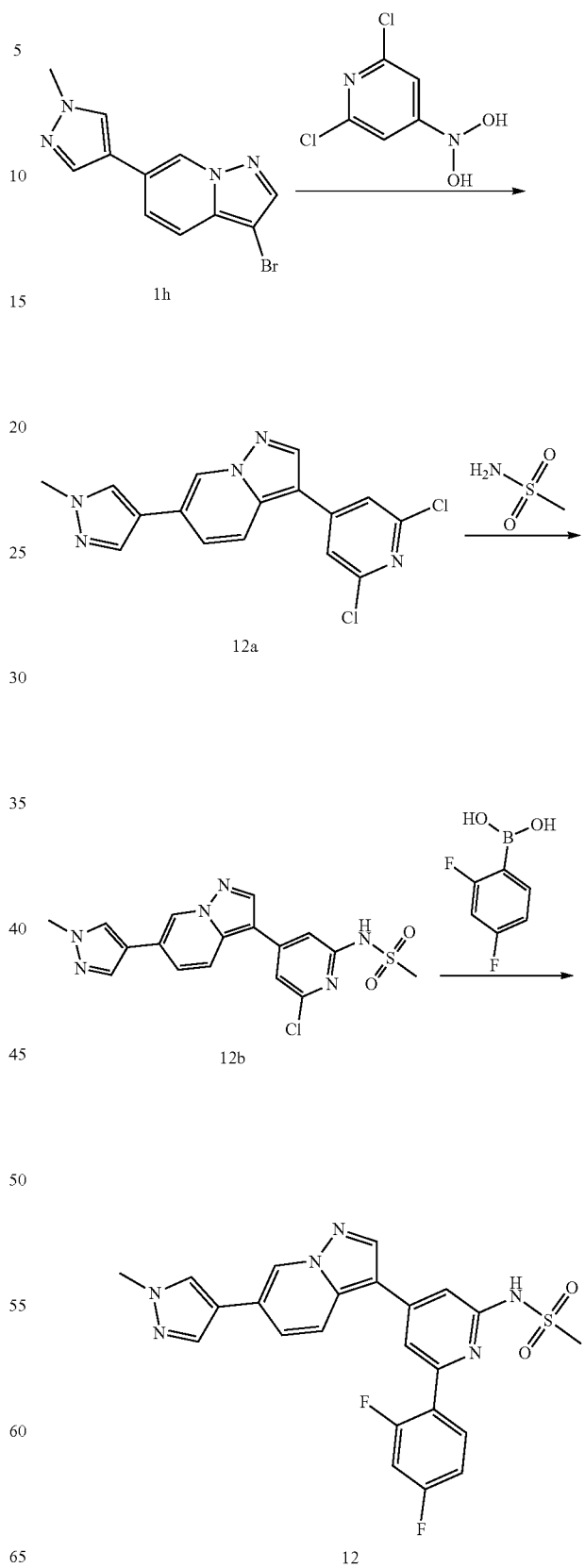

Step 1

Compound 1h (2 g, 7.22 mmol) and (2,6-dichloro-4-pyridine)boronic acid (1.66 g, 8.66 mmol) were dissolved in dioxane (20 mL) and water (10 mL), and Pd(dppf)Cl$_2$ (528.08 mg, 721.71 μmol) and potassium phosphate (3.06 g, 14.43 mmol) were added thereto. The reaction solution was stirred at 90° C. for 16 hours under nitrogen protection. To the reaction solution were added 30 mL of water and then 30 mL of ethyl acetate for extraction. The organic phase was dried over anhydrous sodium sulfate and subjected to rotary evaporation to obtain a crude. The crude was purified by column chromatography with PE/EtOAc=0/1 to obtain compound 12a.

LCMS (ESI) m/z: 343.8 [M+1]$^+$

Step 2

Compound 12a (250 mg, 726.33 μmol) and methylsulfonamide (69.09 mg, 726.33 μmol) were dissolved in dioxane (1.5 mL), and potassium acetate (16.31 mg, 72.63 μmol), 4,5-bisdiphenylphosphino-9,9-dimethylxanthene (84.05 mg, 145.27 μmol, 0.2 eq) and cesium carbonate (709.95 mg, 2.18 mmol) were added thereto. The reaction solution was stirred at 120° C. for 1 hour under microwave and nitrogen protection. The reaction solution was directly filtered, and the filtrate was subjected to rotary evaporation to obtain a crude. The crude was purified by column chromatography with PE/EtOAc=0/1 to obtain compound 12b.

LCMS (ESI) m/z: 402.9 [M+1]$^+$

Step 3

Example 12b (60 mg, 148.94 μmol) and (2,4-difluoro)phenylboronic acid (28.22 mg, 178.72 μmol) were dissolved in dioxane (1.5 mL) and water (0.7 mL), and Pd(dppf)Cl$_2$ (10.90 mg, 14.89 μmol) and potassium phosphate (63.23 mg, 297.87 μmol) were added thereto. The reaction solution was stirred at 90° C. for 16 hours under nitrogen protection. To the reaction solution were added 2 mL of water and then 2 mL of ethyl acetate for extraction. The organic phase was subjected to rotary evaporation to obtain a crude, and the crude was purified by preparative high performance liquid chromatography (chromatographic column: Welch Xtimate C18 150*25 mm*5 μm; mobile phase: [water (0.05% aqueous ammonia)-acetonitrile]; B (acetonitrile) %: 15%-45%, 8.5 min) to obtain compound 12.

LCMS (ESI) m/z: 481.0 [M+1]$^+$ $^1$H NMR (400 MHz, CD$_3$OD): δ 8.62-8.66 (m, 1H), 8.13-8.18 (m, 1H), 8.01 (br s, 1H), 7.90-7.94 (m, 1H), 7.81-7.87 (m, 1H), 7.74-7.77 (m, 1H), 7.44-7.48 (m, 1H), 7.33 (br s, 1H), 7.14 (br d, J=5.3 Hz, 1H), 6.89 (br d, J=9.0 Hz, 3H), 3.78 (s, 3H), 3.08 (br s, 3H).

The compounds in Table 2 can be prepared by referring to the steps and methods similar to those in the route for the aforementioned example 12.

TABLE 2

| Product no. | Product structure | Raw material A | Product LCMS m/z: [M + 1]$^+$ | Product $^1$H NMR |
| --- | --- | --- | --- | --- |
| Example 13 | | | 495.0 | Compound 13: $^1$H NMR (400 MHz, CD$_3$OD) δ 8.83 (s, 1H), 8.35 (s, 1H), 8.11-8.17 (m, 1H), 8.10 (s, 1H), 8.02 (d, J = 9.30 Hz, 1H), 7.94 (s, 1H), 7.66 (d, J = 10.54 Hz, 1H), 7.59 (s, 1H), 7.19 (s, 1H), 7.04-7.12 (m, 2H), 3.97 (s, 3H), 3.52 (d, J = 7.53 Hz, 2H), 1.38 (t, J = 7.28 Hz, 3H). |
| Example 14 | | | 507.3 | Compound 14: $^1$H NMR (400 MHz, DMSO-d$_6$) δ 9.15 (s, 1H), 8.57 (s, 1H), 8.33 (s, 1H), 7.96-8.11 (m, 3H), 7.69-7.83 (m, 2H), 7.38-7.48 (m, 1H), 7.24-7.34 (m, 2H), 3.20 (br s, 1H), 1.11 (br s, 2H), 1.05 (br d, J = 7.28 Hz, 2H). |

Example 15

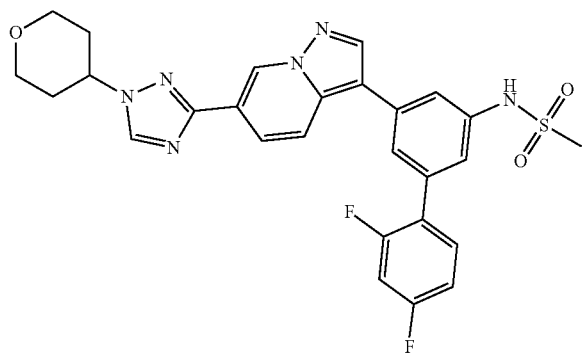 [SMILES: CS(=O)(=O)Nc1cc(-c2ccc(F)cc2F)cc(-c2cnn3cc(-c4ncn(C5CCOCC5)n4)ccc23)c1]

Synthetic Route

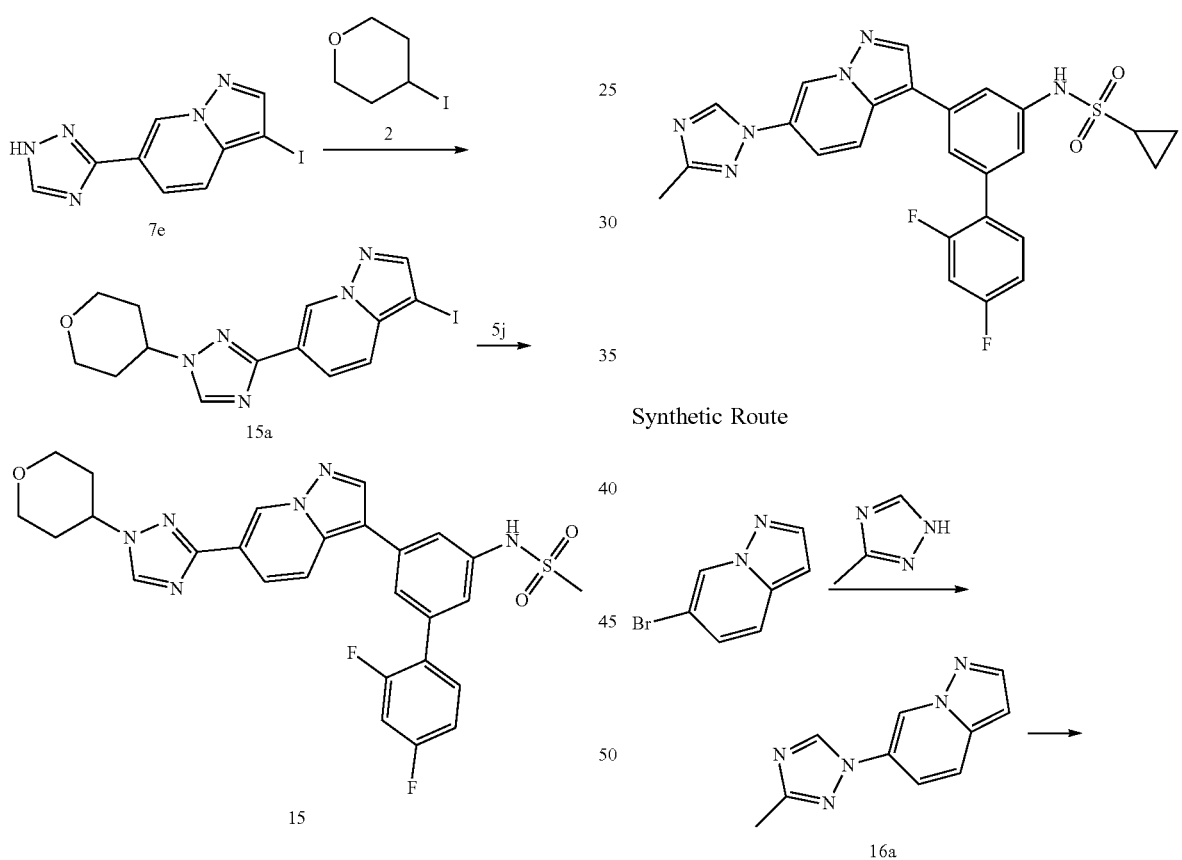

Step 1

Compound 7e (30 mg, 96.44 μmol), 4-iodotetrahydropyran (24.54 mg, 115.73 μmol) and potassium carbonate (39.99 mg, 289.31 μmol) were heated to N,N-dimethylformamide (1 mL), and the reaction solution was stirred at 25° C. for 1 hour. To the reaction solution were added water (10 mL) and ethyl acetate (10 mL) for extraction and phase separation. The organic phase was dried, filtered and concentrated to obtain compound 15a.

LCMS (ESI) m/z: 396.1, 397.1[M+1]$^+$

Step 2

Compound 15a (30 mg, 75.91 μmol), compound 5j (37.28 mg, 91.09 μmol), potassium phosphate (48.34 mg, 227.73 μmol) and Pd(dppf)Cl$_2$ (5.55 mg, 7.59 μmol) were added to dioxane (2 mL) and water (0.5 mL). The air was replaced with nitrogen three times, and then the reaction solution was stirred at 100° C. for 2 hours. To the reaction solution were added water (10 mL) and ethyl acetate (10 mL) for extraction and phase separation. The organic phase was dried, filtered and concentrated to obtain a crude, which was purified by preparative thin-layer chromatography silica gel plate to obtain compound 15.

LCMS (ESI) m/z: 551.2 [M+1]$^+$ $^1$H NMR (400 MHz, DMSO-d$_6$) δ 9.98 (s, 1H), 9.13 (s, 1H), 8.74 (s, 1H), 8.45 (s, 1H), 8.03 (s, 1H), 7.89 (s, 1H), 7.67 (s, 1H), 7.31-7.46 (m, 3H), 7.16-7.25 (m, 2H), 4.62 (s, 1H), 3.92-4.06 (m, 2H), 3.50 (m, 2H), 2.95 (s, 3H), 1.97-2.14 (m, 4H).

Example 16

Synthetic Route

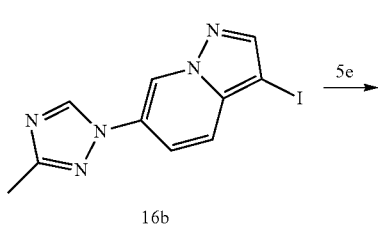

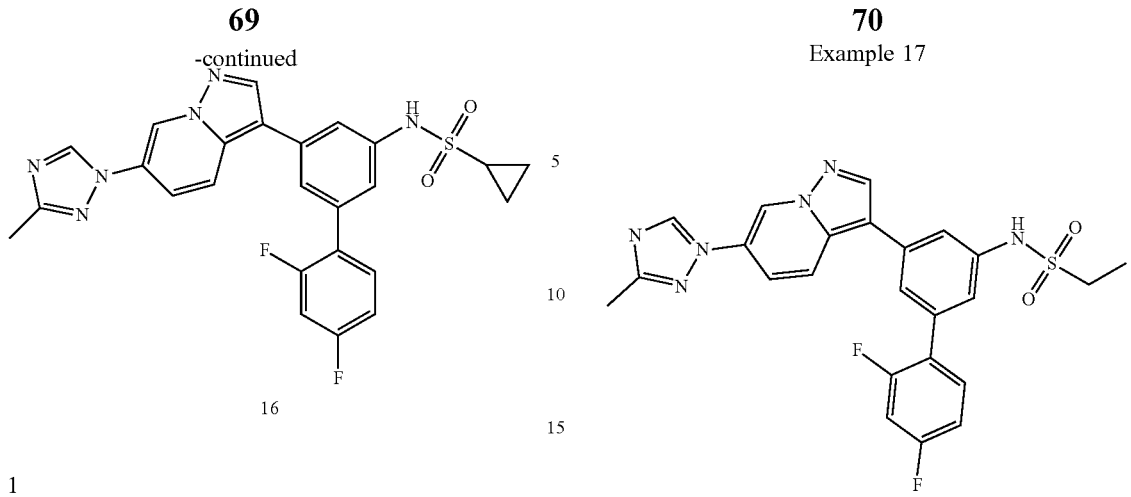

16

Example 17

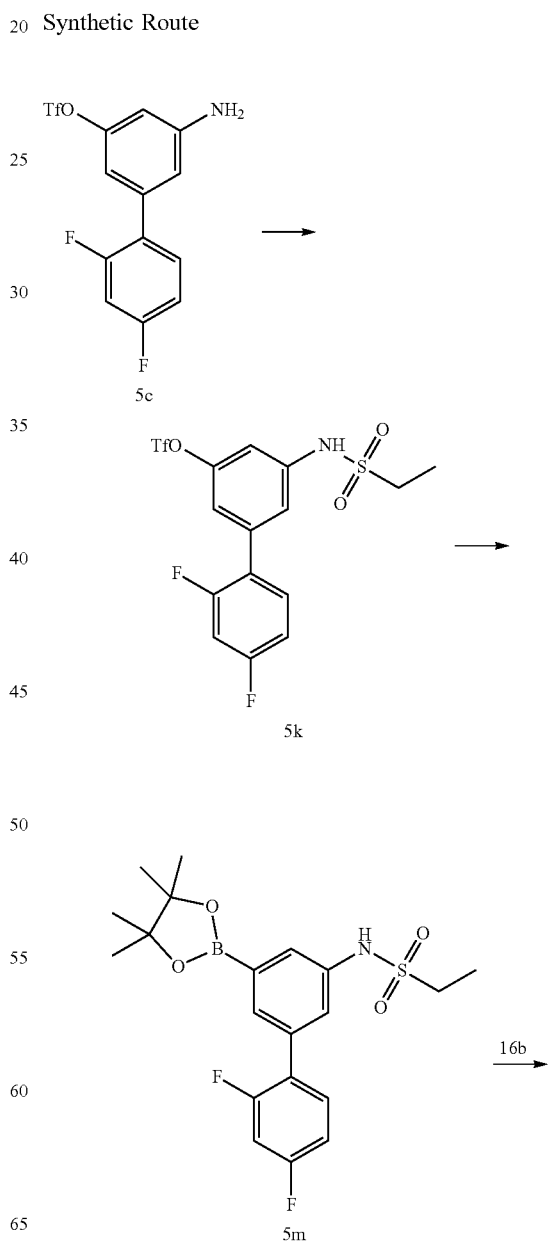

Step 1

3-methyl-1H-1,2,4-triazole (632.58 mg, 7.61 mmol), 6-bromopyrazolo[1,5-a]pyridine (1 g, 5.08 mmol), (1S, 2S)—N,N-dimethylcyclohexyl-1,2-diamine (1.44 g, 10.15 mmol), cesium carbonate (3.31 g, 10.15 mmol) and cuprous iodide (241.65 mg, 1.27 mmol) were added to N,N-dimethylformamide (10 mL). The air was replaced with nitrogen three times, and then the reaction solution was stirred at 120° C. for 5 hours. To the reaction solution were added saturated ammonium chloride (20 mL) and ethyl acetate (30 mL*3) for extraction and phase separation. The organic phase was dried over anhydrous sodium sulfate and filtered. The filtrate was concentrated to obtain a crude, which was purified by column chromatography to obtain compound 16a.

LCMS (ESI) m/z: 200.2 [M+1]$^+$

Step 2

Compound 16a (0.3 g, 1.51 mmol) was added to dichloromethane (50 mL), and then N-iodosuccinimide (440.45 mg, 1.96 mmol) was added thereto. The reaction solution was stirred at 25° C. for 2 hours. To the reaction solution were added a sodium bicarbonate solution (100 mL) and dichloromethane (100 mL*2) for extraction and phase separation. The organic phase was dried, filtered and concentrated to obtain a crude. The crude was purified by preparative chromatography plate to obtain compound 16b.

LCMS (ESI) m/z: 326.0 [M+1]$^+$

Step 3

Compound 5e (107.11 mg, 246.07 μmol), compound 16b (0.08 g, 246.07 μmol), potassium phosphate (156.70 mg, 738.22 μmol) and Pd(dppf)Cl$_2$ (18.01 mg, 24.61 μmol) were added to dioxane (5 mL) and water (2 mL), and the reaction solution was stirred at 100° C. for 1 hour. Water (100 mL) and ethyl acetate (200 mL) were added to the reaction solution for extraction and phase separation. The organic phase was dried, filtered and concentrated to obtain a crude, and the crude was purified by preparative high performance liquid chromatography (chromatographic column: Welch Xtimate C18 100*25 mm*3 μm; mobile phase: [water (10 mM ammonium bicarbonate)-acetonitrile]; B (acetonitrile) %: 35%-65%, 10.5 min) to obtain compound 16.

LCMS (ESI) m/z: 507.1 [M+1]$^+$ $^1$H NMR (399 MHz, DMSO-d$_6$) δ 9.91-9.95 (m, 1H) 9.29-9.33 (m, 1H) 9.15-9.19 (m, 1H) 8.49-8.53 (m, 1H) 8.04-8.09 (m, 1H) 7.83-7.89 (m, 1H) 7.64-7.70 (m, 1H) 7.57-7.60 (m, 1H) 7.51-7.55 (m, 1H 7.36-7.42 (m, 1H) 7.30-7.34 (m, 1H) 7.18-7.24 (m, 1H) 2.71-2.76 (m, 1H) 2.33-2.41 (m, 3H) 0.90-1.01 (m, 4H).

Synthetic Route

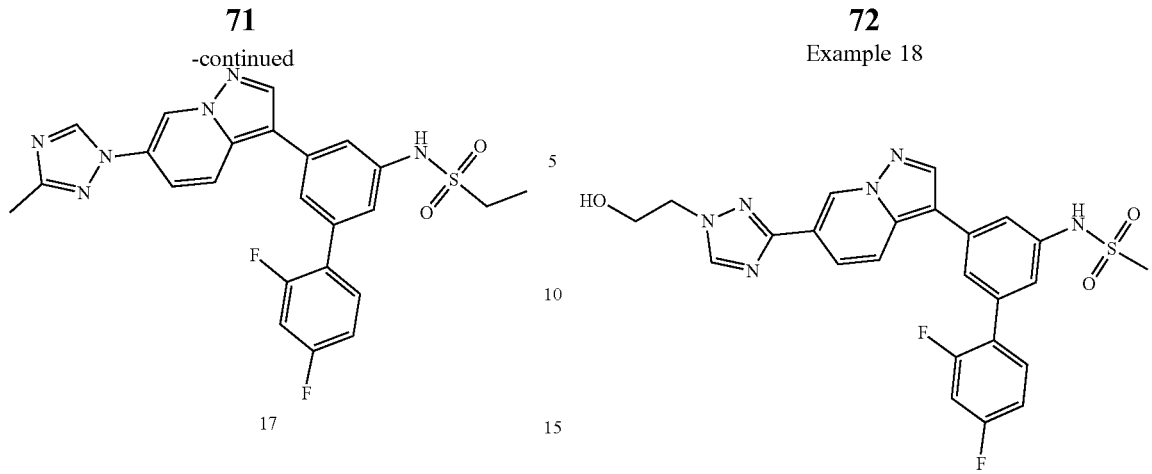

17

Example 18

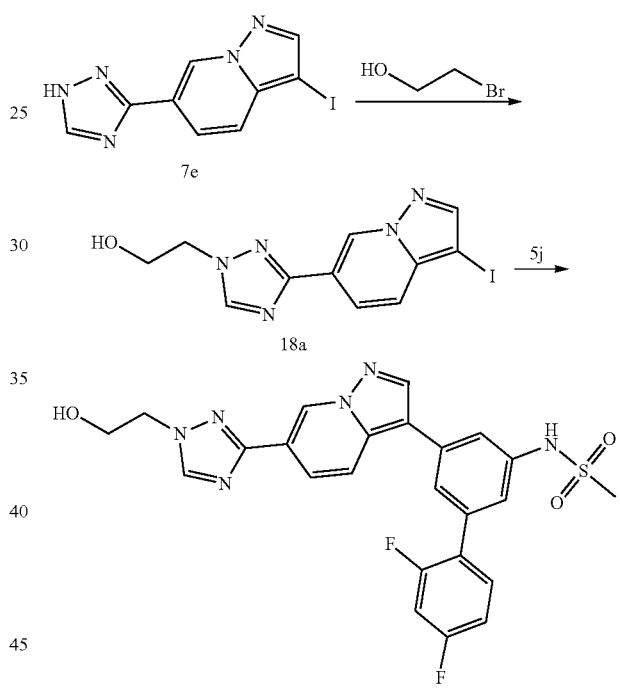

18

Step 1

Compound 5c (2 g, 5.66 mmol) was dissolved in pyridine (10 mL), and ethylsulfonyl chloride (873.53 mg, 6.79 mmol, 642.30 μL) was added dropwise thereto. The reaction solution was stirred at room temperature 30° C. for 4 hours. The reaction solution was extracted with 30 mL of water and 30 mL of ethyl acetate. The organic phase was washed twice with 30 mL of water and subjected to rotary evaporation to obtain crude compound 5k.

$^1$H NMR (400 MHz, CDCl$_3$): δ 7.70 (tt, J=7.74, 1.82 Hz, 1H), 7.30-7.32 (m, 1H), 7.25 (t, J=2.12 Hz, 1H), 7.17 (d, J=0.84 Hz, 1H), 6.90-7.02 (m, 2H), 3.21 (q, J=7.56 Hz, 2H), 1.37-1.43 (m, 3H).

Step 2

Compound 5k (2.5 g, 5.61 mmol) and bis(pinacolato) diboron (1.71 g, 6.74 mmol) were dissolved in dioxane (20 mL), and Pd(dppf)Cl$_2$ (410.72 mg, 561.32 μmol) and KOAc (1.10 g, 11.23 mmol) were added thereto. The reaction solution was stirred at 90° C. for 16 hours under nitrogen protection. The reaction solution was directly filtered. The filter cake was washed with ethyl acetate, and the filtrate was subjected to rotary evaporation to obtain a crude. The crude was purified by column chromatography with PE/EtOAc=5/1 to obtain compound 5m.

$^1$H NMR (400 MHz, CDCl$_3$): δ 7.68-7.72 (m, 1H), 7.55-7.58 (m, 1H), 7.51-7.54 (m, 1H), 7.41 (td, J=8.78, 6.52 Hz, 1H), 6.86-6.97 (m, 2H), 3.16 (q, J=7.56 Hz, 2H), 1.33-1.35 (m, 12H), 1.25 ppm (s, 3H).

Step 3

To dioxane (2 mL) and water (0.5 mL) were added compound 5m (208.32 mg, 492.14 μmol), compound 16b (80 mg, 246.07 μmol), anhydrous potassium phosphate (156.70 mg, 738.22 μmol), and Pd(dppf)Cl$_2$ (18.01 mg, 24.61 μmol). The reaction solution was reacted at 100° C. for 2 hours. The reaction solution was extracted with 50 mL of water and dichloromethane (50 mL*3). The organic phase was dried over anhydrous sodium sulfate, filtered, and concentrated to obtain a crude, which was purified by preparative high performance liquid chromatography (chromatographic column: Waters Xbridge BEH C18 100*30 mm*10 μm; mobile phase: [water (10 mM ammonium bicarbonate)-acetonitrile]; B (acetonitrile) %: 30%-60%, 8 min) to obtain compound 17.

LCMS (ESI) m/z: 495.3 [M+1]$^+$ $^1$H NMR (400 MHz, DMSO-d$_6$) δ 10.02 (s, 1H), 9.34 (s, 1H), 9.20 (s, 1H), 8.54 (s, 1H), 8.08-8.10 (d, J=9.2 Hz, 1H), 7.88-7.90 (m, 1H), 7.67-7.73, (m, 1H), 7.60 (s, 1H), 7.55 (s, 1H), 7.39-7.44 (m, 1H), 7.32 (s, 1H), 7.22-7.27 (m, 1H), 3.25-3.29 (m, 2H), 2.40 (s, 3H), 1.23-1.27 (t, J=7.4 Hz, 3H).

Synthetic Route

Step 1

Compound 7e (25 mg, 80.36 μmol), bromoethanol (12.05 mg, 96.44 μmol) and potassium carbonate (33.32 mg, 241.09 μmol) were heated to N,N-dimethylformamide (1 mL), and the reaction solution was stirred at 25° C. for 1 hour. To the reaction solution were added ethyl acetate (10 mL) and water (10 mL) for extraction and phase separation. The organic phase was dried, filtered and concentrated to obtain compound 18a.

LCMS (ESI) m/z: 356.1 [M+1]$^+$

Step 2

Compound 5j (51.86 mg, 126.71 μmol), compound 18a (30 mg, 84.48 μmol), potassium phosphate (44.83 mg, 211.19 μmol) and Pd(dppf)Cl$_2$ (6.18 mg, 8.45 μmol) were added to water (1 mL) and dioxane (3 mL). The air was replaced with nitrogen three times, and then the reaction solution was stirred at 100° C. for 2 hours. To the reaction solution were added water (100 mL) and ethyl acetate (100 mL) for extraction and phase separation. The organic phase was dried, filtered and concentrated to obtain a crude. The crude was purified by preparative high performance liquid chromatography (chromatographic column: Phenomenex Gemini-NX C18 75*30 mm*3 μm; mobile phase: [water (10 mM ammonium carbonate)-acetonitrile]; B (acetonitrile) %: 15%-50%, 10.5 min) to obtain compound 18.

LCMS (ESI) m/z: 511.2 [M+1]$^+$ $^1$H NMR (400 MHz, DMSO-d$_6$) δ 9.09 (s, 1H), 8.58-8.60 (m, 1H), 8.59 (s, 1H), 8.31 (s, 1H), 8.14 (s, 1H), 7.98 (s, 1H), 7.80-7.86 (m, 1H), 7.76 (s, 1H), 7.69 (s, 1H), 7.59 (s, 1H), 7.31 m, 1H), 6.82-6.92 (m, 2H), 4.31-4.28 (m, 2H), 3.82-3.80 (m, 2H), 2.60 (s, 3H).

Example 19

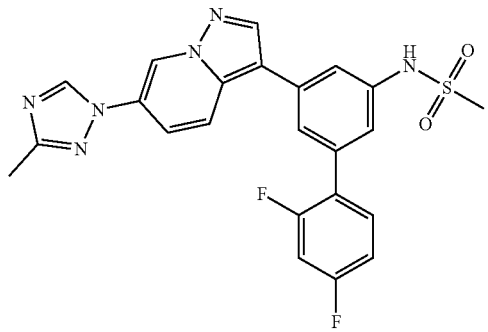

was purified by preparative thin-layer chromatography silica gel plate (PE:EtOAc=1:8) to obtain compound 19.

LCMS (ESI) m/z: 481.2 [M+1]$^+$ $^1$H NMR (400 MHz, DMSO-d$_6$) δ 9.30-9.37 (m, 1H), 9.17-9.22 (m, 1H), 8.51-8.55 (m, 1H), 8.06-8.13 (m, 1H), 7.83-7.90 (m, 1H), 7.66-7.74 (m, 1H), 7.48-7.58 (m, 2H), 7.36-7, (m, 1H), 7.18-7.31 (m, 2H), 6.69-6.80 (m, 1H), 3.01-3.14 (m, 3H), 2.36 (m, 3H).

Example 20

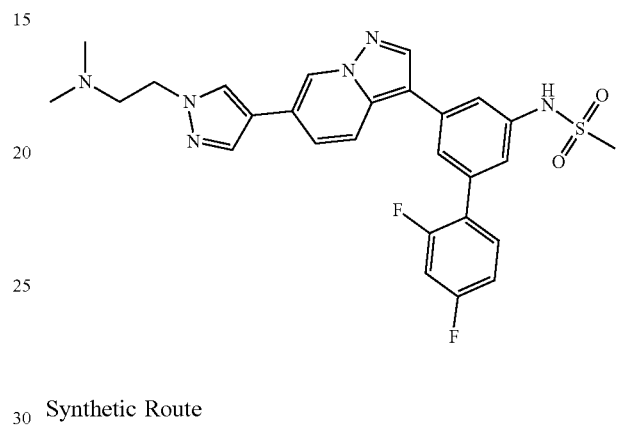

Synthetic Route

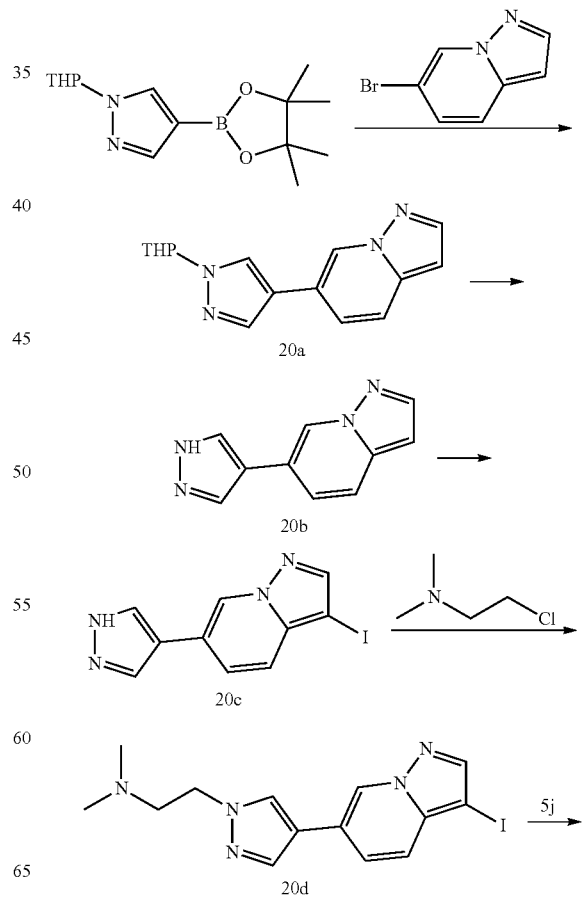

Synthetic Route

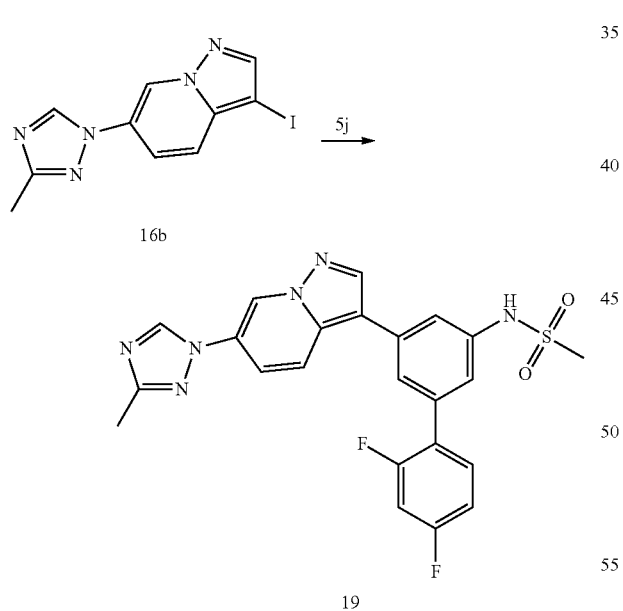

Step 1

Compound 5j (251.77 mg, 615.18 μmol), compound 16b (0.2 g, 615.18 μmol), potassium phosphate (391.75 mg, 1.85 mmol) and Pd(dppf)Cl$_2$ (45.01 mg, 61.52 μmol) were added to dioxane (10 mL) and water (4 mL). The reaction solution was stirred at 100° C. for 2 hours. To the reaction solution were added water (100 mL) and ethyl acetate (200 mL) for extraction and phase separation. The organic phase was dried, filtered and concentrated to obtain a crude. The crude

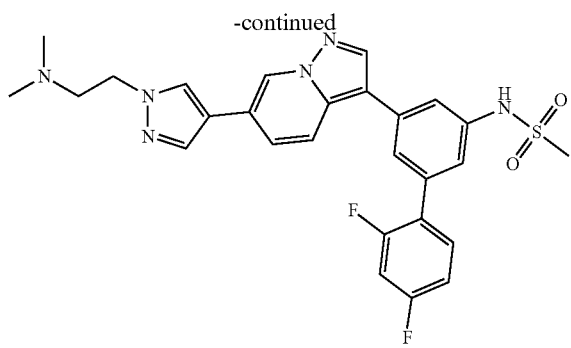

20

Step 1

To dioxane (45 mL) and water (15 mL) were added 1-(tetrahydro-2H-pyran-2-yl)-1H-pyrazole-4-boronic acid pinacol ester (8.47 g, 30.45 mmol), 6-bromopyrazolo[1,5-a]pyridine (4 g, 20.30 mmol), Pd(dppf)Cl₂ (148.55 mg, 203.00 µmol), and potassium phosphate (6.46 g, 30.45 mmol). The reaction solution was reacted at 100° C. for 2 hours. The reaction solution was extracted with 100 mL of water and dichloromethane (100 mL*2). The organic phase was dried over anhydrous sodium sulfate, filtered, and subjected to rotary evaporation. The crude was purified by column chromatography with PE/EtOAc=5/1 to obtain compound 20a.

LCMS (ESI) m/z: 269.3 [M+1]⁺

¹H NMR (400 MHz, DMSO-d₆) δ 9.04 (s, 1H), 8.48 (s, 1H), 8.08 (s, 1H), 7.96-7.97 (d, J=2.4 Hz, 1H), 7.70-7.72 (d, J=8.8 Hz, 1H), 7.51-7.54 (m, 1H), 6.58-6.59 (d, J=2.0 Hz, 1H), 5.40-5.43 (m, 1H), 3.93-3.96 (m, 1H), 3.62-3.69 (m, 1H), 2.07-2.16 (m, 1H), 1.94-1.98 (m, 2H), 1.65-1.75 (m, 1H), 1.53-1.59 (m, 2H).

Step 2

Compound 20a (3 g, 11.18 mmol) and hydrogen chloride/ethyl acetate (4 M, 2.80 mL) were added to ethyl acetate (30 mL), and the reaction solution was reacted at 25° C. for 3 hours. The reaction solution was subjected to rotary evaporation to obtain compound 20b.

LCMS (ESI) m/z: 185.2 [M+1]⁺

¹H NMR (399 MHz, DMSO-d₆) δ 11.76 (s, 1H), 9.05 (s, 1H), 8.29 (s, 2H), 7.96-7.97 (d, J=2.4 Hz, 1H), 7.7.1-7.73 (m, 1H), 7.52-7.55 (m, 1H), 6.58-6.62 (m, 1H).

Step 3

To anhydrous dichloromethane (10 mL) was added compound 20b (1 g, 5.43 mmol), N-iodosuccinimide (1.34 g, 5.97 mmol), and glacial acetic acid (32.60 mg, 542.90 µmol, 31.05 µL), and the reaction solution was reacted at 25° C. for 12 hours. The reaction solution was extracted with 20 mL of water and dichloromethane (50 mL*2). The organic phase was dried over anhydrous sodium sulfate and filtered, and then the filtrate was concentrated under reduced pressure to obtain a crude. The crude was purified by column chromatography with PE/EtOAc=1/1 to obtain compound 20c.

LCMS (ESI) m/z: 311.1 [M+1]⁺

¹H NMR (400 MHz, DMSO-d₆) δ 11.07 (s, 1H), 9.09 (s, 1H), 8.21 (s, 2H), 8.07 (s, 1H), 7.65-7.67 (m, 1H), 7.50-7.52 (d, J=9.2 Hz, 1H).

Step 4

To N,N-dimethylformamide (2 mL) were added compound 20c (50 mg, 161.24 µmol), 2-chloro-N,N-dimethylethylamine (26.02 mg, 241.86 µmol) and cesium carbonate (105.07 mg, 322.48 µmol), and the reaction solution was reacted at 25° C. for 2 hours. The reaction solution was extracted with 30 mL of an aqueous saturated sodium chloride solution and dichloromethane (30 mL*3). The organic phase was dried over anhydrous sodium sulfate, filtered, and subjected to rotary evaporation to obtain compound 20d.

LCMS (ESI) m/z: 382.2 [M+1]⁺

¹H NMR (400 MHz, DMSO-d₆) δ 9.04 (s, 1H), 8.31 (s, 1H), 8.05 (s, 1H), 8.01 (s, 1H), 7.58-7.60 (m, 1H), 7.49-7.52 (d, J=9.2 Hz, 1H), 4.20-4.23 (t, J=6.4 Hz, 2H), 2.69-2.71 (t, J=6.4 Hz, 2H), 2.19 (s, 6H).

Step 5

To dioxane (2 mL) and water (0.5 mL) were added compound 20d (30 mg, 78.70 µmol), compound 5j (48.31 mg, 118.04 µmol), anhydrous potassium phosphate (33.41 mg, 157.39 µmol), and Pd(dppf)Cl₂ (5.76 mg, 7.87 µmol), and the reaction solution was reacted at 65° C. for 2 hours. The reaction solution was extracted with 30 mL of water and dichloromethane (30 mL*3). The organic phase was dried over anhydrous sodium sulfate, filtered, and subjected to rotary evaporation to obtain a crude. The crude was purified by preparative thin-layer chromatography silica gel plate (dichloromethane:methanol=9:1) to obtain compound 20.

LCMS (ESI) m/z: 537.3 [M+1]⁺

¹H NMR (400 MHz, DMSO-d₆) δ 9.95 (s, 1H), 9.08 (s, 1H), 8.40 (s, 1H), 8.35 (s, 1H), 8.05 (s, 1H), 7.95-7.97 (d, J=9.2 Hz, 1H), 7.65-7.73 (m, 2H), 7.54-7.58 (m, 2H), 7.38-7.44 (m, 1H), 722-7.27 (m, 2H), 4.21-4.24 (t, J=6.4 Hz, 2H), 3.10 (s, 3H), 2.68-2.71 (t, J=6.6 Hz, 2H), 2.19 (s, 6H).

Example 21

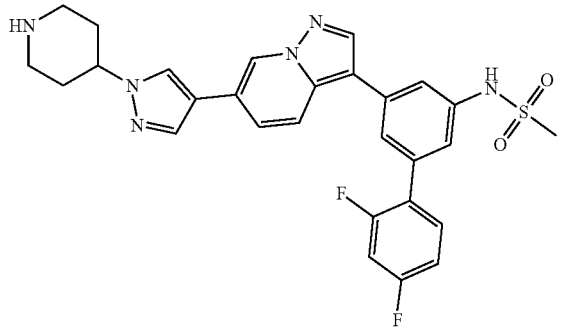 [SMILES: CS(=O)(=O)Nc1cc(-c2ccc(F)cc2F)cc(-c2cnn3cc(-c4cnn(C5CCNCC5)c4)ccc23)c1]

Synthetic Route

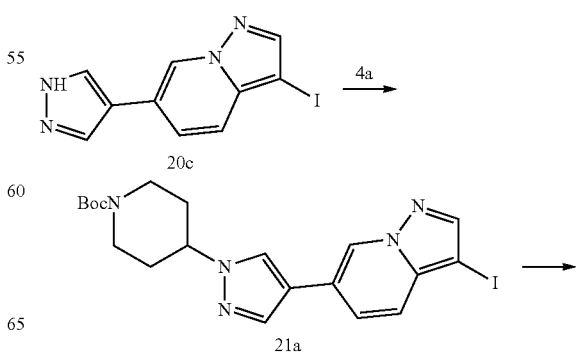

-continued

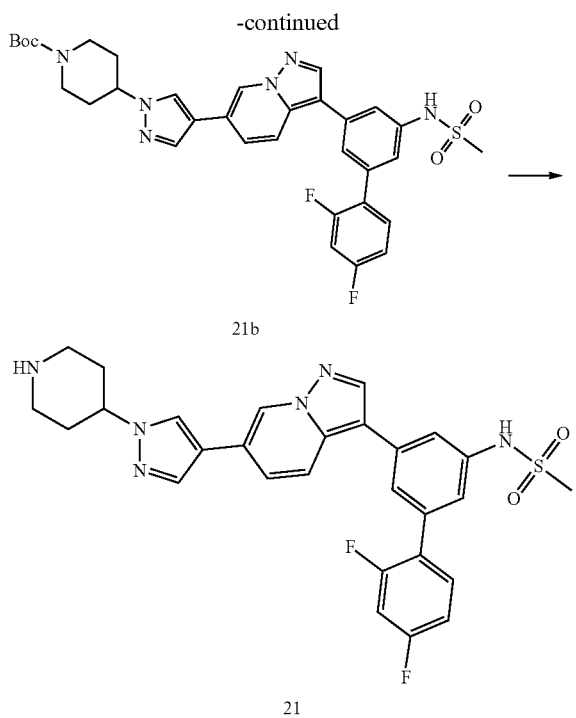

21b

21

Step 1

To N,N-dimethylformamide (1 mL) were added compound 20c (0.18 g, 580.47 μmol), compound 4a (324.31 mg, 1.16 mmol) and cesium carbonate (945.64 mg, 2.90 mmol), and the reaction solution was reacted at 60° C. for 12 hours. The reaction solution was extracted with 50 mL of saturated brine and dichloromethane (50 mL*4). The organic phase was dried over anhydrous sodium sulfate, filtered, and subjected to rotary evaporation to obtain compound 21a.

LCMS (ESI) m/z: 438.1 [M−56]$^+$ $^1$H NMR (400 MHz, DMSO-d$_6$) δ 9.07 (s, 1H), 8.43 (s, 1H), 8.07 (s, 1H), 8.05 (s, 1H), 7.61-7.64 (m, 1H), 7.51-7.53 (d, J=9.2 Hz, 1H), 4.79-4.85 (m, 1H), 3.57-3.63 (m, 2H), 3.1.5-3.17 (m, 2H), 2.04-2.06 (m, 2H), 1.88-1.93 (m, 2H), 1.40 (s, 9H).

Step 2

To dioxane (2 mL) and water (0.5 mL) were added compound 21a (90 mg, 182.43 μmol), compound 5j (74.66 mg, 182.43 μmol), anhydrous potassium phosphate (116.17 mg, 547.29 μmol), and Pd(dppf)Cl$_2$ (13.35 mg, 18.24 μmol), and the reaction solution was reacted at 65° C. for 2 hours. The reaction solution was extracted with 50 mL of water and dichloromethane (50 mL*3). The organic phase was dried over anhydrous sodium sulfate and filtered, and the filtrate was subjected to rotary evaporation. The crude was purified by preparative thin-layer chromatography silica gel plate (petroleum ether:ethyl acetate=1:1) to obtain compound 21b.

LCMS (ESI) m/z: 649.3 [M+1]$^+$ $^1$H NMR (400 MHz, DMSO-d$_6$) δ 9.95 (s, 1H), 9.09 (s, 1H), 8.46 (s, 1H), 8.41 (s, 1H), 8.09 (s, 1H), 7.95-7.97 (d, J=9.2 Hz, 1H), 7.68-7.71 (m, 2H), 7.55-7.58 (m, 2H), 7.39-7.45 (m, 2H), 7.27 (s, 1H), 4.40 (s, 1H), 4.04-4.09 (m, 2H), 3.10 (s, 3H), 2.89-2.95 (m, 2H), 2.06-2.09 (m, 2H), 1.79-1.83 (m, 2H), 1.43 (s, 9H).

Step 3

Compound 21b (25 mg, 38.54 μmol) and hydrogen chloride/methanol (4 M, 5 mL) were added to anhydrous methanol (2 mL), and the reaction solution was reacted at 25° C. for 1 hour. The reaction solution was subjected to rotary evaporation and purified by preparative high performance liquid chromatography (chromatographic column: Phenomenex Luna C18 100*30 mm*5 μm; mobile phase: [water (0.04% hydrochloric acid)-acetonitrile]; B (acetonitrile) %: 20%-50%, 10 min) to obtain the hydrochloride salt of compound 21.

LCMS (ESI) m/z: 549.2 [M+1]$^+$ $^1$H NMR (400 MHz, DMSO-d$_6$) δ 9.98 (s, 1H), 9.14 (s, 1H), 8.89-8.92 (m, 1H), 8.65-8.66 (m, 1H), 8.42-8.43 (d, J=6.0 Hz, 2H), 8.15 (s, 1H), 7.86-7.98 (d, J=9.2 Hz, 1H), 7.69-7.73 (m, 1H), 7.59 (s, 1H), 7.55 (s, 1H), 7.39-7.45 (m, 1H), 7.27 (s, 1H), 4.50-4.56 (m, 1H), 3.45-3.53 (m, 4H), 3.13-3.19 (m, 1H), 3.11 (s, 3H), 2.26-2.28 (m, 2H), 2.15-2.18 (m, 2H).

The hydrochloride salt of compound 21 was added to a sodium bicarbonate solution, and extracted with ethyl acetate. The organic phase was dried over anhydrous sodium sulfate and concentrated under reduced pressure to obtain compound 21.

The compound 22 in Table 3 can be prepared by referring to the steps and methods similar to those in the route for the aforementioned example 21.

TABLE 3

| Product no. | Product structure | Raw material A | Product LCMS m/z: [M + 1]$^+$ | Product $^1$H NMR |
|---|---|---|---|---|
| Example 22 |  | Br~~OH / OH | 540.1 | Compound 22: $^1$H NMR (400 MHz, DMSO-d$_6$) δ 9.96 (s, 1H), 9.09 (s, 1 H), 8.40 (s, 1 H), 8.29 (s, 1 H), 8.07 (s, 1 H), 7.95-7.97 (d, J = 9.2 Hz, 1 H), 7.67-7.73 (m, 2 H), 7.54-7.58 (d, J = 16.0 Hz, 2 H), 7.39-7.44 (m, 1 H), 7.25-7.27 (m, 2 H), 5.03-5.04 (d, J = 5.2 Hz, 1 H), 4.77 (s, 1 H), 4.24-4.28 (m, 1 H), 3.98-4.03 (m, 1 H), 3.86 (s, 1 H), 3.10 (s, 3 H). |

Example 23

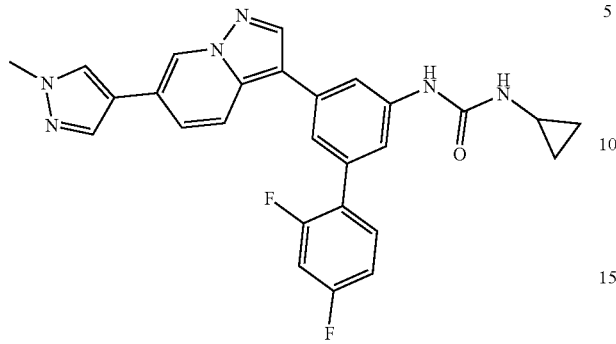

Synthetic Route

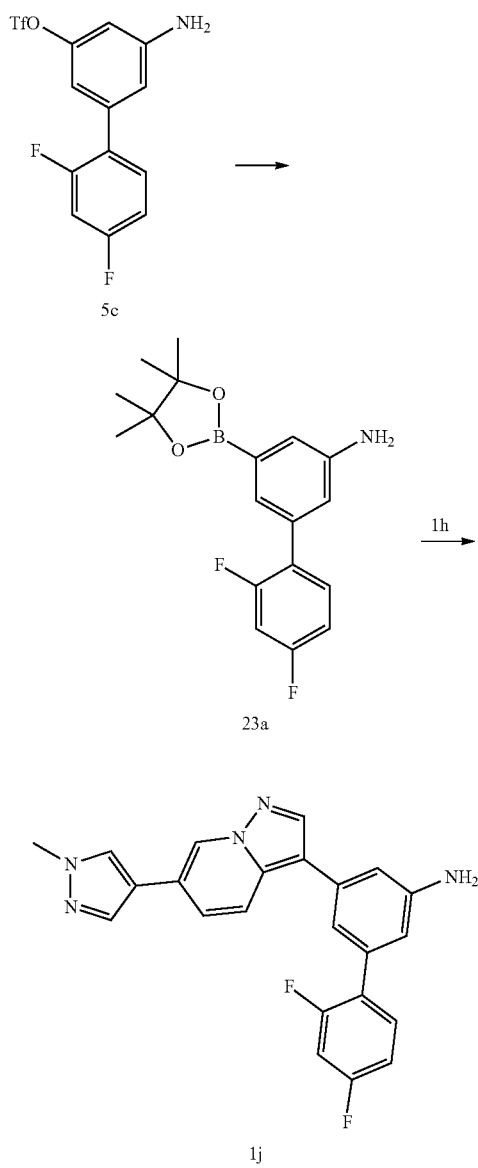

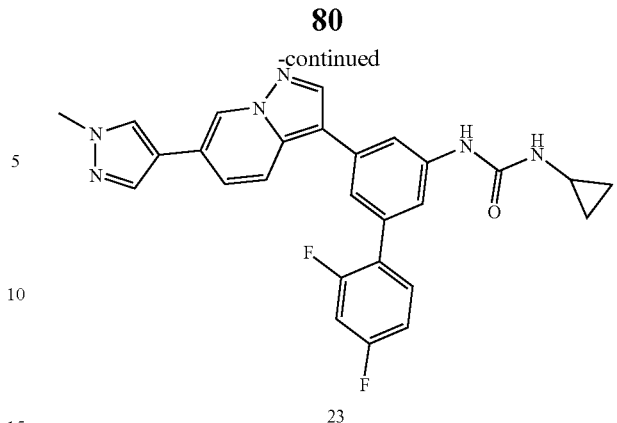

Step 1

Compound 5c (0.1 g, 283.07 μmol) was dissolved in dioxane (2 mL), and bis(pinacolato)diboron (86.26 mg, 339.69 μmol), KOAc (55.56 mg, 566.15 μmol), and Pd(dppf)Cl$_2$ (20.71 mg, 28.31 μmol) were added thereto. The air was replaced with nitrogen three times, and the reaction solution was stirred at 100° C. for 16 hours under a nitrogen atmosphere. The reaction solution was filtered through celite, and the filtrate was subjected to rotary evaporation under reduced pressure to obtain a crude. The crude was purified by preparative thin-layer chromatography silica gel plate with PE/EtOAc=3/1 to obtain compound 23a.

LCMS (ESI) m/z: 332.0 [M+1]$^+$

Step 2

Compound 1h (320.78 mg, 1.16 mmol) and compound 23a (0.46 g, 1.39 mmol) were dissolved in dioxane (10 mL) and water (3 mL), and Pd(dppf)Cl$_2$ (84.70 mg, 115.75 μmol) and potassium phosphate (491.42 mg, 2.32 mmol) were added thereto. The air was replaced with nitrogen three times, and the reaction solution was stirred at 100° C. for 16 hours under a nitrogen atmosphere. The reaction solution was filtered through celite, and the filtrate was subjected to rotary evaporation to obtain a crude. The crude was purified by column chromatography with PE/EA=1/1 to obtain compound 1j.

LCMS (ESI) m/z: 402.0 [M+1]$^+$

Step 3

Compound 1j (0.05 g, 124.56 μmol) was dissolved in dichloromethane (1 mL), and DIEA (48.29 mg, 373.68 μmol, 65.09 μL) and triphosgene (55.44 mg, 186.84 μmol) were added thereto. The reaction solution was stirred at 0° C. for 10 minutes. Moreover, cyclopropylamine (14.22 mg, 249.12 μmol, 17.26 μL) was dissolved in dichloromethane (1 mL), and DIEA (48.30 mg, 373.68 μmol, 65.09 μL) was added thereto. The reaction solution was stirred at 0° C. for 10 minutes, and then added to the above reaction solution and stirred for another 7 to 10 minutes. The reaction solution was extracted with water (2 mL*2), and the organic phase was concentrated under reduced pressure to obtain a crude. The crude was purified by preparative high performance liquid chromatography (chromatographic column: Boston Green ODS 150*30 mm*5 μm; mobile phase: [water (0.075% trifluoroacetic acid)-acetonitrile]; B (acetonitrile) %: 45%-75%, 7 min) to obtain compound 23.

LCMS (ESI) m/z: 485.1 [M+1]$^+$ $^1$H NMR (400 MHz, CD$_3$OD) δ 8.79 (s, 1H), 8.23 (s, 1H), 8.08 (s, 1H), 7.99 (d, J=9.04 Hz, 1H), 7.93 (s, 1H), 7.87 (s, 1H), 7.54-7.63 (m, 2H), 7.41 (s, 2H), 7.04-7.12 (m, 2H), 3.96 (s, 3H), 2.63 (s, 1H), 0.66-0.86 (m, 2H), 0.55 (br s, 2H).

The compounds in Table 4 can be prepared by referring to the steps and methods similar to those in the route for the aforementioned example 23.

TABLE 4
| Product no. | Product structure | Raw material A | Product LCMS m/z: [M + 1]+ | Product ¹H NMR |
|---|---|---|---|---|
| Example 24 | | H₂N—O— | 475.3 | Compound 24: ¹H NMR (400 MHz, CD₃OD) δ 8.76 (s, 1H), 8.22 (s, 1H), 8.06 (s, 1H), 7.98 (d, J = 9.26 Hz, 1H), 7.88-7.94 (m, 2H), 7.57-7.66 (m, 2H), 7.55 (dd, J = 1.38, 9.26 Hz, 1H), 7.47 (d, J = 1.64 Hz, 1H), 7.01-7.12 (m, 2H), 3.95 (s, 3H), 3.78 (s, 3H). |
| Example 25 | | HO—⟨NH⟩ | 515.4 | Compound 25: ¹H NMR (400 MHz, CD₃OD) δ 8.69-8.80 (m, 1H), 8.21 (s, 1H), 8.06 (s, 1H), 7.97 (d, J = 9.26 Hz, 1H), 7.91 (s, 1H), 7.84 (t, J = 1.74 Hz, 1H), 7.48-7.64 (m, 3H), 7.41 (d, J = 1.64 Hz, 1H), 7.02-7.12 (m, 2H), 4.41-4.54 (m, 1H), 3.95 (s, 3H), 3.59-3.70 (m, 3H), 3.46-3.55 (m, 1H), 1.94-2.20 (m, 2H). |
Example 26
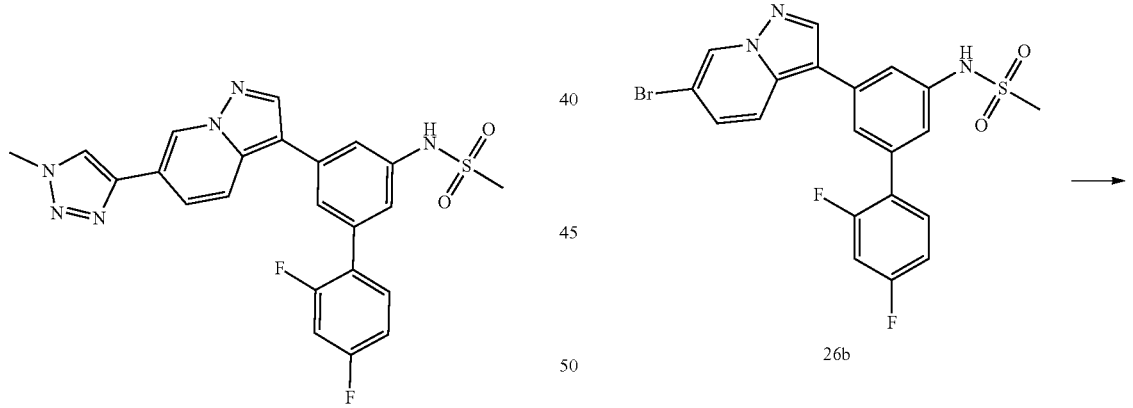
Synthetic Route
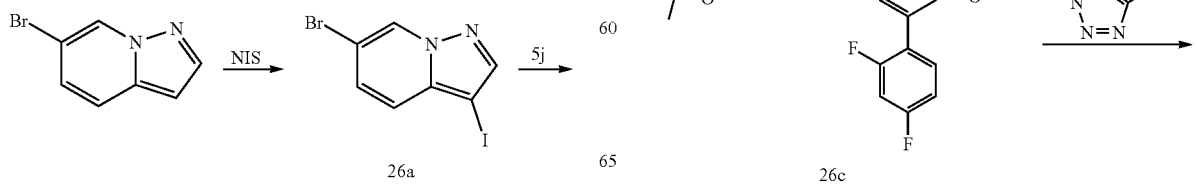

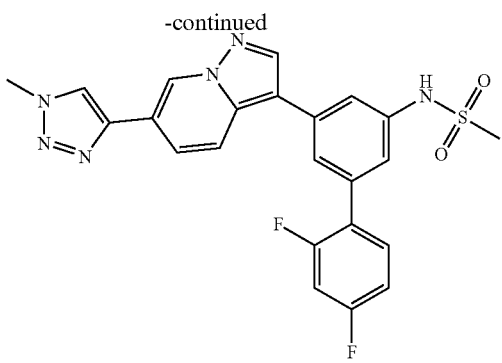

26

Step 1

To a solution of 6-bromopyrazolo[1,5-a]pyridine (0.2 g, 1.02 mmol) in dichloromethane (5 mL) was added NIS (274.05 mg, 1.22 mmol), and the reaction solution was stirred at 30° C. for 5 hours. The reaction solution was extracted with water (10 mL) and dichloromethane (10 mL*3). The organic phases were combined, dried over anhydrous sodium sulfate, and then concentrated under reduced pressure to obtain compound 26a.

LCMS (ESI) m/z: 324.7 [M+3]$^+$

Step 2

To a solution of compound 26a (0.4 g, 1.24 mmol) and compound 5j (608.31 mg, 1.49 mmol) in dioxane (2 mL) and water (0.5 mL) were added sodium carbonate (328.21 mg, 3.10 mmol) and Pd(dppf)Cl$_2$ (90.63 mg, 123.87 μmol). The reaction solution was stirred at 110° C. for 20 minutes under microwave conditions and nitrogen protection. To the reaction solution were added water (10 mL) and then ethyl acetate (10 mL*3) for extraction. The organic phases were combined, dried over anhydrous sodium sulfate, and concentrated under reduced pressure to obtain a crude. The crude was purified by column chromatography with PE/EA=3/1 to obtain compound 26b.

LCMS (ESI) m/z: 479.9 [M+3]$^+$

Step 3

To a solution of compound 26b (0.3 g, 627.21 μmol) and bis(pinacolato)diboron (175.20 mg, 689.93 μmol) in dioxane (3 mL) were added Pd(dppf)Cl$_2$ (45.89 mg, 62.72 μmol) and potassium acetate (123.11 mg, 1.25 mmol). The reaction solution was stirred at 100° C. for 16 hours under nitrogen protection. The reaction solution was filtered off with suction through celite, and the filtrate was concentrated under reduced pressure to obtain crude compound 26c.

LCMS (ESI) m/z: 526.1 [M+1]$^+$

Step 4

To a solution of 4-bromo-1-methyl-triazole (30 mg, 185.20 μmol) and compound 26c (145.95 mg, 277.80 μmol) in dioxane (3 mL) and water (1 mL) were added Pd(dppf)Cl$_2$ (13.55 mg, 18.52 μmol) and potassium phosphate (78.62 mg, 370.40 μmol). The reaction solution was stirred at 100° C. for 0.5 hour under microwave conditions and nitrogen protection. To the reaction solution were added water (10 mL) and then ethyl acetate (10 mL*3) for extraction and phase separation. The organic phases were combined, dried over anhydrous sodium sulfate, and concentrated under reduced pressure to obtain a crude. The crude was purified by preparative high performance liquid chromatography (chromatographic column: Boston Green ODS 150*30 mm*5 μm; mobile phase: [water (0.075% trifluoroacetic acid)-acetonitrile]; B (acetonitrile) %: 40%-70%, 7 min) to obtain the trifluoroacetate salt of compound 26.

LCMS (ESI) m/z: 481.3 [M+1]$^+$ $^1$H NMR (400 MHz, DMSO-d$_6$) δ 9.96 (s, 1H), 9.21 (s, 1H), 8.65 (s, 1H), 8.48 (s, 1H), 8.05 (d, J=9.54 Hz, 1H), 7.87 (d, J=9.30 Hz, 1H), 7.64-7.77 (m, 1H), 7.57 (br d, J=11.04 Hz, 2H), 7.35-7.47 (m, 1H), 7.18-7.33 (m, 2H), 4.13 (s, 3H), 3.10 (s, 3H).

The trifluoroacetate salt of compound 26 was added to a sodium bicarbonate solution, and extracted with ethyl acetate. The organic phase was dried over anhydrous sodium sulfate and concentrated under reduced pressure to obtain compound 26.

The compounds in Table 5 can be prepared by referring to the steps and methods similar to those in the route for the aforementioned example 26. The trifluoroacetate salt of the obtained compound was added to a sodium bicarbonate solution, and extracted with ethyl acetate. The organic phase was dried over anhydrous sodium sulfate, and concentrated under reduced pressure to obtain the compound.

TABLE 5

| Product no. | Product structure | Raw material A | Product LCMS m/z: [M + 1]$^+$ | Product $^1$H NMR |
|---|---|---|---|---|
| Example 27 | | | 480.0 | Trifluoroacetate salt of compound 27: $^1$H NMR (400 MHz, CD$_3$OD) δ 9.02 (s, 1H), 8.84 (s, 1H), 8.37 (s, 1H), 8.04 (d, J = 9.29 Hz, 1H), 7.96 (s, 1H), 7.54-7.66 (m, 4H), 7.33 (s, 1H), 7.06-7.16 (m, 2H), 3.99 (s, 3H), 3.07 (s, 3H). |

TABLE 5-continued

| Product no. | Product structure | Raw material A | Product LCMS m/z: [M + 1]+ | Product 1H NMR |
|---|---|---|---|---|
| Example 28 | 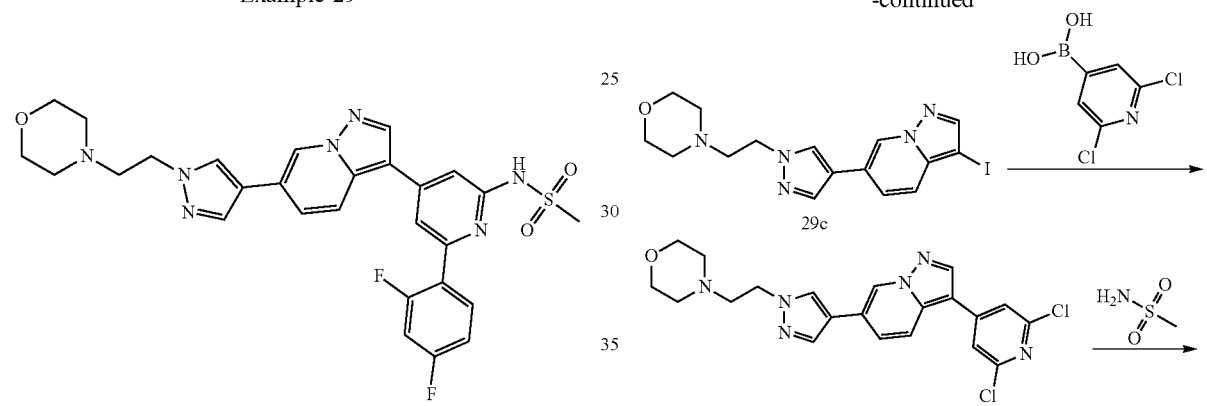 | | 480.1 | Compound 28: 1H NMR (400 MHz, CD3OD) δ 8.73 (s, 1H), 8.31 (s, 1H), 7.98 (d, J = 9.30 Hz, 1H), 7.55-7.62 (m, 2H), 7.52 (br d, J = 2.02 Hz, 2H), 7.42 (d, J = 9.30 Hz, 1H), 7.29 (s, 1H), 6.98-7.17 (m, 2H), 6.48 (d, J = 2.02 Hz, 1H), 3.91 (s, 3H), 3.03 (s, 3H). |

Example 29

Synthetic Route

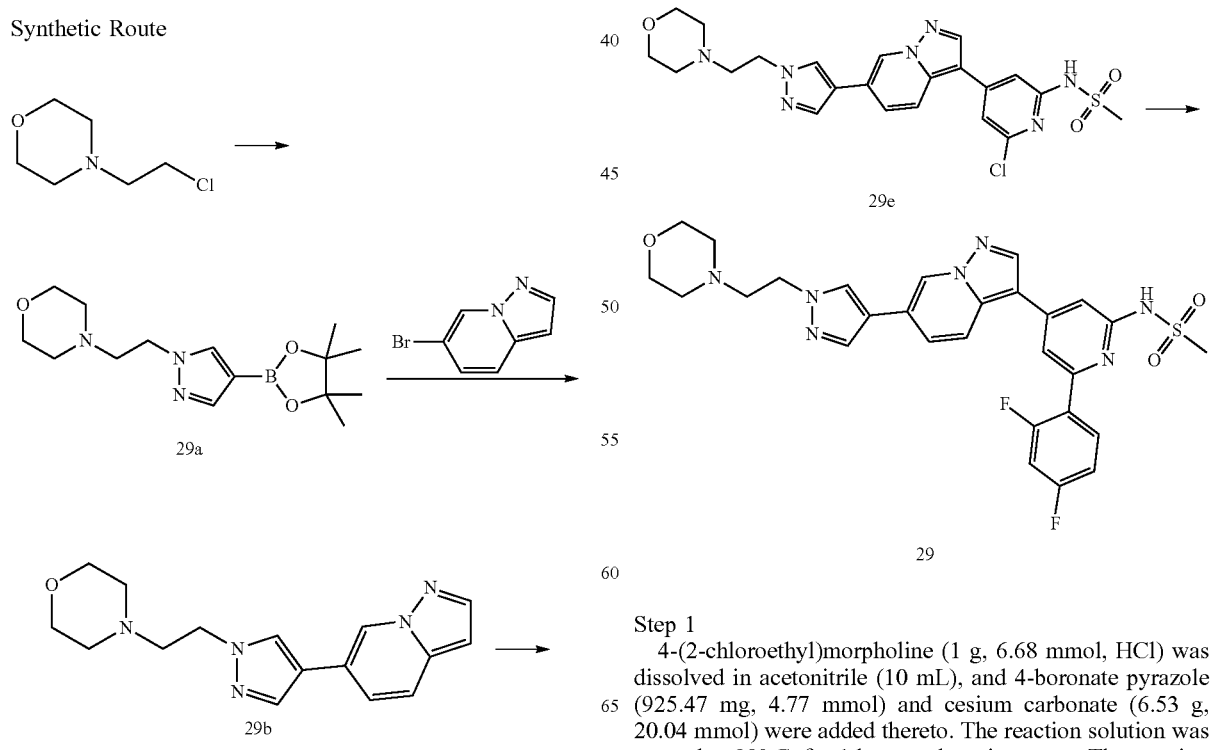

Step 1

4-(2-chloroethyl)morpholine (1 g, 6.68 mmol, HCl) was dissolved in acetonitrile (10 mL), and 4-boronate pyrazole (925.47 mg, 4.77 mmol) and cesium carbonate (6.53 g, 20.04 mmol) were added thereto. The reaction solution was reacted at 90° C. for 1 hour under microwave. The reaction solution was filtered off with suction, and the filtrate was concentrated under reduced pressure to obtain a crude. The crude was directly used in the next step without further purification to obtain compound 29a.

Step 2

6-bromopyrazole[1,5-a]pyridine (0.95 g, 4.82 mmol) was dissolved in dioxane (20 mL) and water (5 mL), and compound 29a (1.78 g, 5.79 mmol), Pd(dppf)Cl$_2$ (352.80 mg, 482.16 μmol) and potassium phosphate (1.02 g, 4.82 mmol) were added thereto. The reaction solution was stirred at 100° C. for 16 hours under nitrogen protection. The reaction solution was filtered through celite, and the filtrate was subjected to rotary evaporation under reduced pressure to obtain a crude. The crude was purified by column chromatography with PE/EA=1/1 to obtain compound 29b.

LCMS (ESI) m/z: 298.2 [M+1]$^+$

Step 3

Compound 29b (0.4 g, 1.35 mmol) was dissolved in DCM (10 mL), and NIS (363.18 mg, 1.61 mmol) was added thereto. The reaction solution was stirred at 25° C. for 16 hours. The reaction solution was extracted with 10 mL of water. The organic phases were combined, and subjected to rotary evaporation under reduced pressure to obtain a crude. The crude was purified by column chromatography with DCM/MeOH=10/1 to obtain compound 29c.

LCMS (ESI) m/z: 423.9 [M+1]$^+$

Step 4

Compound 29c (0.59 g, 1.39 mmol) was dissolved in dioxane (10 mL) and water (2 mL), and (2,6-dichloro-4-pyridine)boronic acid (320.85 mg, 1.67 mmol), Pd(dppf)Cl$_2$ (102.00 mg, 139.40 μmol), and potassium phosphate (591.79 mg, 2.79 mmol) were added thereto. The air was replaced with nitrogen three times, and the reaction solution was reacted at 100° C. for 16 hours. The reaction solution was filtered through celite, and the filtrate was subjected to rotary evaporation under reduced pressure to obtain a crude. The crude was purified by column chromatography with DCM/MeOH=20/1 to obtain compound 29d.

LCMS (ESI) m/z: 443.1 [M+1]$^+$

Step 5

Compound 29d (0.05 g, 112.78 μmol) was dissolved in dioxane (3 mL), and methylsulfonamide (21.46 mg, 225.57 μmol), palladium acetate (2.53 mg, 11.28 μmol), 4,5-bisdiphenylphosphino-9,9-dimethylxanthene (6.53 mg, 11.28 μmol), and cesium carbonate (110.24 mg, 338.35 μmol) were added thereto. The reaction solution was reacted at 120° C. for 1 hour under microwave and nitrogen protection. The reaction solution was filtered through celite, and the filtrate was subjected to rotary evaporation under reduced pressure to obtain a crude. The crude was purified by preparative thin-layer chromatography silica gel plate (DCM/MEOH=20:1) to obtain compound 29e.

LCMS (ESI) m/z: 502.1 [M+1]$^+$

Step 6

Compound 29e (0.03 g, 59.76 μmol) was dissolved in dioxane (2 mL) and water (0.5 mL), and 2,4-difluorophenylboronic acid (18.87 mg, 119.52 μmol), Pd(dppf)Cl$_2$ (4.37 mg, 5.98 μmol), and potassium phosphate (25.37 mg, 119.52 μmol) were added thereto. The air was replaced with nitrogen three times, and the reaction solution was stirred at 100° C. for 16 hours. The reaction solution was filtered through celite, and the filtrate was subjected to rotary evaporation under reduced pressure to obtain a crude. The crude was purified by HPLC (chromatographic column: Boston Green ODS 150*30 mm*5 μm; mobile phase: [water (0.075% trifluoroacetic acid)-acetonitrile]; B (acetonitrile) %: 25%-55%, 8 min) to obtain the trifluoroacetate salt of compound 29.

LCMS (ESI) m/z: 580.2 [M+1]$^+$ $^1$H NMR (400 MHz, CD$_3$OD) δ 8.86 (s, 1H), 8.39 (s, 1H), 8.22 (s, 1H), 8.12 (br d, J=6.78 Hz, 1H), 8.06 (s, 1H), 8.00 (d, J=9.04 Hz, 1H), 7.74 (s, 1H), 7.64-7.71 (br d, J=8.78 Hz, 1H), 7.26 (s, 1H), 7.03-7.18 (m, 2H), 4.69 (br t, J=5.64 Hz, 2H), 3.95 (br s, 2H), 3.75 (br t, J=5.64 Hz, 2H), 3.43 (br s, 2H), 3.35-3.38 (m, 3H), 1.29 (br s, 4H).

The trifluoroacetate salt of compound 29 was added to a sodium bicarbonate solution, and extracted with ethyl acetate. The organic phase was dried over anhydrous sodium sulfate and concentrated under reduced pressure to obtain compound 29.

Example 30

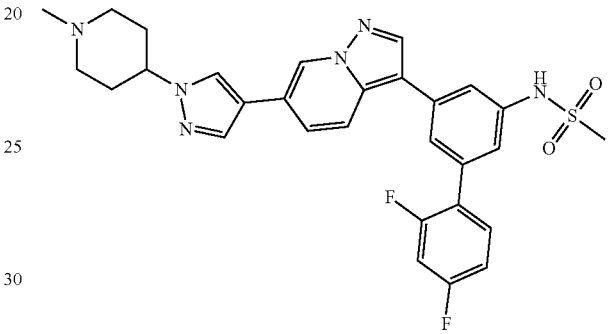

Synthetic Route

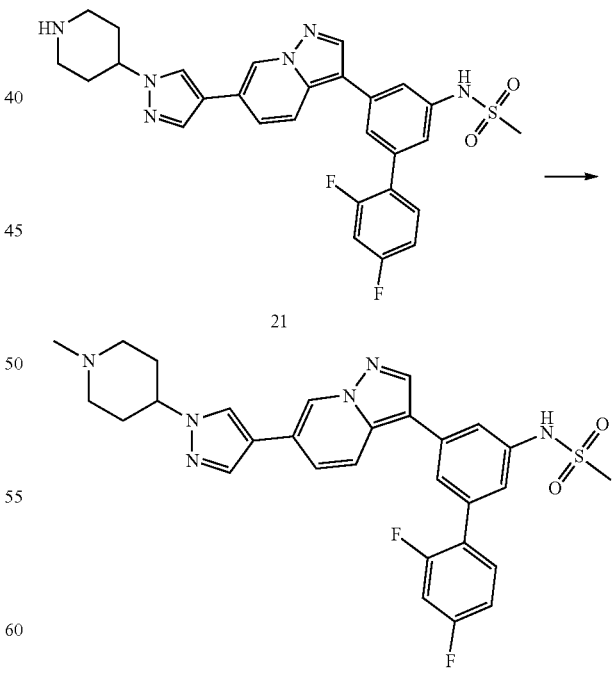

Step 1

Compound 21 (150 mg, 273.42 μmol), glacial acetic acid (32.84 mg, 546.84 μmol, 31.28 μL), and formaldehyde (110.94 mg, 1.37 mmol, 101.78 μL, 37% purity) were added to THF (3 mL), and the reaction solution was stirred at 25° C. for 0.5 hour. Then sodium cyanoborohydride (85.91 mg, 1.37 mmol) was added to the reaction solution, and the reaction solution was reacted at 25° C. for 2 hours. The reaction solution was extracted with 30 mL of water and ethyl acetate (30 mL*2). The organic phase was washed with 30 mL of saturated brine, dried over anhydrous sodium sulfate, filtered, and concentrated under reduced pressure.

The crude was purified by preparative high performance liquid chromatography (chromatographic column: Phenomenex Gemini-NX C18 75*30 mm*3 μm; mobile phase: [water (10 mM ammonium bicarbonate)-acetonitrile]; B (acetonitrile) %: 37%-57%, 10.5 min) to obtain compound 30.

LCMS (ESI) m/z: 563.3 [M+1]$^+$ $^1$H NMR (400 MHz, DMSO-d$_6$) δ 10.01 (s, 1H), 9.09 (s, 1H), 8.41 (d, J=8.8 Hz, 2H), 8.07 (s, 1H), 7.95 (d, J=9.2 Hz, 1H), 7.68-7.70 (m, 3H), 7.39-7.54 (m, 1H), 7.22-7.22 (m, 3H), 4.11-4.22 (m, 1H), 3.34 (s, 3H), 2.87-3.10 (m, 2H), 2.23 (s, 3H), 1.96-2.15 (m, 6H).

Example 31

Synthetic Route

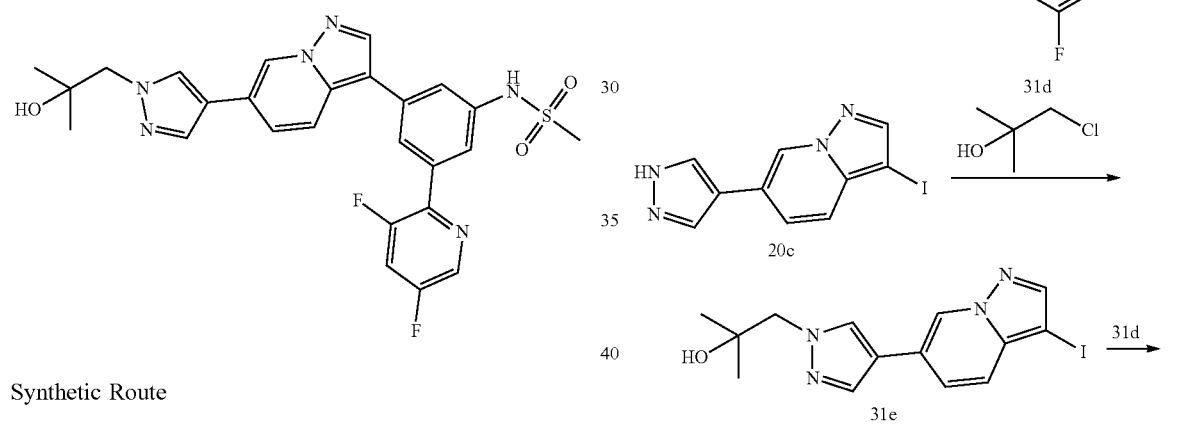

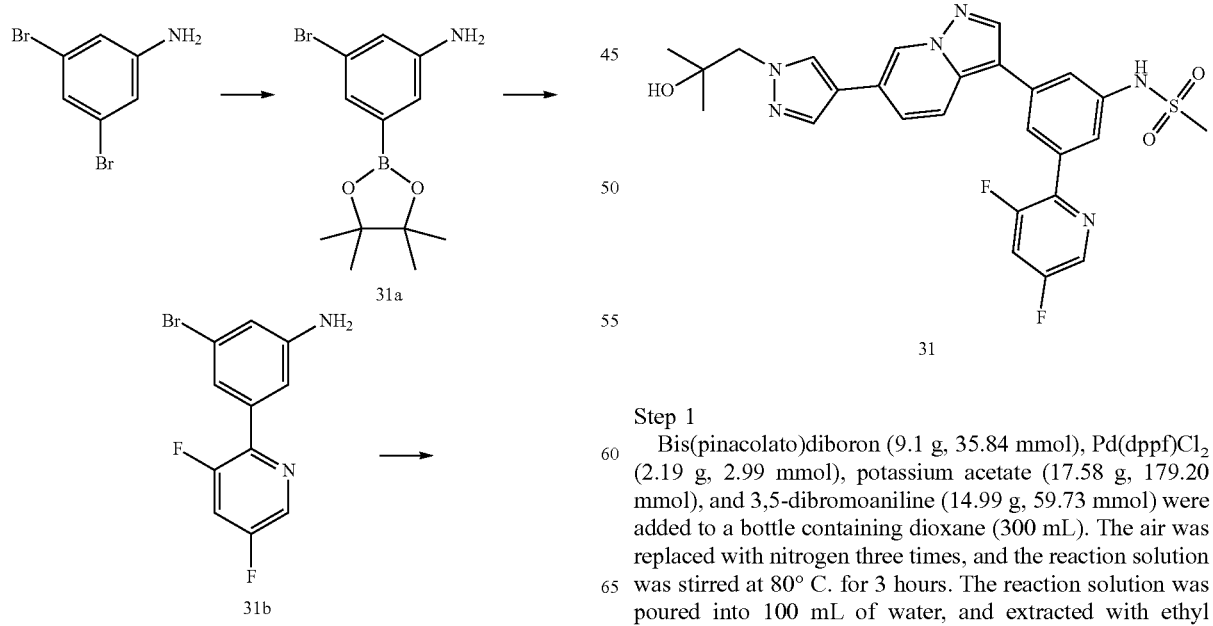

Step 1

Bis(pinacolato)diboron (9.1 g, 35.84 mmol), Pd(dppf)Cl$_2$ (2.19 g, 2.99 mmol), potassium acetate (17.58 g, 179.20 mmol), and 3,5-dibromoaniline (14.99 g, 59.73 mmol) were added to a bottle containing dioxane (300 mL). The air was replaced with nitrogen three times, and the reaction solution was stirred at 80° C. for 3 hours. The reaction solution was poured into 100 mL of water, and extracted with ethyl acetate (50 mL*3). The organic phase was dried, filtered, and concentrated under reduced pressure. The crude product was separated and purified by column (petroleum ether to petroleum ether:ethyl acetate=20:1) to obtain compound 31a.

LCMS (ESI) m/z: 298.0 [M+1]+

Step 2

Compound 31a (6 g, 20.14 mmol), 2-bromo-3,5-difluoropyridine (4.69 g, 24.16 mmol), sodium carbonate (5.34 g, 50.34 mmol), and Pd(dppf)Cl$_2$·CH$_2$Cl$_2$ (1.64 g, 2.01 mmol) were added to a bottle containing dioxane (150 mL) and water (40 mL). The air was replaced with nitrogen three times, and the reaction solution was stirred at 90° C. for 12 hours. The reaction solution was poured into 50 mL of water, and extracted with ethyl acetate (50 mL*3). The organic phase was dried, filtered, and concentrated under reduced pressure. The crude product was separated and purified by column (petroleum ether to petroleum ether:ethyl acetate=10:1) to obtain compound 31b.

LCMS (ESI) m/z: 285.1 [M+1]+

Step 3

Compound 31b (3.5 g, 12.28 mmol), bis(neopentyl glycolato)diboron (5.55 g, 24.55 mmol), Pd(PPh$_3$)$_2$Cl$_2$ (861.72 mg, 1.23 mmol), and potassium acetate (3.61 g, 36.83 mmol) were added to a bottle containing dioxane (70 mL). The air in the headspace of the bottle was replaced with nitrogen three times, and the reaction solution was stirred at 80° C. for 2 hours. The reaction solution was poured into 50 mL of water, and extracted with ethyl acetate (50 mL*2). The organic phase was dried, filtered, and concentrated under reduced pressure. The crude was separated and purified by column (petroleum ether to petroleum ether:ethyl acetate=4:1) to obtain compound 31c.

LCMS (ESI) m/z boric acid: MS=251.2 [M+1]+

Step 4

Compound 31c (2.5 g, 7.86 mmol) was dissolved in pyridine (20 mL), and methylsulfonyl chloride (2.39 g, 20.86 mmol, 1.61 mL) was added dropwise thereto. The reaction solution was stirred at 25° C. for 1 hour. Water (300 mL) was added to the reaction solution, and a large number of solids were precipitated. The resulting mixture was filtered, and the filter cake was subjected to rotary evaporation by means of azeotropic drying of toluene (10 mL*2) and water to obtain compound 31d.

LCMS (ESI) m/z boric acid: MS=329.1 [M+1]+

Step 5

Compound 20c (0.3 g, 967.45 μmol) and 1-chloro-2-methyl-2-propanol (157.55 mg, 1.45 mmol) were added to N,N-dimethylformamide (5 mL), and then potassium carbonate (401.12 mg, 2.90 mmol) was added thereto. The reaction solution was stirred at 80° C. for 12 hours. 100 mL of ethyl acetate and 200 mL of water were added to the reaction solution for phase separation. The organic phase was washed with 300 mL of half-saturated brine, dried, filtered and concentrated under reduced pressure. The crude was purified by column chromatography (dichloromethane:methanol=1:0 to 10:1) to obtain compound 31e.

LCMS (ESI) m/z: 383.1 [M+1]+

Step 6

Compound 31e (0.09 g, 235.48 μmol), compound 31d (111.96 mg, 282.58 μmol), potassium carbonate (97.63 mg, 706.44 μmol) and Pd(dppf)Cl$_2$ (19.23 mg, 23.55 μmol) were added to water (1 mL) and acetonitrile (1 mL). The air was replaced with nitrogen three times, and then the reaction solution was stirred at 60° C. for 2 hours. The reaction solution was concentrated under reduced pressure to remove acetonitrile, and then 200 mL of ethyl acetate and 300 mL of water were added thereto for extraction and phase separation. The organic phase was dried, filtered and concentrated under reduced pressure. The crude was purified by column chromatography (dichloromethane:methanol=50:1 to 10:1) to obtain compound 31.

LCMS (ESI) m/z: 539.1 [M+1]+

$^1$H NMR (400 MHz, DMSO-d$_6$) δ10.09-9.87 (m, 1H), 9.11 (s, 1H), 8.70 (m, 1H), 8.37 (m, 1H), 8.27 (m, 1H), 8.19-8.04 (m, 2H), 8.02-7.83 (m, 2H), 7.79-7.59 (m, 3H), 4.84-4.69 (m, 1H), 4.13-3.95 (m, 2H), 3.13-3.02 (m, 3H), 1.21-1.00 (m, 6H).

The compounds in Table 6 can be prepared by referring to the steps and methods similar to those in the route for the aforementioned example 31. Particularly, compound 36 is synthesized by referring to the steps and methods similar to those in the route for example 30 with compound 37 as the starting raw material. The trifluoroacetate salt or hydrochloride salt of the obtained compound was added to a sodium bicarbonate solution, and extracted with ethyl acetate. The organic phase was dried over anhydrous sodium sulfate, and concentrated under reduced pressure to obtain the compound.

TABLE 6

| Product no. | Product structure | Raw material A | Product LCMS m/z: [M + 1]+ | Product $^1$H NMR |
|---|---|---|---|---|
| Example 32 | 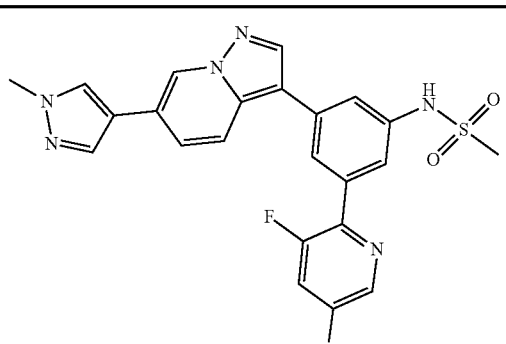 | 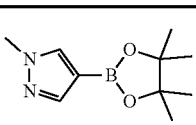 | 481.0 | Trifluoroacetate salt of compound 32: $^1$H NMR (400 MHz, CD$_3$OD) δ 8.81 (s, 1H), 8.55 (s, 1H), 8.26 (s, 1H), 8.10 (s, 1H), 7.95-7.99 (m, 3H), 7.73-7.78 (m, 2H), 7.68 (s, 1H), 7.61 (d, J = 8.0 Hz, 1H), 3.98 (s, 3H), 3.09 (s, 3 H). |

TABLE 6-continued

| Product no. | Product structure | Raw material A | Product LCMS m/z: [M + 1]+ | Product ¹H NMR |
|---|---|---|---|---|
| Example 34 | | HO-CH₂-CH(OH)-CH₂-Br | 541.3 | Compound 34: ¹H NMR (400 MHz, DMSO-d₆) δ9.98 (s, 1H), 9.10 (s, 1H), 8.70 (s, 1H), 8.37-8.29 (m, 2H), 8.07-8.12 (m, 2H), 7.88-7.95 (m, 2H), 7.64-7.70 (m, 3H), 5.02 (s, 1H), 4.76 (s, 1H), 4.24-4.28 (d, J = 12.4 Hz, 1H), 3.98-4.03 (m, 2H), 3.09 (s, 3 H), 1.23 (s, 2H). |
| Example 35 | | cyclopropyl-B(OH)₂ | 441.0 | Compound 35: ¹H NMR (400 MHz, DMSO-d₆) δ 9.89-10.06 (m, 1H), 8.55-8.75 (m, 2H), 8.24-8.36 (m, 1H), 8.04-8.18 (m, 1H), 7.78-7.89 (m, 2H), 7.55-7.70 (m, 2H), 7.09-7.23 (m, 1H), 3.01-3.13 (m, 3H), 1.93-2.10 (m, 1H), 0.89-1.05 (m, 2H), 0.74-0.87 (m, 2H). |
| Example 37 | | Boc-N-piperidin-4-ol | 550.3 | Hydrochloride salt of compound 37: ¹H NMR (400 MHz, DMSO-d₆) δ 10.03 (s, 1H), 9.15 (s, 1H), 8.88-8.90 (m, 1H), 8.69 (s, 1H), 8.44 (s, 1H), 8.38 (s, 1H), 8.10-8.15 (m, 2H), 7.97 (d, J = 9.6 Hz, 1H), 7.88 (s, 1H), 7.73 (d, J = 9.6 Hz, 1H), 7.67 (s, 2H), 4.50-4.55 (m, 1H), 3.39-3.42 (m, 2H), 3.12-3.16 (m, 2H), 3.09 (s, 3 H), 2.17-2.32 (m, 4H). |
| Example 36 | | HCHO | 564.3 | Compound 36: ¹H NMR (400 MHz, DMSO-d₆) δ 9.98 (s, 1H), 9.10 (s, 1H), 8.69 (d, J = 2.0 Hz, 1H), 8.43 (s, 1H), 8.37 (s, 1H), 8.07-8.15 (m, 2H), 7.94 (d, J = 9.2 Hz, 1H), 7.89 (s, 1H), 7.64-7.72 (m, 3H), 4.13-4.15 (m, 1H), 3.09 (s, 3H), 2.87-2.90 (d, J = 11.2 Hz, 2H), 2.23 (s, 3H), 1.97-2.12 (m, 6H). |
| Example 38 | | morpholine-CH₂CH₂-Cl | 580.3 | Compound 38: ¹H NMR (400 MHz, DMSO-d₆) δ 9.97-10.01 (m, 1H), 9.09 (s, 1H), 8.70(d, J = 2.4 Hz, 1H), 8.36 (d, J = 5.6 Hz, 2H), 8.06-8.15 (m, 2H), 7.95 (d, J = 9.6 Hz, 1 H), 7.87 (s, 1H), 7.64-7.69 (m, 3H), 4.26 (t, J = 6.8 Hz, 2H), 3.57 (t, J = 4.4 Hz, 4 H), 3.08 (s, 3H), 2.76 (t, J = 6.8 Hz, 2H), 2.43-2.44 (m, 4 H). |

TABLE 6-continued

| Product no | Product structure | Raw material A | Product LCMS m/z: [M + 1]+ | Product ¹H NMR |
|---|---|---|---|---|
| Example 39 | | | 567.3 | Compound 39: ¹H NMR (400 MHz, DMSO-d₆) δ 9.99 (s, 1H), 9.11 (s, 1H), 8.69 (s, 1H), 8.37 (s, 1H), 8.32 (s, 1H), 8.06-8.16 (m, 2H), 7.91-7.97 (m, 1H), 7.82-7.90 (m, 1H), 7.61-7.74 (m, 3H), 4.16-4.22 (m, 2H), 3.71-3.81 (m, 2H), 3.62-3.68 (m, 1H), 3.52-3.61 (m, 1H), 3.41-3.51 (m, 1H), 3.26-3.31 (m, 1H), 3.12-3.16 (m, 1H), 3.07-3.11 (m, 3H). |
| Example 40 | | | 587.3 | Compound 40: ¹H NMR (400 MHz, DMSO-d₆) δ 10.00 (s, 1H), 9.12 (s, 1H), 8.70 (d, J = 2.0 Hz, 1H), 8.38 (s, 2H), 8.11-8.15 (m, 2H), 7.96 (d, J = 9.2 Hz, 1H), 7.88 (s, 1H), 7.64-7.71 (m, 3H), 4.31 (t, J = 7.0 Hz, 2H), 3.13-3.16 (m, 2H), 3.09 (s, 3H), 3.01 (s, 3H), 2.24-2.27 (m, 2H). |
| Example 44 | | | 566.2 | N/A |
| Example 45 | | | 656.3 | Compound 45: ¹H NMR (400 MHz, DMSO-d₆) δ 9.95-10.05 (m, 1H), 9.05-9.14 (m, 1H), 8.66-8.72 (m, 1H), 8.33-8.42 (m, 2H), 8.06-8.17 (m, 2H), 7.91-7.99 (m, 1H), 7.85-7.90 (m, 1H), 7.60-7.73 (m, 3H), 7.18-7.41 (m, 5H), 4.46-4.60 (m, 1H), 4.27-4.42 (m, 1H), 3.93-4.10 (m, 1H), 3.68-3.85 (m, 1H), 3.43 (br s, 4H), 3.27-3.38 (m, 3H), 2.87-2.99 (m, 1H), 2.64-2.81 (m, 1H), 2.16-2.30 (m, 1H). |

Example 41

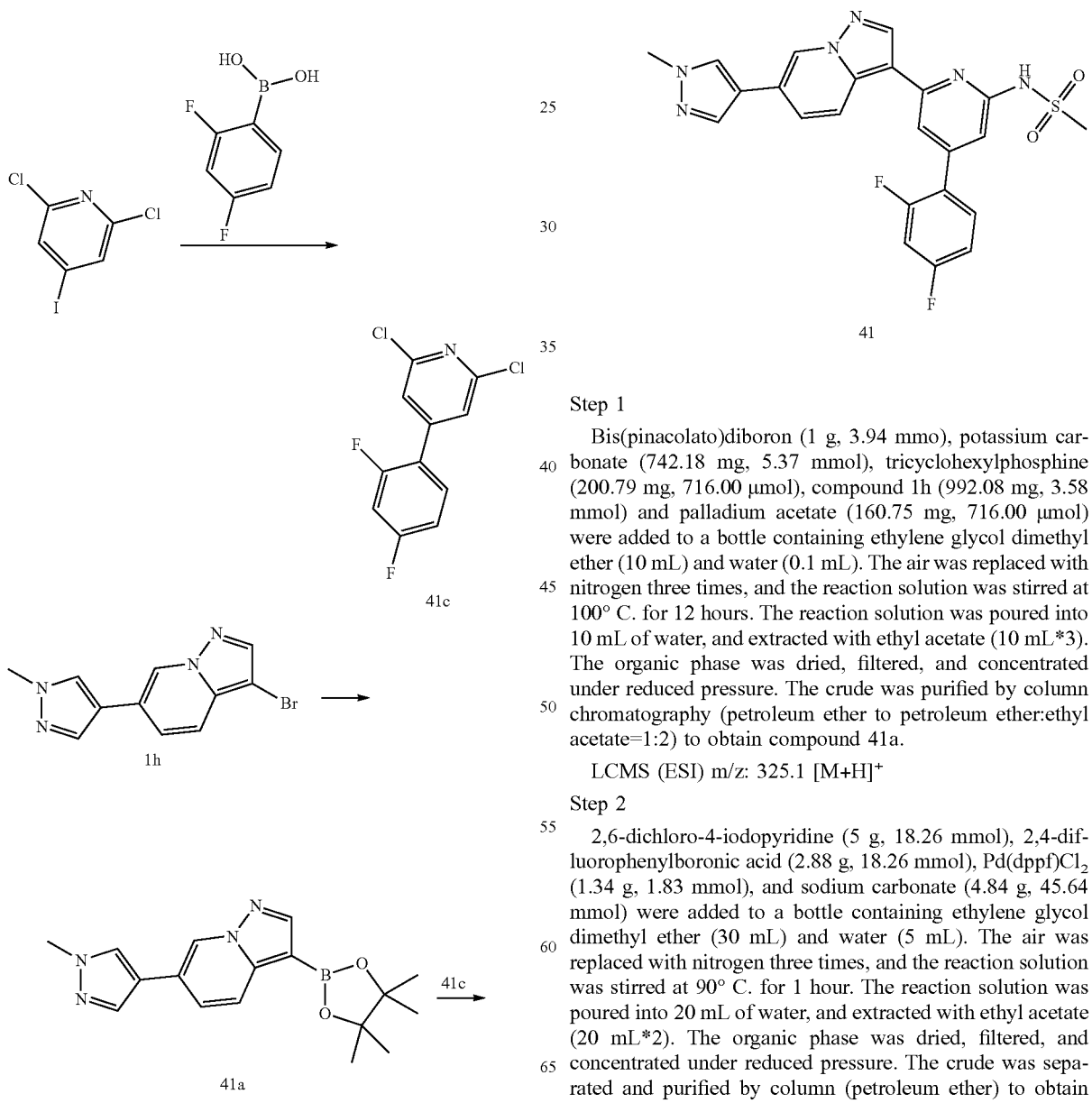

Synthetic Route

Step 1

Bis(pinacolato)diboron (1 g, 3.94 mmo), potassium carbonate (742.18 mg, 5.37 mmol), tricyclohexylphosphine (200.79 mg, 716.00 μmol), compound 1h (992.08 mg, 3.58 mmol) and palladium acetate (160.75 mg, 716.00 μmol) were added to a bottle containing ethylene glycol dimethyl ether (10 mL) and water (0.1 mL). The air was replaced with nitrogen three times, and the reaction solution was stirred at 100° C. for 12 hours. The reaction solution was poured into 10 mL of water, and extracted with ethyl acetate (10 mL*3). The organic phase was dried, filtered, and concentrated under reduced pressure. The crude was purified by column chromatography (petroleum ether to petroleum ether:ethyl acetate=1:2) to obtain compound 41a.

LCMS (ESI) m/z: 325.1 [M+H]+

Step 2

2,6-dichloro-4-iodopyridine (5 g, 18.26 mmol), 2,4-difluorophenylboronic acid (2.88 g, 18.26 mmol), Pd(dppf)Cl$_2$ (1.34 g, 1.83 mmol), and sodium carbonate (4.84 g, 45.64 mmol) were added to a bottle containing ethylene glycol dimethyl ether (30 mL) and water (5 mL). The air was replaced with nitrogen three times, and the reaction solution was stirred at 90° C. for 1 hour. The reaction solution was poured into 20 mL of water, and extracted with ethyl acetate (20 mL*2). The organic phase was dried, filtered, and concentrated under reduced pressure. The crude was separated and purified by column (petroleum ether) to obtain compound 41c.

Step 3

Compound 41a (150 mg, 462.70 μmol), compound 41c (240.67 mg, 925.40 μmol), tricyclohexylphosphine (45.41 mg, 161.94 μmol), potassium phosphate (294.65 mg, 1.39 mmol), and $Pd_2(dba)_3$ (84.74 mg, 92.54 μmol) were added to a bottle containing N,N-dimethylformamide (15 mL), and the reaction solution was reacted on a microwave instrument at 100° C. for 1 hour. The reaction solution was poured into 50 mL of half-saturated brine, and extracted with ethyl acetate (20 mL*2). The organic phases were combined, washed with half-saturated brine (20 mL*2), dried, filtered and concentrated under reduced pressure. The crude was slurried with 15 mL of methyl tert-butyl ether, and filtered off with suction. The filter cake was rinsed with 15 mL of methyl tert-butyl ether, and concentrated to remove the residual methyl tert-butyl ether to obtain compound 41b.

LCMS (ESI) m/z: 422.0 [M+H]$^+$

Step 4

Compound 41b (25 mg, 59.27 μmol), methylsulfonamide (22.55 mg, 237.06 μmol), cesium carbonate (57.93 mg, 177.80 μmol), palladium acetate (6.65 mg, 29.63 μmol), and Xantphos (17.15 mg, 29.63 μmol) were added to a sealed tube containing 1,4 dioxane (5 mL). The air was replaced with nitrogen three times, and the reaction solution was stirred at 120° C. for 2 hours. The reaction solution was concentrated to dryness under reduced pressure. The crude was separated by chromatographic column (Waters Xbridge BEH C18 100*30 mm*10 μm; mobile phase: [water (10 mM ammonium bicarbonate)-acetonitrile]; B (acetonitrile) %: 25%-60%, 8 min) to obtain compound 41.

LCMS (ESI) m/z: 481.2 [M+H]

$^1$H NMR (400 MHz, DMSO-d$_6$) δ 10.84 (brs, 1H), 9.07 (s, 1H), 8.84-8.86 (m, 1H), 8.74 (s, 1H), 8.32 (s, 1H), 8.07 (s, 1H), 7.75-7.77 (m, 1H), 7.66-7.69 (m, 2H), 7.45-7.50 (m, 1H), 7.30-7.45 (m, 1H), 6.84 (s, 1H), 3.89 (s, 3H), 3.57 (s, 3H).

The compounds in Table 7 can be prepared by referring to the steps and methods similar to those in the route for the aforementioned example 41.

TABLE 7

| Product no. | Product structure | Raw material A | Product LCMS m/z: [M + 1]$^+$ | Product $^1$H NMR |
|---|---|---|---|---|
| Example 42 | (structure) | H$_2$N-sulfonyl-cyclopropyl | 507.3 | Compound 42: $^1$H NMR (400 MHz, DMSO-d$_6$) δ 10.79 (brs, 1H), 9.06 (s, 1H), 8.95 (d, J = 5.6 Hz, 1H), 8.74 (s, 1H), 8.34 (s, 1H), 8.08 (s, 1H), 7.76-7.78 (m, 1H), 7.68-7.69 (m, 2H), 7.45-7.48 (m, 1H), 7.28-7.32 (m, 1H), 6.91 (s, 1H), 3.89 (s, 3H), 3.66 (d, J = 4.8 Hz, 1H), 1.09-1.12 (m, 2H), 1.01-1.03 (m, 2H). |
| Example 43 | (structure) | H$_2$N-sulfonyl-ethyl | 495.3 | Compound 43: $^1$H NMR (400 MHz, DMSO-d$_6$) δ 10.74 (brs, 1H), 9.06 (s, 1H), 8.83 (d, J = 9.2 Hz, 1H), 8.73 (s, 1H), 8.32 (s, 1H), 8.06 (s, 1H), 7.75-7.77 (m, 1H), 7.68-7.69 (m, 2H), 7.47-7.49 (m, 1H), 7.30-7.32 (m, 1H), 6.84 (s, 1H), 3.89 (s, 3H), 3.52-3.58 (m, 2H), 1.26-1.30 (m, 3H). |

Example 47

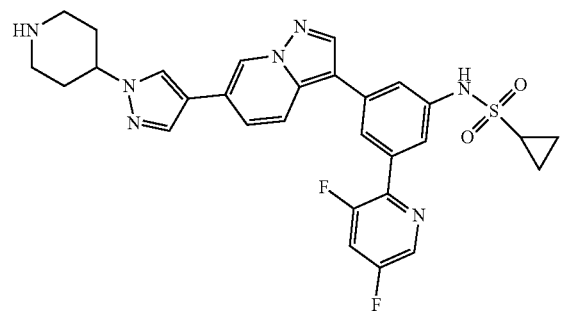 [SMILES: O=S(=O)(Nc1cc(-c2ncc(F)cc2F)cc(-c2cnn3cc(-c4cnn(C5CCNCC5)c4)ccc23)c1)C1CC1]

Synthetic Route
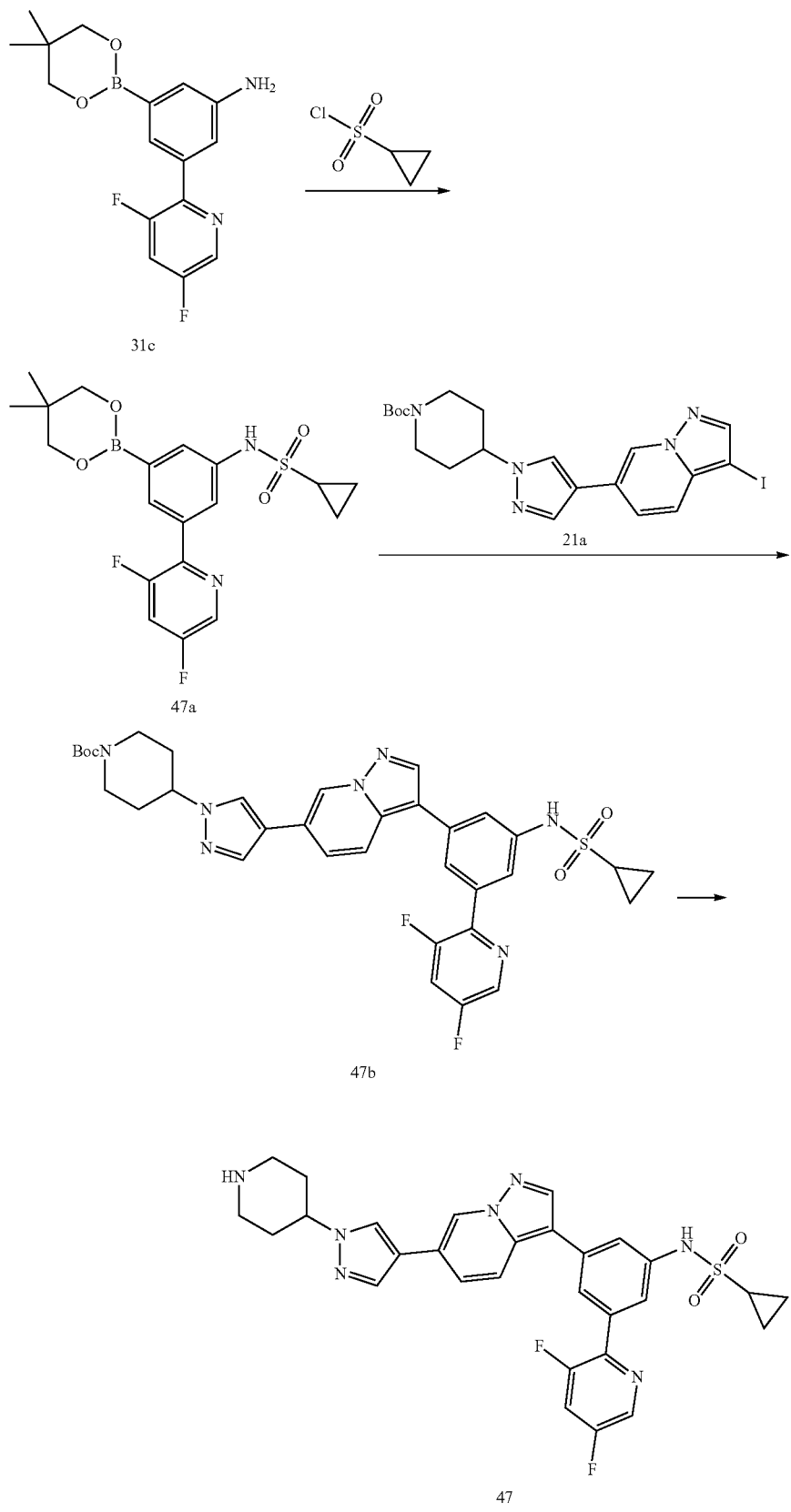

Step 1

Compound 31c (0.2 g, 628.68 μmol) was dissolved in pyridine (5 mL), and then cyclopropylsulfonyl chloride (176.77 mg, 1.26 mmol) was added thereto. The reaction solution was stirred at 25° C. for 2 hours. To the reaction solution were added ethyl acetate (100 mL) and hydrochloric acid (1 N, 100 mL) for extraction and phase separation. The organic phase was dried, filtered and concentrated to obtain a crude. The crude was purified by column chromatography (petroleum ether:ethyl acetate=10:1) to obtain compound 47a.

LCMS (ESI) m/z: 355.0 [M−68+1]$^+$

Step 2

Compound 47a (123.25 mg, 291.89 μmol), compound 21a (0.12 g, 243.24 μmol), potassium carbonate (100.85 mg, 729.72 μmol) and 1,1-bis(diphenylphosphino)ferrocene palladium chloride dichloromethane (19.86 mg, 24.32 μmol) were added to acetonitrile (5 mL) and water (5 mL). The air was replaced with nitrogen three times, and then the reaction solution was stirred at 60° C. for 2 hours. The reaction solution was concentrated under reduced pressure to remove acetonitrile, and then ethyl acetate (200 mL) and water (300 mL) were added thereto for extraction and phase separation. The organic phase was dried, filtered and concentrated under reduced pressure to obtain a crude. The crude was separated and purified by TLC plate (petroleum ether:ethyl acetate=1:1) to obtain compound 47b.

LCMS (ESI) m/z: 676.3 [M+1]$^+$

Step 3

Compound 47b (0.04 g, 59.19 μmol) was added to ethyl acetate (2 mL), and then hydrochloric acid/ethyl acetate (4 M, 5 mL, 337.87 eq) was added thereto. The reaction solution was stirred at 25° C. for 0.5 hour. The reaction solution was subjected to rotary evaporation, dissolved in methanol (2 mL), and purified by preparative high performance liquid chromatography (chromatographic column: Welch Xtimate C18 150*25 mm*5 μm; mobile phase: [water (0.04% HCl)-acetonitrile]; B (acetonitrile) %: 20%-50%, 8 min) to obtain the hydrochloride salt of compound 47.

LCMS (ESI) m/z: 576.4[M+1]$^+$ $^1$H NMR (400 MHz, DMSO-d$_6$) δ 9.97-10.01 (m, 1H), 9.11-9.15 (m, 1H), 8.88-8.93 (m, 1H), 8.67-8.70 (m, 1H), 8.40-8.44 (m, 1H), 8.34-8.37 (m, 1H), 8.12-8.15 (m, 1H), 7.90-7.96 (m, 1H), 7.84-7.88 (m, 1H), 7.70-7.75 (m, 1H), 7.64-7.70 (m, 2H), 4.47-4.58 (m, 2H), 3.37-3.45 (m, 2H), 3.06-3.16 (m, 2H), 2.71-2.77 (m, 1H), 2.12-2.26 (m, 4H), 1.49-1.54 (m, 1H), 0.93-1.03 (m, 4H).

Example 48

Synthetic Route

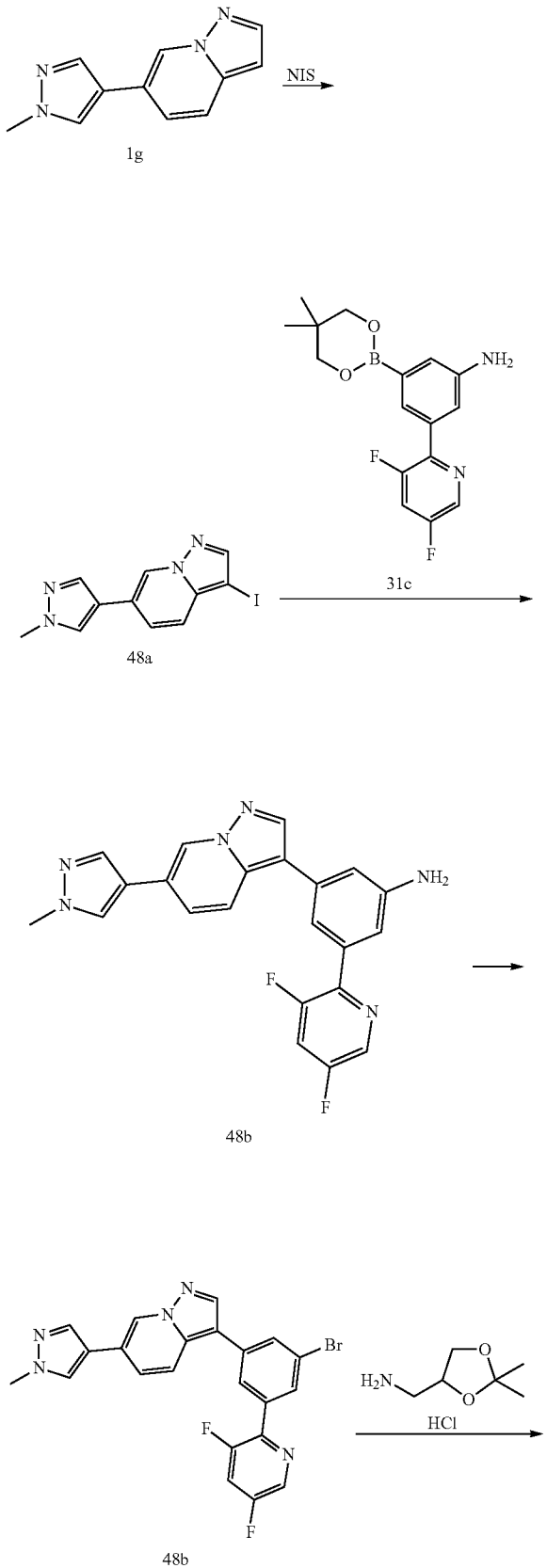

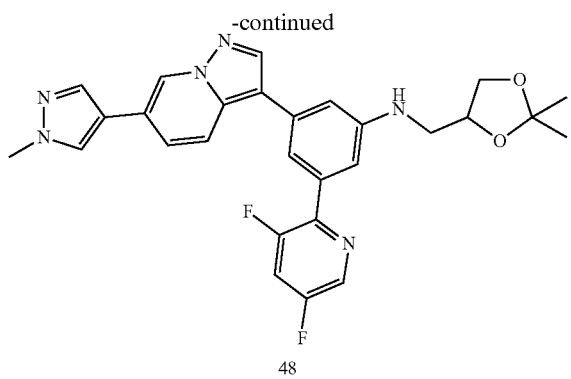
48

Step 1

Compound 1g (1.0 g, 5.04 mmol) was added to dichloromethane (10 mL), and N-iodosuccinimide (1.36 g, 6.05 mmol) was added to the reaction system. The reaction solution was stirred at 25° C. for 2 hours. To the reaction solution were added saturated sodium bicarbonate (100 mL) and dichloromethane (100 mL) for extraction and phase separation. The organic phase was dried, filtered and concentrated under reduced pressure to obtain compound 48a.

LCMS (ESI) m/z: 325.1[M+1]$^+$

Step 2

Compound 31c (1.35 g, 4.26 mmol), compound 48a (1.15 g, 3.55 mmol), potassium carbonate (1.47 g, 10.64 mmol) and 1,1-bis(diphenylphosphino)ferrocene palladium chloride dichloromethane (289.75 mg, 354.81 μmol) were added to acetonitrile (10 mL) and water (10 mL). The air was replaced with nitrogen three times, and the reaction solution was stirred at 60° C. for 2 hours. The reaction solution was concentrated under reduced pressure to remove acetonitrile, and ethyl acetate (50 mL) and water (50 mL) were added thereto for extraction and phase separation. The organic phase was dried, filtered and concentrated to obtain a crude. The crude was separated and purified by column (petroleum ether:ethyl acetate=1:1) to obtain compound 48b.

LCMS (ESI) m/z: 403.3[M+1]$^+$

Step 3

Compound 48b (0.8 g, 1.99 mmol) was added to a solution of hydrobromic acid in acetic acid (10 mL, 33% purity), and the reaction solution was stirred at 25° C. for 0.5 hour. The reaction solution was cooled to 0° C., and a solution of sodium nitrite (685.89 mg, 5.96 mmol) in water (10 mL) was slowly added thereto. The reaction solution was controlled at 0° C.-5° C., and stirred at 0° C.-5° C. for 0.5 hour. A solution of cuprous bromide (855.57 mg, 5.96 mmol, 181.65 μL) in acetic acid with hydrobromic acid (10 mL, 33% content) was added to the reaction system, and the reaction solution was stirred at 70° C. for 1 hour. The reaction solution was cooled to 15° C., and added to ice water (300 mL) and dichloromethane (300 mL*3) for extraction and phase separation. Then the organic phase was washed with saturated sodium bicarbonate (250 mL), dried, filtered and concentrated under reduced pressure. The crude was separated and purified by column (petroleum ether:ethyl acetate=1:1) to obtain compound 48c.

LCMS (ESI) m/z: 466.2/468.2[M+1]$^+$

Step 4

Compound 48c (0.1 g, 214.46 μmol) was added to toluene (2 mL), and then sodium tert-butoxide (61.83 mg, 643.39 μmol), (2,2-dimethyl-1,3-dioxolane-4-yl)methylamine hydrochloride (26.71 mg, 42.89 μmol) and tris(dibenzylideneacetone)dipalladium (19.64 mg, 21.45 μmol) were added thereto. The air was replaced with nitrogen three times, and the reaction solution was stirred at 100° C. for 2 hours. The reaction solution was concentrated to dryness under reduced pressure. The crude was purified by preparative high performance liquid chromatography (chromatographic column: Waters Xbridge BEH C18 100*30 mm*10 μm; mobile phase: [water (10 mM ammonium bicarbonate)-acetonitrile]; B (acetonitrile) %: 35%-60%, 8 min) to obtain compound 48.

LCMS (ESI) m/z: 517.4[M+1]$^+$ $^1$H NMR (400 MHz, DMSO-d$_6$) δ 9.00-9.08 (m, 1H), 8.61-8.67 (m, 1H), 8.25-8.34 (m, 2H), 8.00-8.10 (m, 2H), 7.90-7.98 (m, 1H), 7.55-7.64 (m, 1H), 7.29-7.36 (m, 1H), 7.00-7.09 (m, 2H), 5.99-6.07 (m, 1H), 4.25-4.35 (m, 1H), 4.04-4.13 (m, 1H), 3.85-3.93 (m, 3H), 3.68-3.78 (m, 1H), 3.23-3.29 (m, 2H), 1.35-1.41 (m, 3H), 1.27-1.33 (m, 3H).

The compounds in Table 8 can be prepared by referring to the steps and methods similar to those in the route for the aforementioned example 48.

TABLE 8

| Product no. | Product structure | Raw material A | Product LCMS m/z: [M + 1]$^+$ | Product $^1$H NMR |
|---|---|---|---|---|
| Example 49 | (structure shown) | (structure shown) | 475.4 | Compound 49: $^1$H NMR (400 MHz, DMSO-d$_6$) δ 9.01-9.09 (m, 1H), 8.61-8.68 (m, 1H), 8.23-8.32 (m, 2H), 8.01-8.11 (m, 2H), 7.92-7.99 (m, 1H), 7.56-7.63 (m, 1H), 7.25-7.32 (m, 1H), 7.08-7.14 (m, 1H), 7.01-7.07 (m, 1H), 5.66-5.75 (m, 1H), 4.50-4.57 (m, 1H), 3.83-3.98 (m, 3H), 3.02-3.12 (m, 2H), 1.16-1.28 (m, 6H). |

TABLE 8-continued
| Product no. | Product structure | Raw material A | Product LCMS m/z: [M + 1]+ | Product 1H NMR |
|---|---|---|---|---|
| Example 50 | 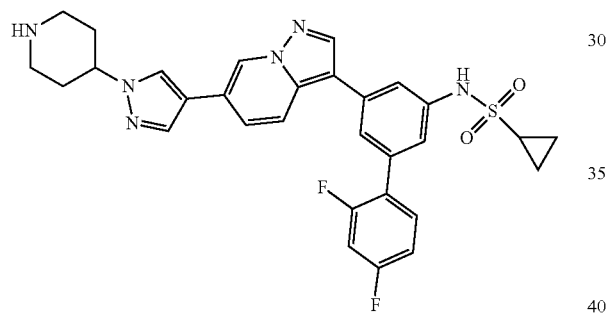 | | 477.4 | Compound 50: 1H NMR (400 MHz, DMSO-d6) δ 9.01-9.07 (m, 1H), 8.62-8.67 (m, 1H), 8.25-8.32 (m, 2H), 8.01-8.09 (m, 2H), 7.92-7.98 (m, 1H), 7.56-7.63 (m, 1H), 7.26-7.32 (m, 1H), 6.98-7.07 (m, 2H), 5.80-5.87 (m, 1H), 4.78-4.85 (m, 1H), 4.60-4.67 (m, 1H), 3.84-3.93 (m, 3H), 3.66-3.76 (m, 1H), 3.39-3.46 (m, 2H), 3.25-3.29 (m, 1H), 2.97-3.07 (m, 1H). |
Example 51
Synthetic Route
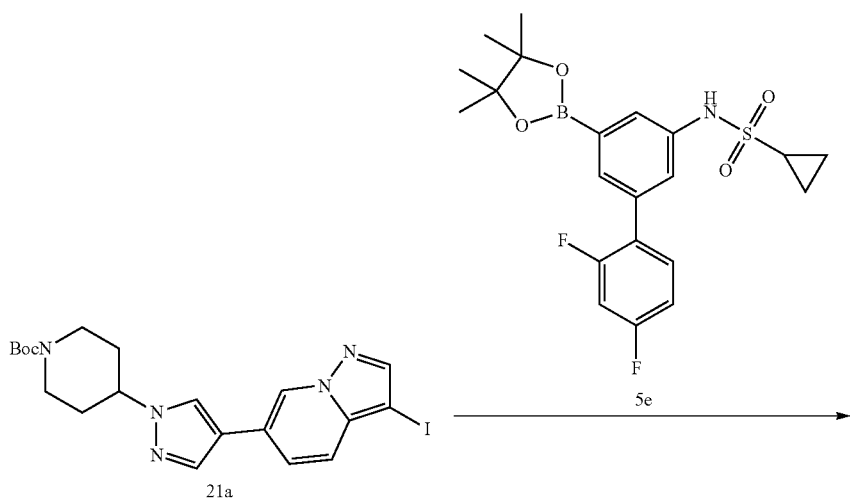

-continued

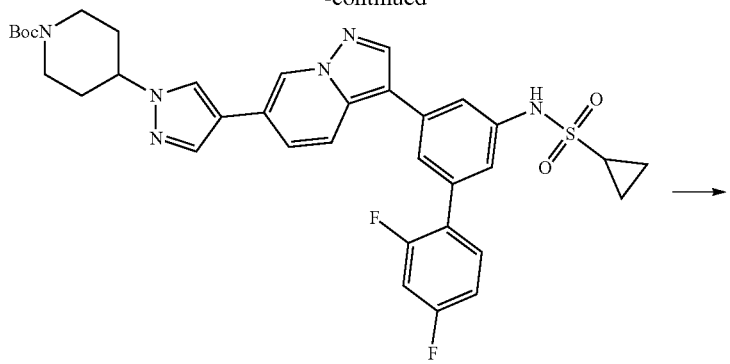

51a

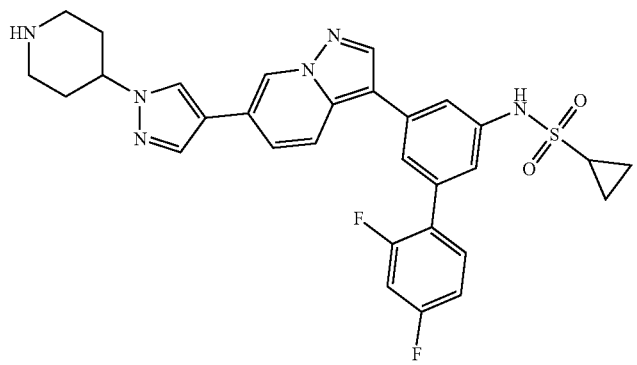

51

Step 1

Compound 21a (0.06 g, 121.62 μmol), compound 5e (79.41 mg, 182.43 μmol), potassium phosphate (77.45 mg, 364.86 μmol) and 1,1-bis(diphenylphosphino)ferrocene palladium chloride (8.90 mg, 12.16 μmol) were added to dioxane (2 mL) and water (2 mL). The air was replaced with nitrogen three times, and the reaction solution was stirred at 90° C. for 2 hours. To the reaction solution were added ethyl acetate (50 mL) and water (50 mL) for extraction and phase separation. The organic phase was dried, filtered and concentrated to obtain compound 51a.

LCMS (ESI) m/z: 675.4[M+1]$^+$

Step 2

Compound 51a (0.045 g, 66.69 μmol) was added to methanol (2 mL), and hydrochloric acid methanol (4 M, 2 mL) was added to the reaction system. The reaction solution was stirred at 25° C. for 1 hour. The reaction solution was concentrated to dryness under reduced pressure to obtain the hydrochloride salt of compound 51.

LCMS (ESI) m/z: 575.4[M+1]$^+$ $^1$H NMR (400 MHz, DMSO-d$_6$) δ 9.92-10.02 (m, 1H), 9.11-9.18 (m, 1H), 8.84-8.97 (m, 1H), 8.59-8.73 (m, 1H), 8.39-8.46 (m, 2H), 8.13-8.17 (m, 1H), 7.93-8.00 (m, 1H), 7.65-7.76 (m, 2H), 7.60-7.64 (m, 1H), 7.52-7.56 (m, 1H), 7.38-7.47 (m, 1H), 7.29-7.32 (m, 1H), 7.21-7.29 (m, 1H), 4.47-4.58 (m, 1H), 3.38-3.41 (m, 2H), 3.04-3.19 (m, 2H), 2.73-2.81 (m, 1H), 2.08-2.30 (m, 4H), 0.95-1.03 (m, 4H).

The hydrochloride salt of compound 51 was added to a sodium bicarbonate solution, and extracted with ethyl acetate. The organic phase was dried over anhydrous sodium sulfate and concentrated under reduced pressure to obtain compound 51.

Example 52

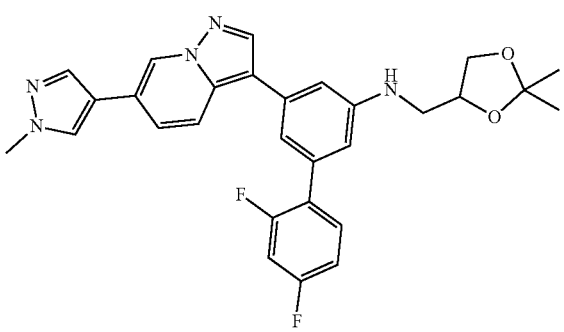

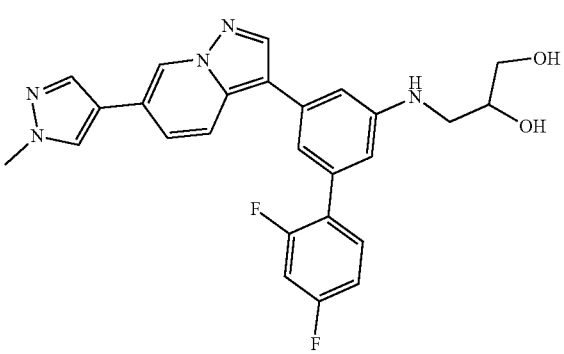

Synthetic Route

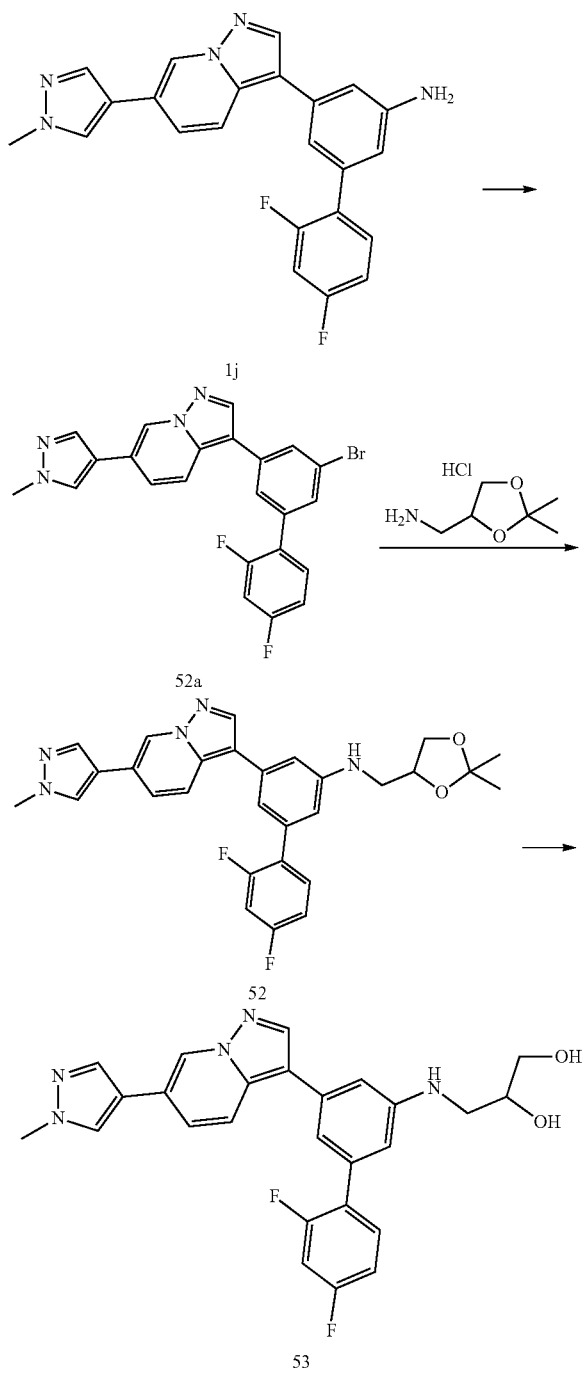

Step 1

Compound 1j (2.2 g, 5.48 mmol) was added to a solution of hydrogen bromide (30 mL, 33% purity) in water, and the reaction solution was stirred at 25° C. for 0.5 hour. The reaction solution was cooled to 0° C., and a solution of sodium nitrite (1.89 mg, 16.44 mmol) in water (20 mL) was slowly added thereto. The reaction solution was controlled at 0° C.-5° C., and stirred at 0° C.-5° C. for 0.5 hour. Then a solution of cuprous bromide (2.36 g, 16.44 mmol, 500.77 µL) in hydrogen bromide (20 mL, 33% purity) was added to the reaction solution, and the reaction solution was stirred at 70° C. for 1 hour. The reaction solution was cooled to 20° C., added to ice water (300 mL), and extracted with dichloromethane (300 mL*3). Then the organic phase was washed with saturated sodium bicarbonate (250 mL), dried, filtered and concentrated under reduced pressure. The crude was separated and purified by column (petroleum ether:ethyl acetate=1:0 to 1:1) to obtain compound 52a.

LCMS (ESI) m/z: 465.0 [M+1]$^+$

Step 2

(2,2-dimethyl-1,3-dioxolane-4-yl)methylamine hydrochloride (216.17 mg, 1.29 mmol, 214.03 µL, HCl) and compound 52a (0.5 g, 1.07 mmol) were added to toluene (10 mL), and then sodium tert-butoxide (309.81 mg, 3.22 mmol), tris(dibenzylideneacetone) dipalladium (133.82 mg, 214.92 µmol) and 4,5-bis(diphenylphosphino)-9,9-dimethylxanthene (98.40 mg, 107.46 µmol) were added thereto. The air was replaced with nitrogen three times, and the reaction solution was stirred at 100° C. for 2 hours. To the reaction solution were added ethyl acetate (200 mL) and water (100 mL) for extraction and phase separation. The organic phase was dried, filtered and concentrated under reduced pressure. The crude was purified by column chromatography (dichloromethane:methanol=100:1 to 10:1) to obtain a crude. The crude was purified by preparative high performance liquid chromatography (chromatographic column: Waters Xbridge Prep OBD C18 150*40 mm*10 µm; mobile phase: [water (10 mM ammonium bicarbonate)-acetonitrile]; B (acetonitrile) %: 45%-70%, 8 min) to obtain compound 52.

LCMS (ESI) m/z: 516.2[M+1]$^+$ $^1$H NMR (400 MHz, DMSO-d$_6$) δ 8.99-9.06 (m, 1H), 8.25-8.34 (m, 2H), 8.01-8.05 (m, 1H), 7.92-7.99 (m, 1H), 7.53-7.69 (m, 2H), 7.31-7.40 (m, 1H), 7.15-7.23 (m, 1H), 6.91-7.04 (m, 2H), 6.62-6.70 (m, 1H), 5.90-6.01 (m, 1H), 4.24-4.34 (m, 1H), 4.03-4.13 (m, 1H), 3.81-3.97 (m, 3H), 3.66-3.75 (m, 1H), 3.21-3.28 (m, 2H), 1.15-1.51 (m, 6H).

Step 3

Compound 52 (0.09 g, 174.57 µmol) was dissolved in sulfuric acid (33.18 g, 169.17 mmol, 18.03 mL, 50% purity), and the reaction solution was stirred at 70° C. for 2 hours. To the reaction solution were added a saturated sodium carbonate solution to adjust the pH to 8, and then ethyl acetate (200 mL) for extraction and phase separation. The organic phase was dried, filtered and concentrated under reduced pressure to obtain a crude. The crude was purified by TLC plate (ethyl acetate:methanol=10:1), followed by preparative high performance liquid chromatography (chromatographic column: Waters Xbridge BEH C18 100*30 mm*10 µm; mobile phase: [water (10 mM ammonium bicarbonate)-acetonitrile]; B (acetonitrile) %: 25%-55%, 8 min) to obtain compound 53.

LCMS (ESI) m/z: 476.2[M+1]$^+$ $^1$H NMR (400 MHz, DMSO-d$_6$) δ 8.98-9.09 (m, 1H), 8.22-8.36 (m, 2H), 7.89-8.09 (m, 2H), 7.48-7.72 (m, 2H), 7.28-7.42 (m, 1H), 7.13-7.25 (m, 1H), 6.87-7.07 (m, 2H), 6.56-6.72 (m, 1H), 5.65-5.87 (m, 1H), 4.72-4.87 (m, 1H), 4.51-4.67 (m, 1H), 3.80-4.02 (m, 3H), 3.63-3.76 (m, 1H), 3.36-3.49 (m, 3H), 2.93-3.11 (m, 1H).

The compounds in Table 9 can be prepared by referring to the steps and methods similar to those in the route for the aforementioned example 52.

TABLE 9

| Product no. | Product structure | Raw material A | Product LCMS m/z: [M + 1]+ | Product 1H NMR |
|---|---|---|---|---|
| Example 54 | | | 474.2 | Compound 54: $^1$H NMR (400 MHz, DMSO-$d_6$) δ 8.98-9.05 (m, 1H), 8.22-8.34 (m, 2H), 7.89-8.06 (m, 2H), 7.52-7.70 (m, 2H), 7.29-7.41 (m, 1H), 7.13-7.24 (m, 1H), 7.00-7.07 (m, 1H), 6.87-6.96 (m, 1H), 6.62-6.71 (m, 1H), 5.55-5.66 (m, 1H), 4.43-4.53 (m, 1H), 3.74-3.99 (m, 3H), 3.05 (d, J = 5.6 Hz, 2H), 1.05-1.31 (m, 6H). |

Biological Test Data:

Experimental Example 1: In Vitro Enzyme Activity Test of the Compounds of the Present Disclosure The $IC_{50}$ value was determined using $^{33}$P isotope-labeled kinase activity test (Reaction Biology Corp) to evaluate the inhibitory ability of the compounds to be tested on human FGFR1, FGFR2 and VEGFR2.

Buffer conditions: 20 mM Hepes (pH 7.5), 10 mM $MgCl_2$, 1 mM EGTA, 0.02% Brij35, 0.02 mg/mL BSA, 0.1 mM $Na_3VO_4$, 2 mM DTT, 1% DMSO.

Test steps: At room temperature, the compounds to be tested were dissolved in DMSO to prepare a 10 mM solution for use. The substrate was dissolved in the newly-prepared buffer, and the kinase to be tested was added thereto and mixed well. The DMSO solution in which the compounds to be tested were dissolved was added to the above-mentioned homogeneous reaction solution using acoustic technology (Echo 550). The concentrations of the compounds in the reaction solution were 3 μM, 1 μM, 0.333 μM, 0.111 μM, 37.0 nM, 12.3 nM, 4.12 nM, 1.37 nM, 0.457 nM, and 0.152 nM. After incubating for 15 minutes, to the reaction solution was added $^{33}$P-ATP (activity: 0.01 μCi/μL, with corresponding concentration listed in Table 10) to start the reaction. The concentration information of FGFR1 and KDR in the reaction solution was listed in Table 10. After the reaction was carried out at room temperature for 120 minutes, the reaction solution was spotted on P81 ion exchange filter paper (Whatman #3698-915). After the filter paper was repeatedly washed with 0.75% phosphoric acid solution, the radioactivity of the phosphorylated substrate remaining on the filter paper was measured. The kinase activity data was expressed by comparing the kinase activity of the groups containing the compounds to be tested with that of the blank group (containing only DMSO). The $IC_{50}$ value was obtained by curve fitting using Prism4 software (GraphPad), and the experimental results were shown in Table 11.

TABLE 10

Related information about kinases, substrates and ATP in in-vitro tests.

| Kinase | Kinase concentration in reaction solution (nM) | Substrate | Substrate concentration in reaction solution (mg/L) | ATP concentration (μM) |
|---|---|---|---|---|
| FGFR1 Supplier: Invitrogen Cat#: PV3146 Lot #: 28427Q | 1.5 | pEY (mg/L) + Mn Supplier: Sigma Cat#: P7244-250MG Lot #: 062K5104V | 0.2 mg/mL | 5 |
| FGFR2 Supplier: Invitrogen Cat#: PV3368 | 0.45 | pEY (mg/ml) + Mn Supplier: Sigma Cat#: P7244-250MG Lot #: 062K5104V | 0.2 mg/mL | 5 |
| VEGFR2 Supplier: Invitrogen Cat#: PR5992C Lot #: 36431DD | 1 | pEY (mg/L) + Mn Supplier: Sigma Cat#: P7244-250MG Lot #: 062K5104V | 0.2 mg/mL | 20 |

TABLE 11

IC$_{50}$ test results of the kinase activity of the compounds of the present disclosure

| Samples to be tested | FGFR1 IC$_{50}$ (nM) | FGFR2 IC$_{50}$ (nM) | VEGFR2 IC$_{50}$ (nM) |
|---|---|---|---|
| Trifluoroacetate salt of comparative example 1 | 22.2 | 29.9 | 27.2 |
| Compound 1 | 6.29 | N/A | 9.5 |
| Compound 2 | 2.86 | 2.66 | 4.39 |
| Compound 3 | 2.37 | N/A | 1.67 |
| Compound 4 | 1.63 | 2.5 | 1.05 |
| Compound 5 | 9.34 | N/A | 13.3 |
| Compound 6 | 17 | N/A | 23.9 |
| Compound 7 | 135 | N/A | 152 |
| Compound 8 | N/A | 65.3 | 213 |
| Trifluoroacetate salt of compound 9 | N/A | 73.3 | 92.3 |
| Trifluoroacetate salt of compound 10 | N/A | 36.5 | 48.3 |
| Trifluoroacetate salt of compound 11 | N/A | 0.76 | 0.6 |
| Compound 12 | N/A | 3.74 | 5.29 |
| Compound 13 | N/A | 2.98 | 12 |
| Compound 14 | 10.3 | N/A | 5.17 |
| Compound 15 | N/A | 287 | 479 |
| Compound 16 | N/A | 312 | 322 |
| Compound 17 | N/A | 142 | 199 |
| Compound 18 | N/A | 256 | 451 |
| Compound 19 | N/A | 88.6 | 73.7 |
| Compound 20 | N/A | 0.23 | 0.38 |
| Hydrochloride salt of compound 21 | N/A | 0.57 | 0.48 |
| Compound 22 | N/A | 4.38 | 1.88 |
| Compound 23 | N/A | 1.88 | 3.16 |
| Compound 24 | N/A | 10.1 | 14.7 |
| Compound 25 | N/A | 40.2 | 22.4 |
| Trifluoroacetate salt of compound 26 | N/A | 1.98 | 2.74 |
| Trifluoroacetate salt of compound 27 | N/A | 2.55 | 1.66 |
| Compound 28 | N/A | 359 | 439 |
| Trifluoroacetate salt of compound 29 | N/A | 3.98 | 2.98 |
| Compound 30 | N/A | 0.3 | 0.7 |
| Compound 31 | N/A | 1.79 | 1.35 |
| Trifluoroacetate salt of compound 32 | N/A | 1.09 | 1.38 |
| Trifluoroacetate salt of compound 33 | N/A | 1.21 | 2.33 |
| Compound 34 | N/A | 0.42 | 0.29 |
| Compound 35 | N/A | 49.2 | 20.6 |
| Compound 36 | N/A | 0.23 | 0.30 |
| Hydrochloride salt of compound 37 | N/A | 0.18 | 0.33 |
| Compound 38 | N/A | 0.72 | 0.58 |
| Compound 39 | N/A | 0.95 | 0.66 |
| Compound 40 | N/A | 0.77 | 1.99 |
| Compound 41 | N/A | 1.81 | 0.69 |
| Compound 42 | N/A | 1.06 | 1.17 |
| Compound 43 | N/A | 0.47 | 0.49 |
| Compound 44 | N/A | 0.72 | 1.4 |
| Compound 45 | N/A | 29.6 | 11.2 |
| Hydrochloride salt of compound 47 | N/A | 0.45 | 1.3 |
| Compound 48 | N/A | 0.95 | 8.39 |
| Compound 49 | N/A | 2.29 | 5.52 |
| Compound 50 | N/A | 1.05 | 3.82 |
| Hydrochloride salt of compound 51 | N/A | 1.27 | 15.3 |
| Compound 52 | N/A | 6.59 | 21.4 |
| Compound 53 | N/A | 5.59 | 3.63 |
| Compound 54 | N/A | 10.6 | 7.53 |

Note:
"N/A" means not tested.

Conclusion: The compounds of the present disclosure have excellent FGFR1, FGFR2, and VEGFR2 kinase activity.

Experimental Example 2: Cell Activity Test of Gastric Cancer Cell Line SNU-16 of the Compounds of the Present Disclosure Experimental Objective:

To test the inhibitory effect of the compounds on the proliferation of human gastric cancer SNU-16 cells expressing FGFR2.

Experimental Method:

The compounds used in the test were subjected to 3-fold concentration dilution, the concentration starting from 10 μM and subjected to 3-fold serial dilution, resulting in 9 concentrations: 10 μM, 2.50 μM, 0.62 μM, 0.156 μM, 39.1 nM, 9.8 nM, 2.4 nM, 0.61 nM, and 0.15 nM.

Instruments:

(1) Promega CellTiter-Glo luminescent cell viability assay kit (Promega-G7573).

(2) 2104 EnVision multi-tag reader, PerkinElmer.

Result Analysis:

The inhibition rate (IR) of the compounds tested was determined by the following formula: IR (%)=(1−(RLU compound-RLU blank)/(RLU control-RLU blank))*100%. The inhibition rate of different doses of the compounds would be calculated in the Excel file, and the IC$_{50}$ data was obtained by parametric curve fitting (GraphPad Software). The experimental results were shown in Table 12.

TABLE 12

IC$_{50}$ test results of the kinase activity of the compounds of the present disclosure

| Samples to be tested | SNU-16 IC$_{50}$ (nM) |
|---|---|
| Comparative example 1 | 62 |
| Compound 2 | 16.3 |
| Compound 4 | 14.5 |
| Trifluoroacetate salt of compound 11 | 10.5 |
| Compound 20 | 7.5 |
| Hydrochloride salt of compound 21 | 9.6 |
| Compound 22 | 28.5 |
| Compound 26 | 7.8 |
| Trifluoroacetate salt of compound 27 | 11.5 |
| Trifluoroacetate salt of compound 33 | 6.2 |

Conclusion: The compounds of the present disclosure have a significant inhibitory effect on cell proliferation in the SNU-16 cell activity test.

Experimental Example 3: Inhibition Test of hERG Potassium Ion Channel

Experimental Objective:

To detect the effect of the compounds of the present disclosure to be tested on the hERG potassium ion channel using a full-automatic patch clamp method.

Experimental Method:

1. Cell Preparation 1.1 CHO-hERG cells were cultured in a 175 cm$^2$ culture bottle, and once the cells grow to a density of 60% to 80%, the culture solution was removed; and the cells were washed with 7 mL of PBS (Phosphate Buffered Saline), and then digested by adding 3 mL of Detachin.

1.2 After the digestion was complete, 7 mL of culture solution was added for neutralization, and the mixture was centrifuged; and the supernatant was pipetted out, and then 5 mL of culture solution was added for resuspension to ensure that the cells reached a density of 2 to 5×10$^6$/mL.

2. Solution Preparation

TABLE 13

Components of intracellular fluid and extracellular fluid

| Reagent | Extracellular fluid (mM) | Intracellular fluid (mM) |
|---|---|---|
| CaCl$_2$ | 1 | 1 |
| MgCl$_2$ | 1.25 | 1 |

117

TABLE 13-continued

Components of intracellular fluid and extracellular fluid

| Reagent | Extracellular fluid (mM) | Intracellular fluid (mM) |
|---|---|---|
| KCl | 5 | 140 |
| NaCl | 140 | 0 |
| Glucose | 10 | 0 |
| HEPES | 10 | 10 |
| EGTA | 0 | 10 |
| pH | pH is adjusted to 7.4 with sodium hydroxide, | pH is adjusted to 7.4 with potassium hydroxide, |
| Osmotic pressure | 305 mOsm | 290 sm |

3. Electrophysiological Recording Process

The single-cell high-impedance sealing and the whole-cell mode formation process were all automatically completed by the Qpatch instrument. After the whole-cell recording mode was obtained, the cells were clamped at −80 millivolt; before a 5 second +40 millivolt depolarization stimulus was given, a 50 millisecond −50 millivolt pre-voltage was given, then repolarized to −50 millivolt for 5 seconds, and then returned to −80 millivolt. Such a voltage stimulus was applied every 15 seconds and recorded for 2 minutes, and then extracellular fluid was given and recorded for 5 minutes, followed by drug administration. The concentration of the compounds was tested from the lowest test concentration, each of which was tested for 2.5 minutes. After all the concentrations were given in turn, a positive control compound (3 μM Cisapride) was given. At least 3 cells were tested at each concentration (n>3).

4. Compound Preparation 4.1 The mother liquid of the compounds was diluted with DMSO, 10 μL of which was added to 20 μL of DMSO solution and subjected to 3-fold serial dilution to 6 DMSO concentrations.

4.2 4 μL of compounds with 6 DMSO concentrations were added to 396 μL of extracellular fluid respectively, and subjected to 100-fold dilution to 6 intermediate concentrations. Then 80 μL of compounds with 6 intermediate concentrations were added to 320 μL of extracellular liquid respectively, and subjected to 5-fold dilution to the final concentrations to be tested.

4.3 The highest test concentration was 40 μM, followed by 6 concentrations in order: 40 μM, 13.33 μM, 4.44 μM, 1.48 μM, 0.49 μM, and 0.16 μM.

4.4 The DMSO in the final test concentrations did not exceed 0.2%, and the DMSO at this concentration had no effect on the hERG potassium channel.

4.5 The compound preparation was carried out using the Bravo instrument to complete the entire dilution process.

5. Data Analysis

The experimental data was analyzed by GraphPad Prism 5.0 software.

6. Quality Control

Environment: Humidity 20% to 50%, temperature 22° C. to 25° C.

Reagents: The experimental reagents used were purchased from Sigma, with a purity of >98%.

The experimental data in the report must meet the following criteria: whole-cell sealing impedance>100 MΩ; tail current amplitude>300 pA.

Pharmacological parameters: The inhibitory effect of Cisapride at multiple concentrations on the hERG channel is set as a positive control.

7. Test Results

The hERG $IC_{50}$ values of the compounds of the examples were shown in Table 14.

TABLE 14

The hERG $IC_{50}$ values of the compounds of the examples

| Samples to be tested | hERG $IC_{50}$ (μM) |
|---|---|
| Compound 2 | >40 |
| Compound 5 | >40 |

Conclusion: The compounds of the present disclosure have no inhibitory effect on the hERG potassium ion channel, and an in vitro test thereof shows no safety risk of causing cardiotoxicity.

Experimental Example 4: Pharmacokinetic Studies

Experimental Objective:

To evaluate the pharmacokinetic behavior of the compounds of the present disclosure after Cassette intravenous injection and intragastric administration, and to investigate the bioavailability thereof after intragastric administration.

Experimental Operations:

Balb/c female mice aged 7 to 10 weeks were selected, and administered intravenously and orally with the doses of 0.2 mg/kg and 1 mg/kg, respectively. The mice were fasted for at least 12 hours before administration, and feeding was resumed after 4 hours of administration. The mice were free to drink water during the entire experiment. In this experiment, Cassette administration was used, and with regard to the intravenous injection group: an appropriate amount of each compound was weighed, and mixed with 5% DMSO/10% Solutol/85% Water for vortexing to prepare a 0.1 mg/mL of clear solution; the clear solution was filtered with a microporous membrane for later use; and with regard to the intragastric administration group: an appropriate amount of each compound was weighted, and mixed with 90% (25% HP-β-CD/10% Cremophor EL) with pH being adjusted to 4 to 5 to prepare a homogeneous suspension for later use. On the day of the experiment, the animals in the intravenous injection group were administrated with the corresponding compounds via tail vein single injection, with the administration volume of 2 mL/kg; and the animals in the oral group were administrated with the corresponding compounds by single intragastric administration, with the administration volume of 10 mL/kg. The body weight of the animals was weighed before administration, and the administration volume was calculated based on the body weight. The sample collection time was: 0.083 (injection group) h, 0.25 h, 0.5 h, 1 h, 2 h, 4 h, 8 h, and 24 h. Approximately 30 uL of whole blood was collected from the saphenous vein at each time point to prepare plasma for high performance liquid chromatography-tandem mass spectrometry (LC-MS/MS) to determine the concentration. All animals were euthanized by CO2 anesthesia after PK samples at the last time point were collected. The non-compartmental model of WinNonlin™ Version 6.3 (Pharsight, Mountain View, CA) pharmacokinetic software was used to process the plasma concentration, and the pharmacokinetic parameters were calculated using the linear logarithmic trapezoidal method.

Experimental Results:

The evaluation results of PK properties were shown in Table 15:

TABLE 15

Pharmacokinetic results of the compounds to be tested

| Dosage | Pharmacokinetic parameters | Compound 1 | Compound 2 | Compound 4 |
|---|---|---|---|---|
| IV (0.2 mg/kg) | Half-life $T_{1/2}$ (h) | 1.52 | 2.12 | 1.17 |
| | Clearance rate CL (ml/min/kg) | 8.53 | 6.53 | 12.6 |
| | Apparent volume of distribution $Vd_{ss}$ (L/kg) | 1.25 | 1.2 | 1.4 |
| | Area under the plasma concentration-time curve from time zero to 24 hours $AUC_{0-24\,h}$ (nM · h) | 751 | 1135 | 548 |
| PO (1 mg/kg) | Time to peak $T_{max}$ (h) | 2.0 | 2.0 | 2.0 |
| | Peak concentration $C_{max}$ (nM) | 540 | 388 | 463 |
| | Area under the plasma concentration-time curve AUC (nM · h) | 2480 | 1977 | 1898 |
| | Bioavailability F (%) | 74.0% | 43.8% | 73.2% |

Conclusion: The compounds of the present disclosure show a low drug clearance rate, and can quickly reach a peak and exhibit high oral absorption bioavailability after oral administration.

Experimental Example 5: Anti-Tumor Activity Test in an Animal Tumor Model In Vivo Experimental Objective:

To determine the anti-tumor effect of the compounds of the present disclosure in a mouse subcutaneous xenograft tumor model of human gastric cancer SNU-16

Experimental Method:

1) Preparation of Tumor Tissues preparation of tumor tissues: SNU-16 cells were routinely cultured in an RPMI-1640 culture medium containing 10% fetal bovine serum under the conditions of 5% $CO_2$, 37° C. and saturated humidity. According to cell growth, the cells were passaged or refilled 1 to 2 times a week with a passage ratio of 1:3 to 1:4.

2) Tissue Inoculation and Grouping

SNU-16 cells at the logarithmic growth phase were collected, counted and then resuspended in a 50% serum-free RPMI-1640 culture medium and 50% Matrigel, and adjusted to a cell concentration of $4 \times 10^7$ cells/mL; the cells were placed in an ice box, and the cell suspension was suctioned with a 1 mL syringe, and subcutaneously injected into the anterior right axillary of nude mice. Each animal was inoculated with 200 μL ($8 \times 10^6$ cells/mouse) to establish a SNU-16 xenograft model. The animal status was observed regularly, and the tumor diameter was measured with an electronic vernier caliper. The data was input into an Excel spreadsheet to calculate tumor volume and monitor tumor growth. Once the tumor volume reached 100 to 300 mm$^3$, tumor-bearing mice (tumor volume of 104 to 179 mm$^3$) with good health and similar tumor volume were selected and grouped by a randomized block method with 6 mice per group, and the administration was started when the average tumor volume of each group reached about 143 mm$^3$.

3) The tumor diameter was measured twice a week to calculate the tumor volume, and the animal body weight was weighted and recorded.

The calculation formula of tumor volume (TV) was: TV (mm$^3$)=1×w$^2$/2, where 1 represented the long diameter of the tumor (mm); w represented the short diameter of the tumor (mm).

The anti-tumor efficacy of the compounds was evaluated by TGI (%) or relative tumor proliferation rate T/C (%). Relative tumor proliferation rate T/C (%)=$T_{RTV}/C_{RTV} \times$ 100% ($T_{RTV}$: the mean RTV of the treatment group; $C_{RTV}$: the mean RTV of the negative control group). The relative tumor volume (RTV) was calculated according to the results of the tumor measurement. The calculation formula was RTV=$V_t/V_0$, where $V_0$ was the tumor volume measured at the beginning of the grouping and administration (i.e., D0), and $V_t$ was the tumor volume corresponding to a certain measurement in the mouse. $T_{RTV}$ and $C_{RTV}$ were obtained from the data on the same day.

TGI (%) reflected the tumor growth inhibition rate. Calculation of TGI (%): TGI (%)=[(1−(average tumor volume at the end of administration in a certain treatment group−average tumor volume at the beginning of administration in the treatment group))/(average tumor volume at the end of administration in the solvent control group−average tumor volume at the beginning of administration in the solvent control group)]×100%.

Figure 2:
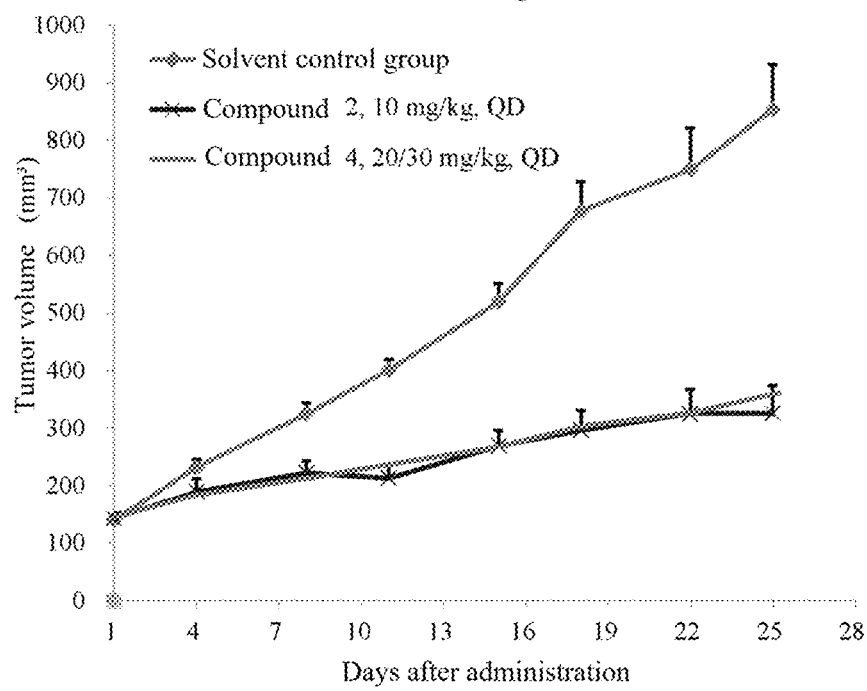
FIG. 2 is the mouse body weight curve during administration.

Experimental Results:

In the model of human gastric cancer allogeneic inhibitory tumor SNU-16, the compounds of the present disclosure showed significant anti-tumor activity compared with the solvent group after continuous administration for 25 days. The tumor growth inhibition rates (% TGI) were: 74% and 70% respectively; and the relative tumor proliferation rates (% T/C) were: 36% and 40%. The specific results were shown in Table 16, FIG. 1 and FIG. 2.

TABLE 16

Summary table of SNU-16 tumor growth inhibition rate and relative tumor proliferation rate

| Samples to be tested | Dosage (PO) | TGI (%) (tumor growth inhibition rate) on day 25 | T/C (%) (relative tumor proliferation rate) on day 25 | Specific P value compared with the solvent group |
|---|---|---|---|---|
| Compound 2 | 10 mpk/QD | 74% | 36% | P < 0.01 |
| Compound 4* | 20/30/20 mpk/QD | 70% | 40% | P < 0.01 |

*In the administration groups, the dosage on day 9 was changed to 30 mg/kg/day, and the dosage on day 12 was changed to 20 mg/kg/day.

Experimental conclusion: The compounds of the present disclosure show significant anti-tumor activity in a mouse model of human gastric cancer.

What is claimed is:

1. A compound represented by formula (III) or a pharmaceutically acceptable salt thereof,

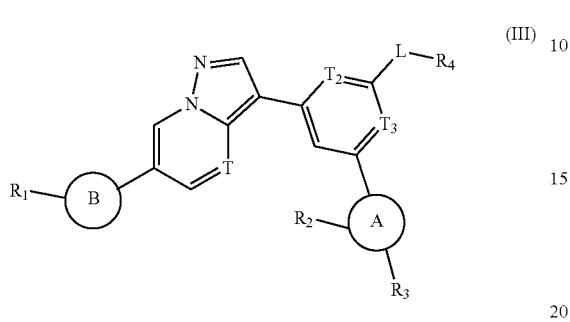

wherein,

T, $T_2$ and $T_3$ are each independently selected from N, and CH;

$R_1$ is selected from H, $C_{1-3}$ alkyl, tetrahydropyranyl, piperidinyl,

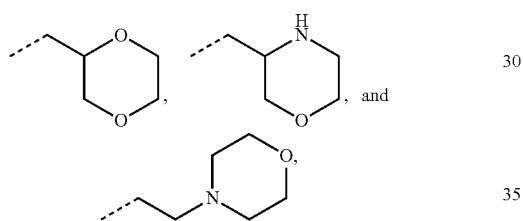

wherein the $C_{1-3}$ alkyl, tetrahydropyranyl, piperidinyl,

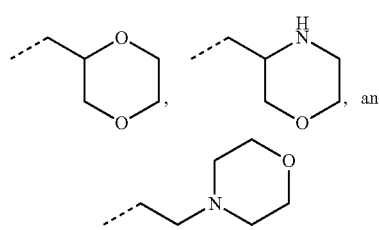

are optionally substituted with 1, 2 or 3 $R_a$, and further wherein ⌀ is used to denote a point of attachment;

$R_2$ and $R_3$ are each independently selected from H, F, Cl, Br, I, OH, and $NH_2$;

$R_4$ is selected from H, $C_{1-3}$ alkyl, $C_{1-3}$ alkoxy, $C_{3-5}$ cycloalkyl, —$CH_2$-1,3-dioxolanyl, and pyrrolidinyl, wherein the $C_{1-3}$ alkyl, $C_{1-3}$ alkoxy, $C_{3-5}$ cycloalkyl, —$CH_2$-1,3-dioxolanyl, and pyrrolidinyl are optionally substituted with 1, 2 or 3 $R_b$;

L is selected from —$N(R_5)C(=O)$—, —$N(R_5)S(=O)_2$—, —$N(R_5)C(=O)N(R_6)$—, and —$NR_5$—;

$R_5$ and $R_6$ are each independently selected from H, and $C_{1-3}$ alkyl;

ring A is selected from phenyl, and pyridyl;

ring B is selected from cyclopropyl, morpholinyl, piperazinyl, tetrahydropyranyl, pyrazolyl, imidazolyl, and triazolyl;

$R_a$ and $R_b$ are each independently selected from H, F, Cl, Br, I, OH, $NH_2$, CN, $CH_3$, $N(CH_3)_2$, —$S(=O)_2CH_3$, and benzyl.

2. The compound or the pharmaceutically acceptable salt thereof as defined in claim 1, wherein $R_1$ is selected from H, $CH_3$, $CH_2CH_3$, $CH_2CH_2CH_3$,

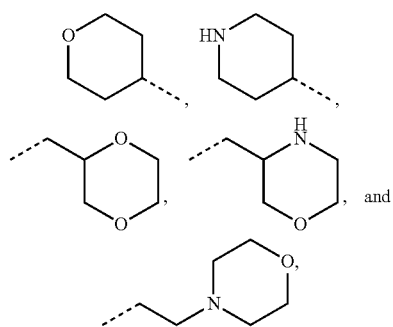

wherein the $CH_3$, $CH_2CH_3$, $CH_2CH_2CH_3$,

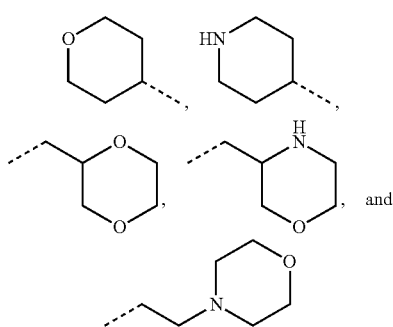

and are optionally substituted with 1, 2 or 3 $R_a$.

3. The compound or the pharmaceutically acceptable salt thereof as defined in claim 2, wherein $R_1$ is selected from H, $CH_3$, $CH_2CH_3$,

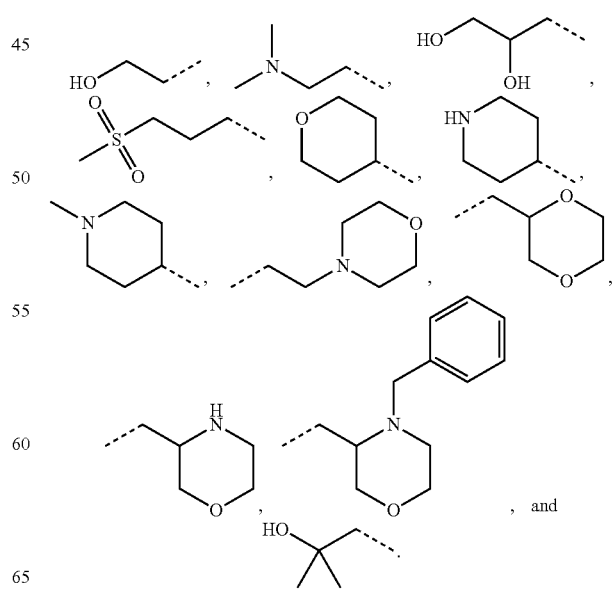

4. The compound or the pharmaceutically acceptable salt thereof as defined in claim 1, wherein $R_4$ is selected from H, cyclopropanyl, $CH_3$, $CH_2CH_3$, $CH(CH_3)_2$, $CH_2CH_2CH_3$, $OCH_3$, —$CH_2$-1,3-dioxolanyl, and pyrrolidinyl, and wherein the cyclopropanyl, $CH_3$, $CH_2CH_3$, $CH(CH_3)_2$, $CH_2CH_2CH_3$, $OCH_3$, —$CH_2$-1,3-dioxolanyl, and pyrrolidinyl are optionally substituted with 1, 2 or 3 $R_b$.

5. The compound or the pharmaceutically acceptable salt thereof as defined in claim 4, wherein $R_4$ is selected from H,

$CH_3$, $CH_2CH_3$, $CH(CH_3)_2$, $OCH_3$,

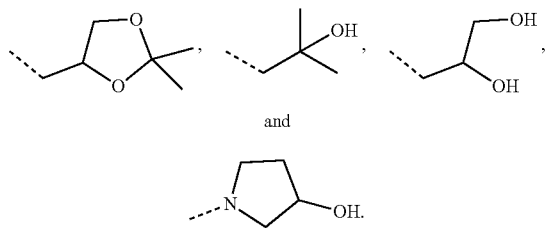

and

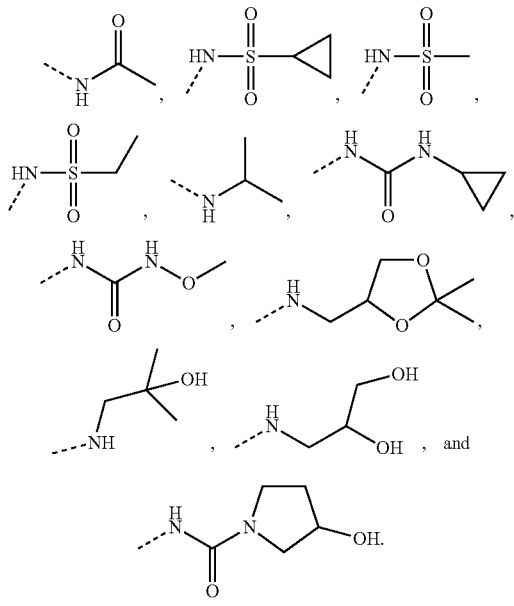

6. The compound or the pharmaceutically acceptable salt thereof as defined in claim 1, wherein $R_5$ and Re are each independently selected from H, $CH_3$, and $CH_2CH_3$.

7. The compound or the pharmaceutically acceptable salt thereof as defined in claim 6, wherein L is selected from —NHC(=O)—, —NHS(=O)$_2$—, —NHC(=O)NH—, and —NH—.

8. The compound or the pharmaceutically acceptable salt thereof as defined in claim 1, wherein -L-$R_4$ is selected from 9. The compound or the pharmaceutically acceptable salt thereof as defined in claim 1, wherein the structural unit

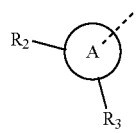

is selected from

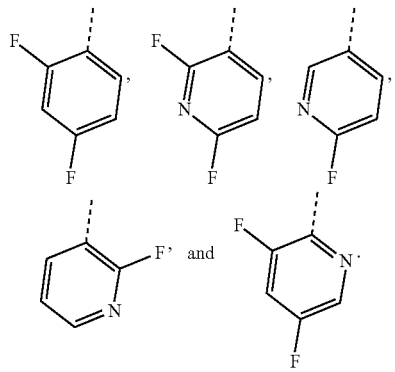

10. The compound or the pharmaceutically acceptable salt thereof as defined in claim 1, wherein ring B is selected from

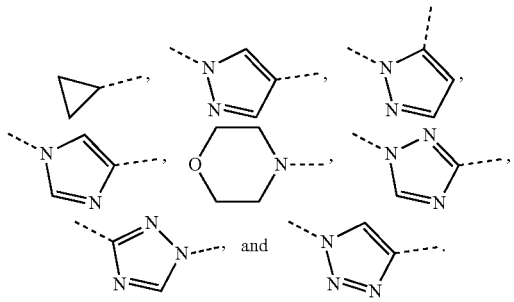

11. The compound or the pharmaceutically acceptable salt thereof as defined in claim 10, wherein the structural unit

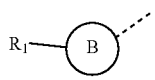

is selected from

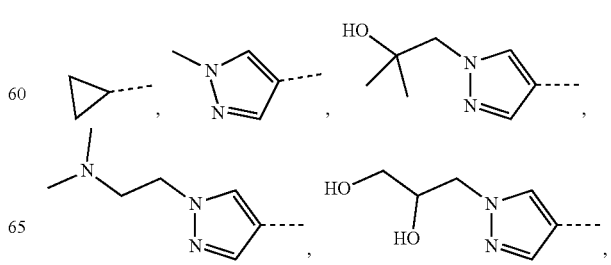

-continued
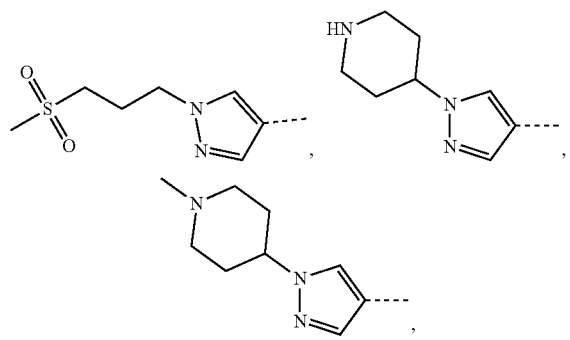
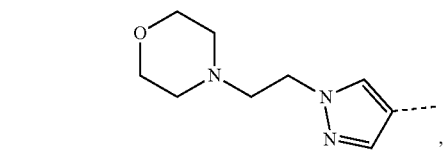
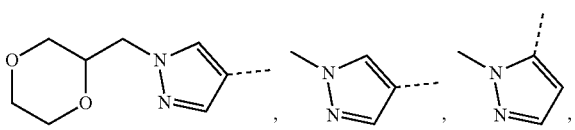
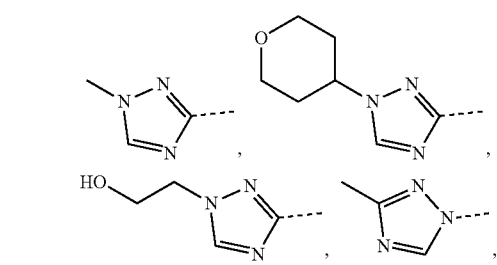
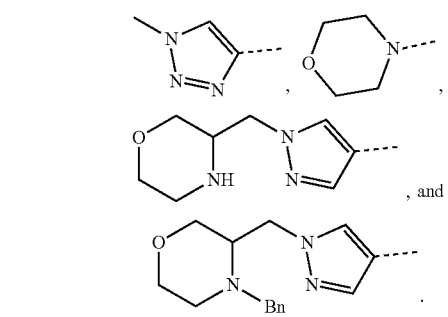
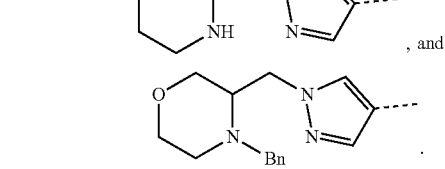
12. The compound or the pharmaceutically acceptable salt thereof as defined in claim 1, which is selected from
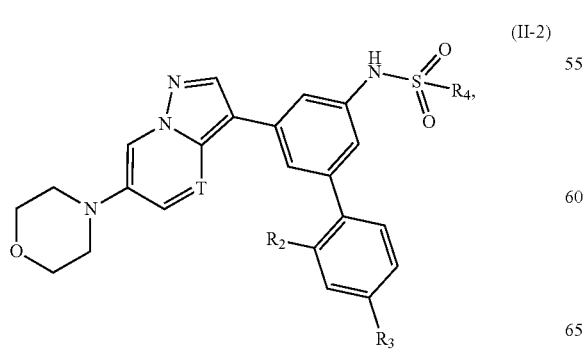
-continued
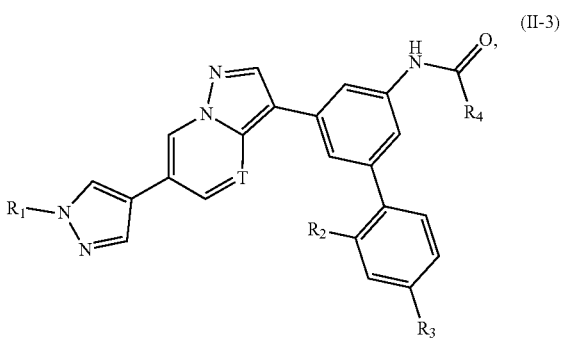
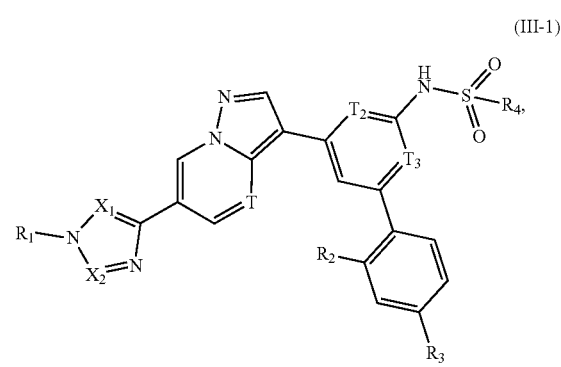
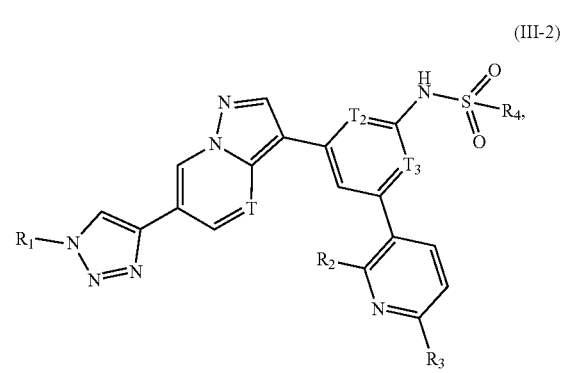
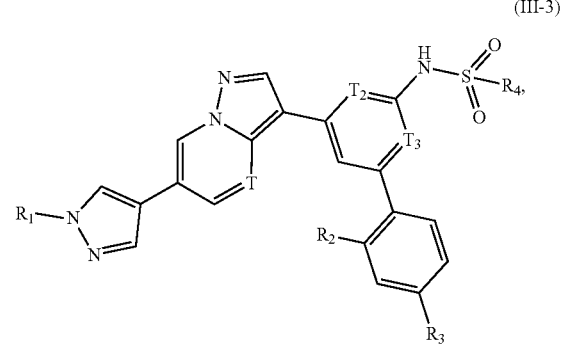

127
-continued
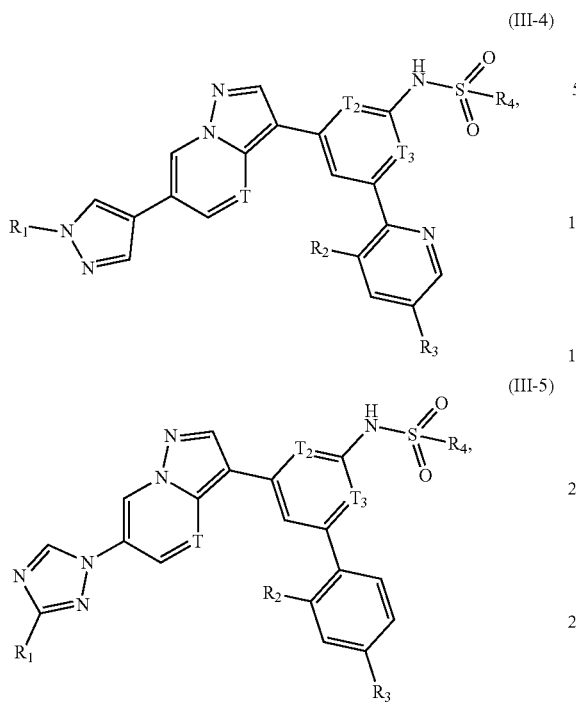
(III-4)
(III-5)
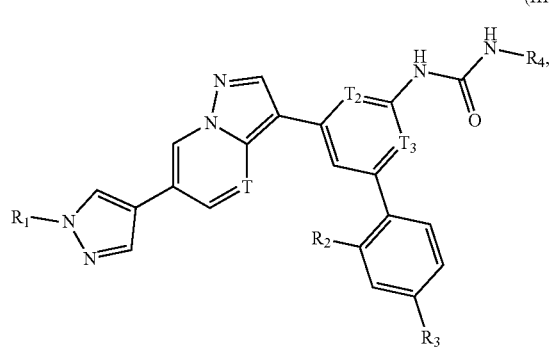
(III-6)
(III-7)
128
-continued
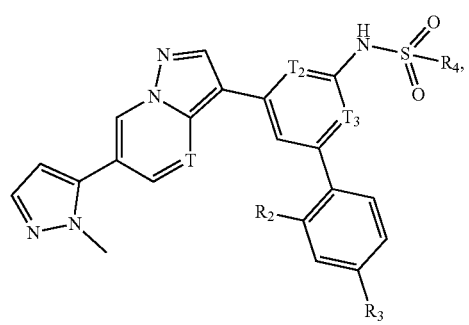
(III-8)
wherein
$X_1$ and $X_2$ are each independently selected from CH, and N, and $X_1$ and $X_2$ are not simultaneously selected from N;
and $R_1$, T, $T_2$, $T_3$, $R_2$, $R_3$, and $R_4$ are as defined in claim 1.
13. A compound or a pharmaceutically acceptable salt thereof, wherein the compound is selected from
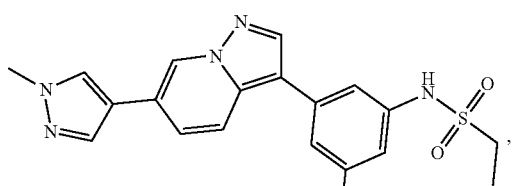
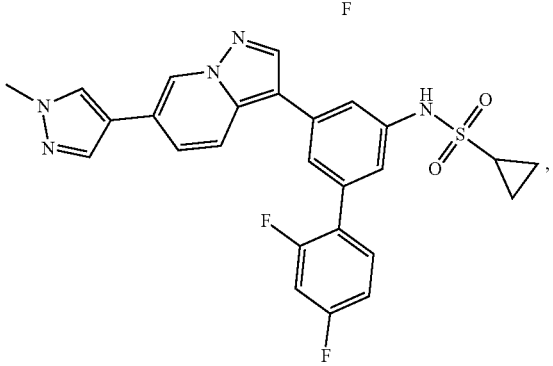
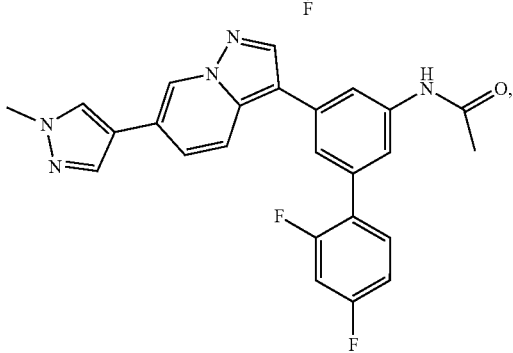

129
-continued
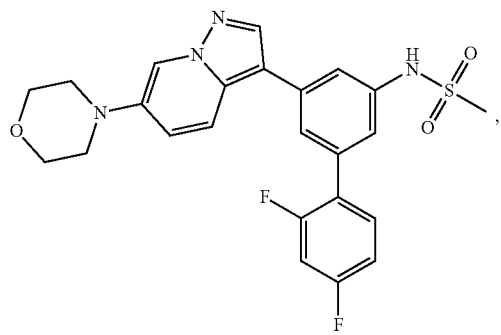
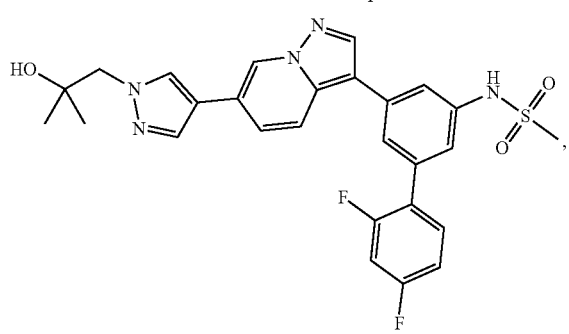
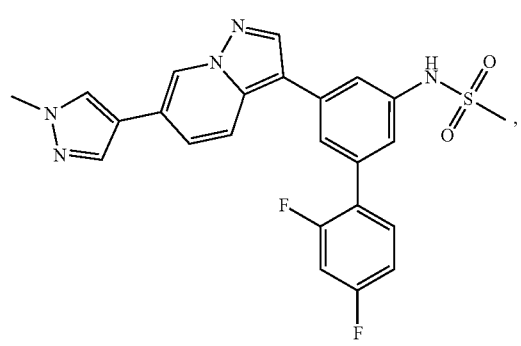
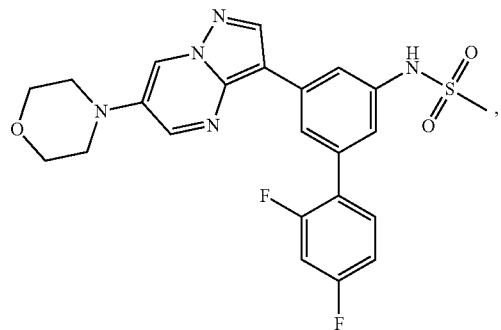
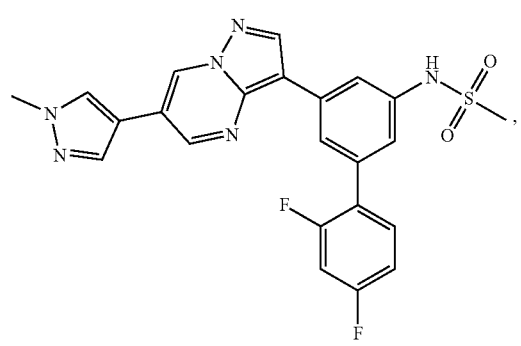
130
-continued
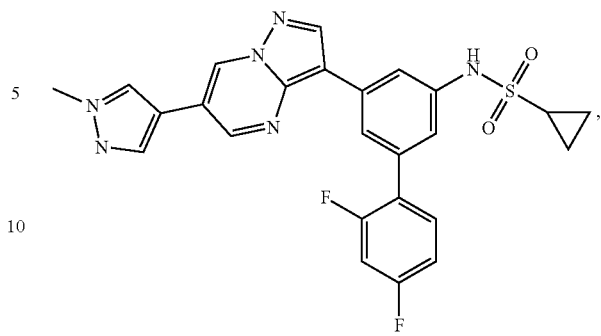
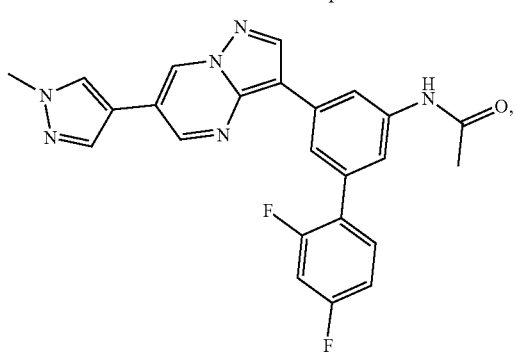
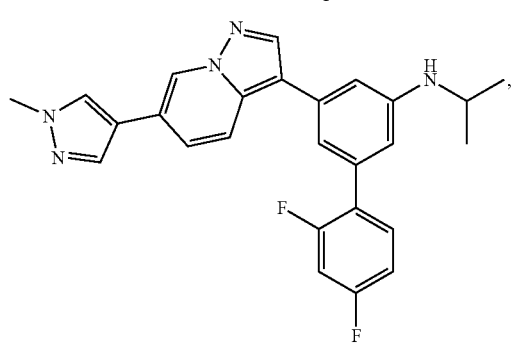
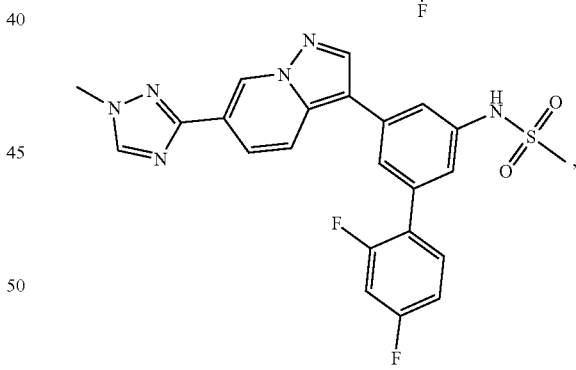
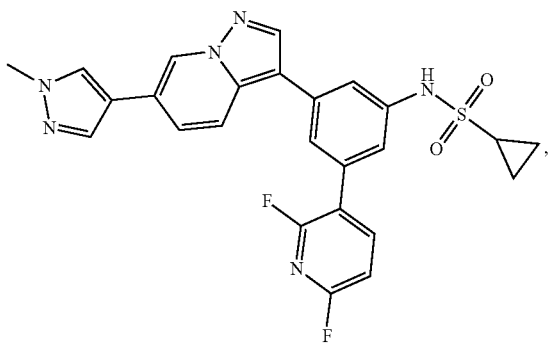

131
-continued
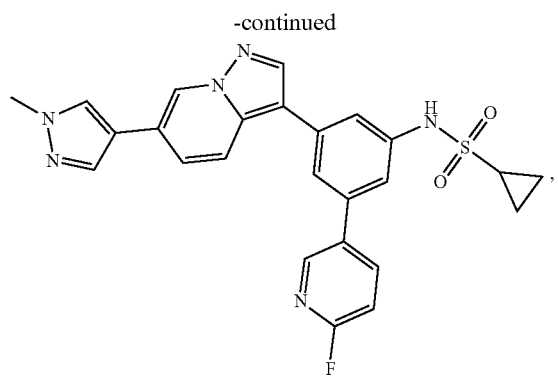
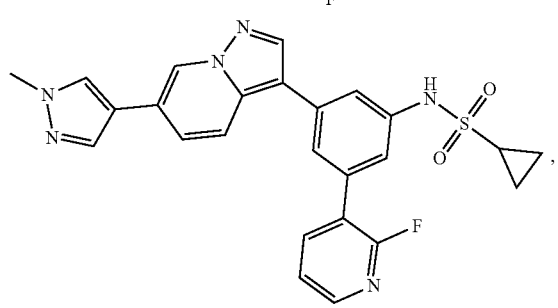
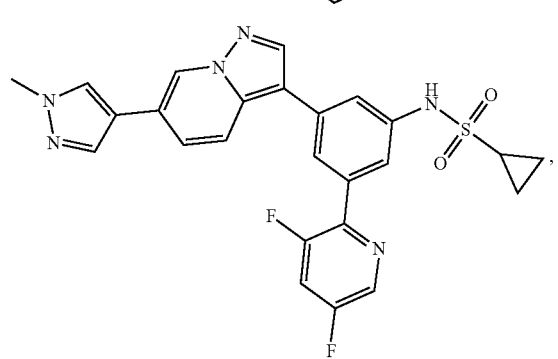
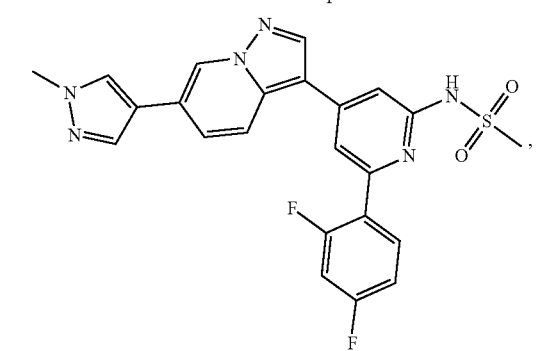
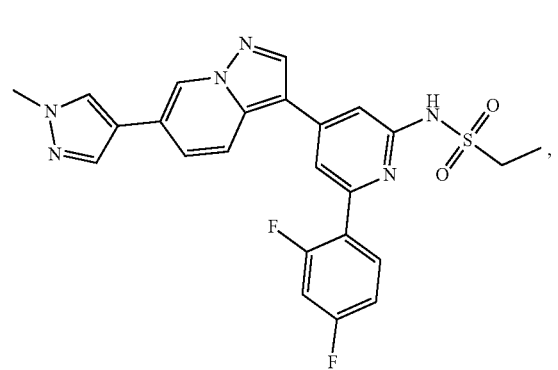
132
-continued
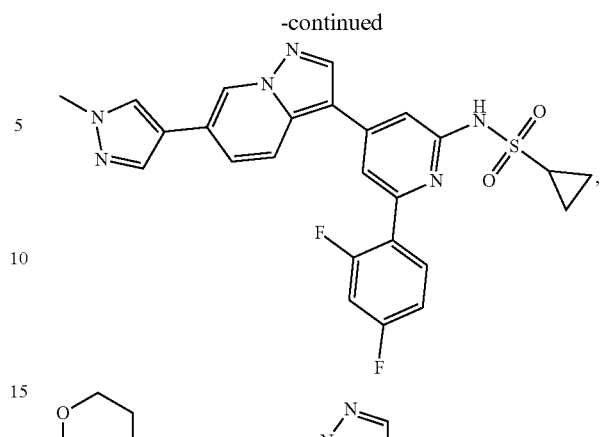
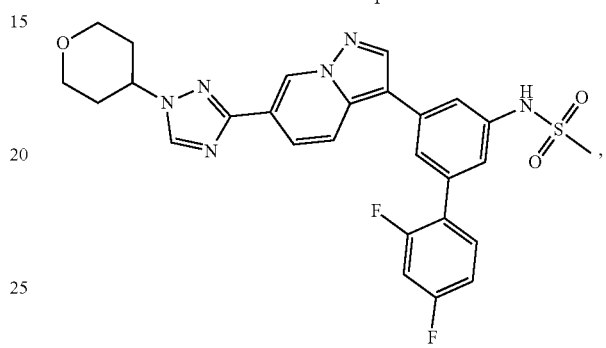
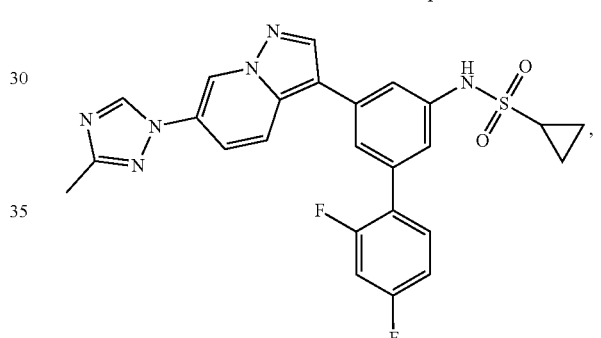
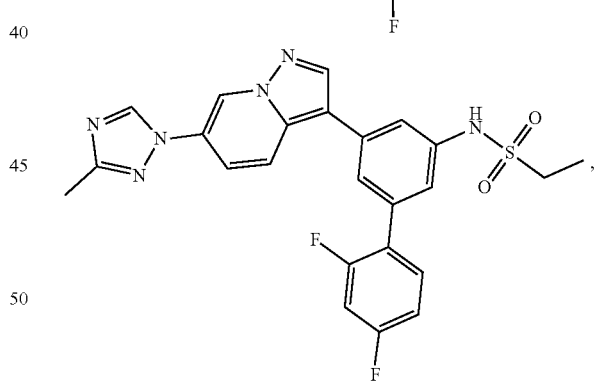
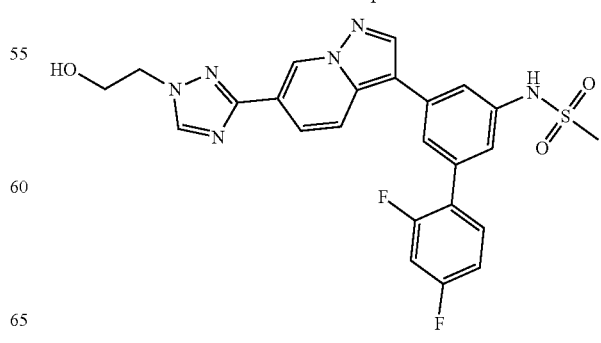

133
-continued
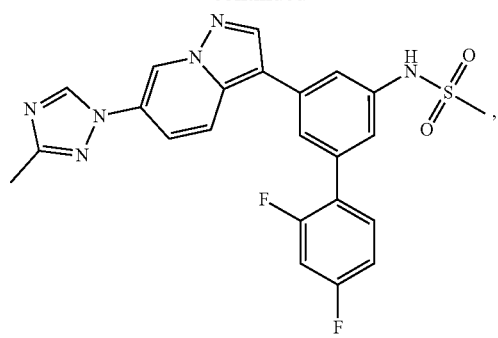
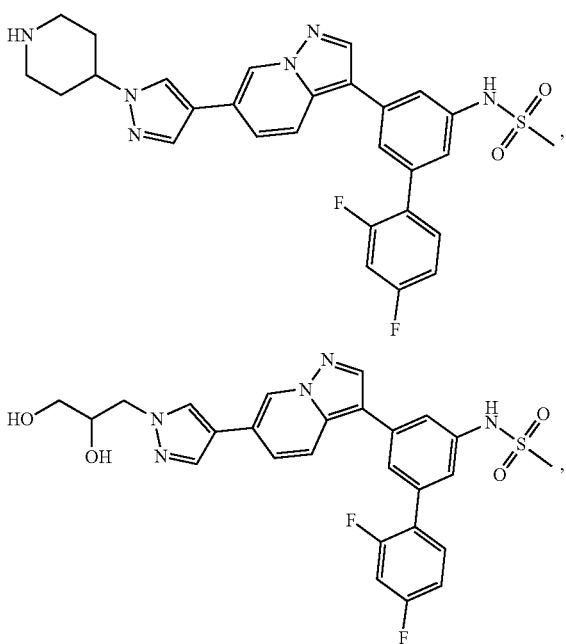
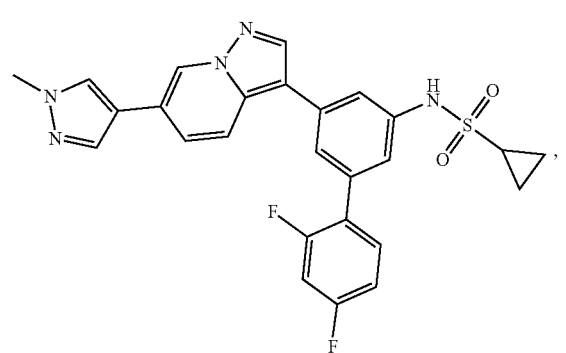
134
-continued
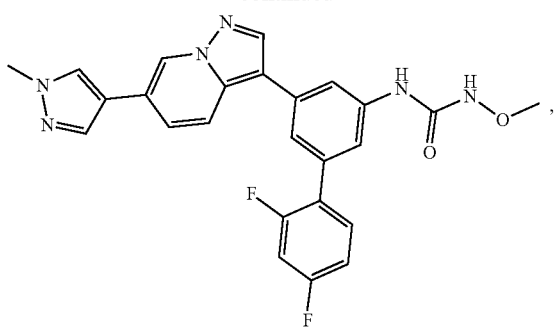
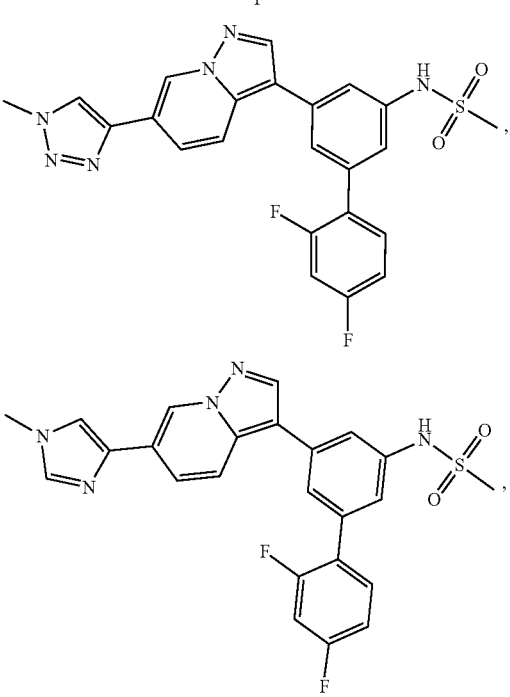
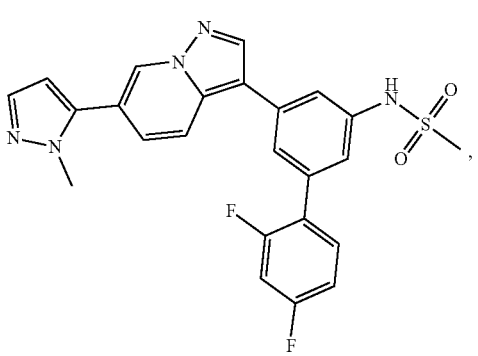

135
-continued
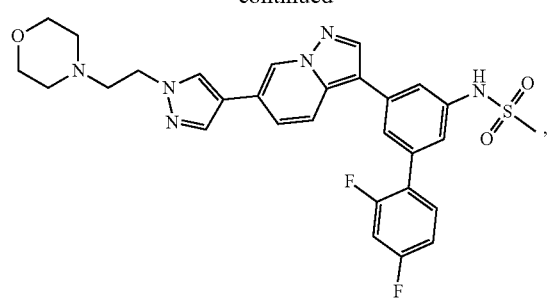
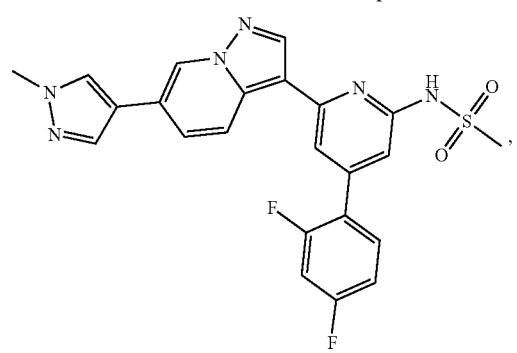
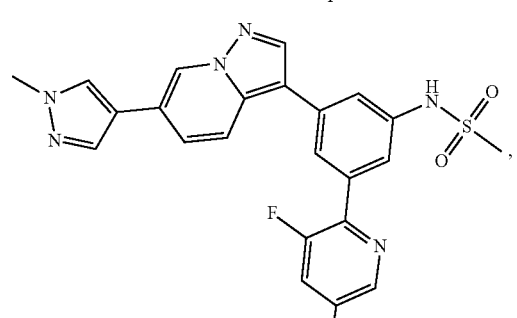
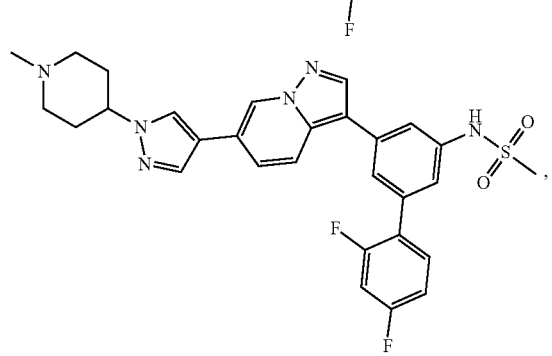
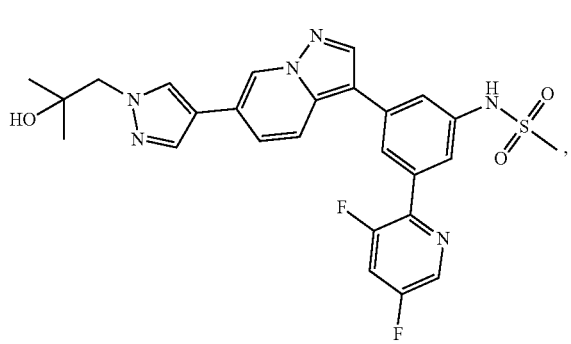
136
-continued
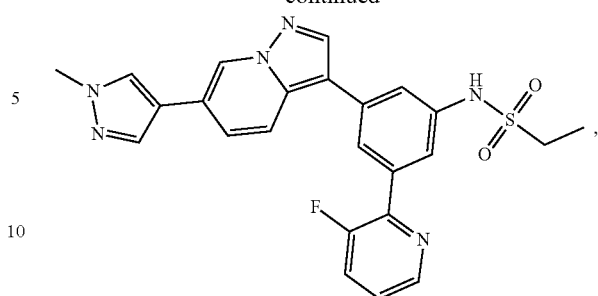
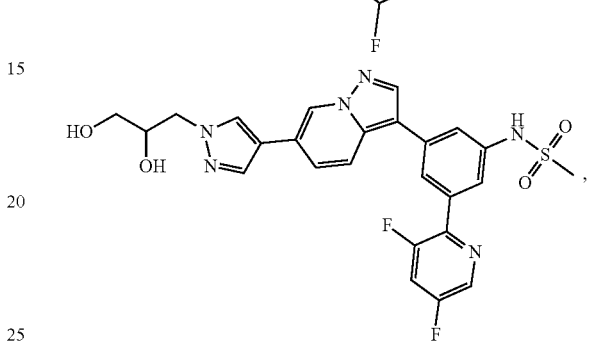
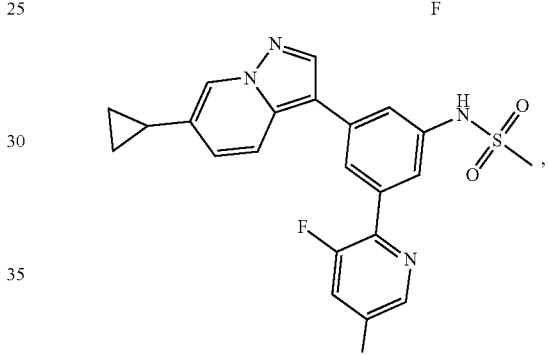
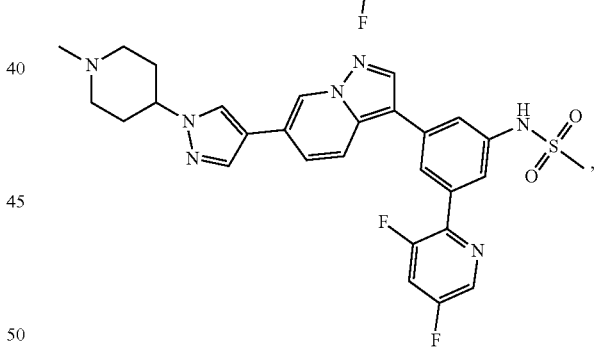
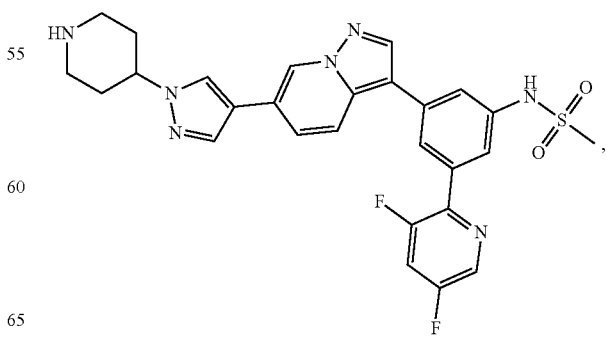

137
-continued
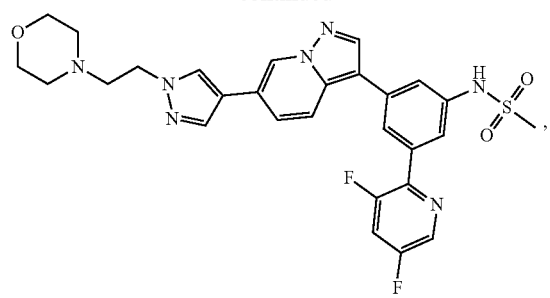
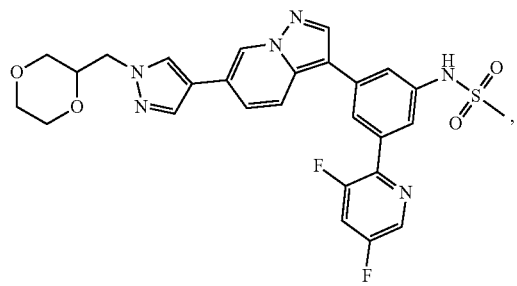
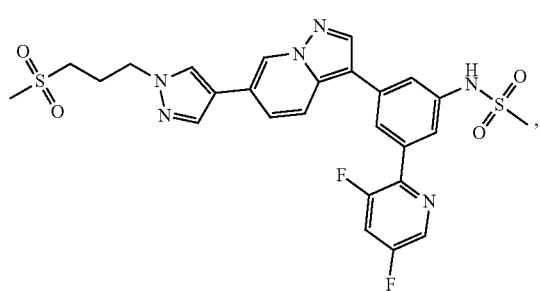
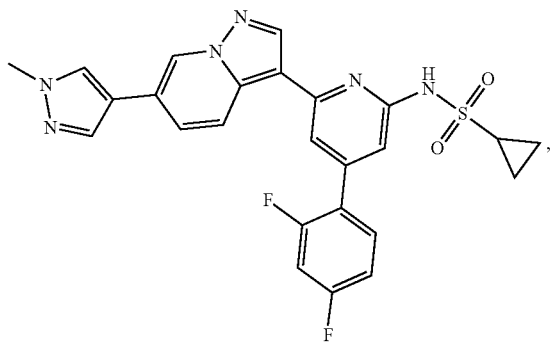
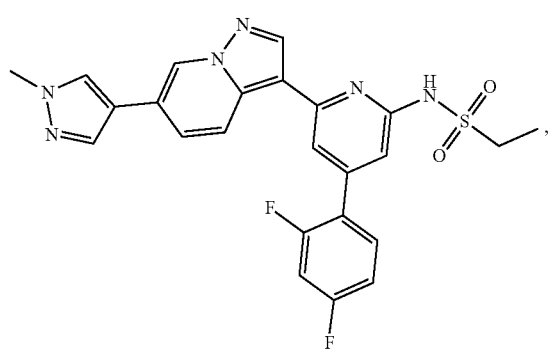
138
-continued
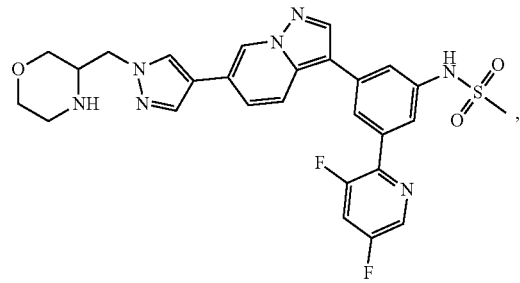
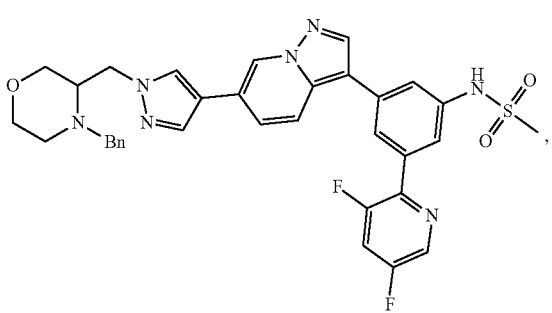
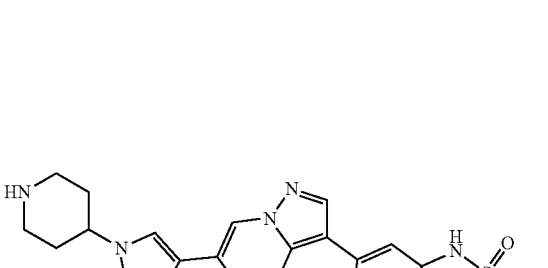
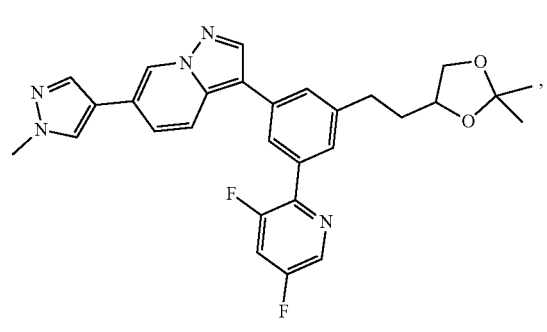

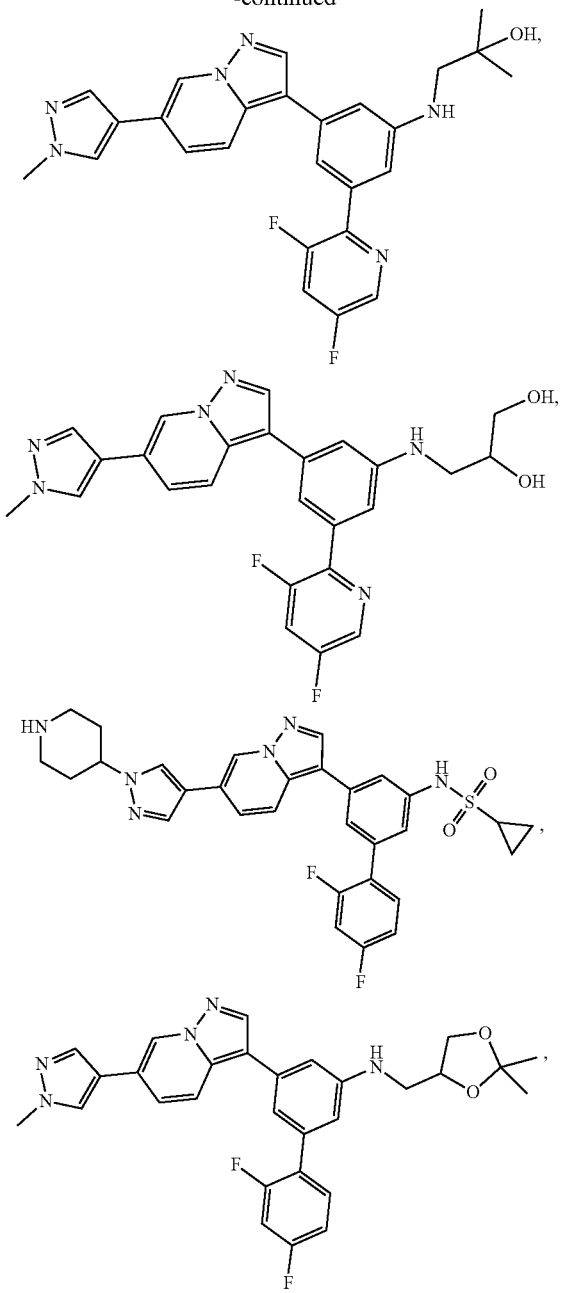

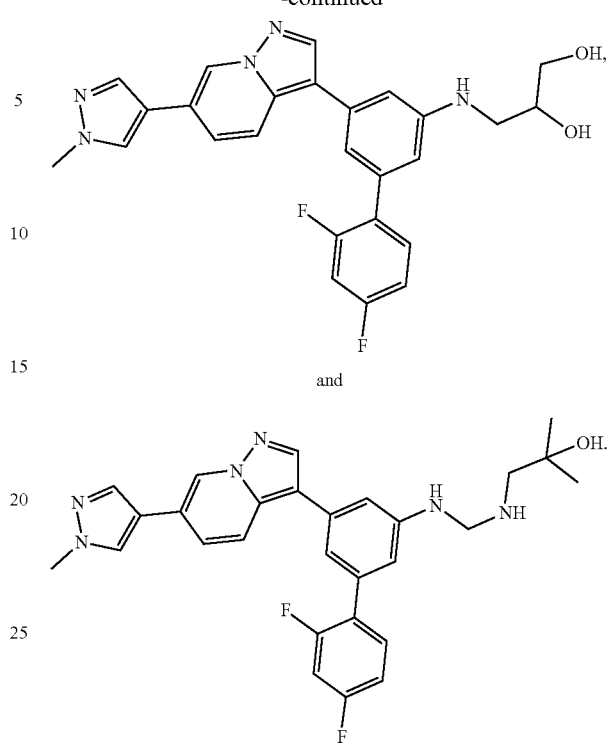

and

14. A pharmaceutical composition comprising a therapeutically effective amount of the compound or the pharmaceutically acceptable salt thereof as defined in claim 1 as an active ingredient and a pharmaceutically acceptable carrier.

15. A method for preventing or treating solid tumors in a subject in need thereof, comprising administering the compound or the pharmaceutically acceptable salt thereof as defined in claim 1.

16. A pharmaceutical composition comprising a therapeutically effective amount of the compound or the pharmaceutically acceptable salt thereof as defined in claim 13 as an active ingredient and a pharmaceutically acceptable carrier.

17. A method for preventing or treating solid tumors in a subject in need thereof, comprising administering the compound or the pharmaceutically acceptable salt thereof as defined in claim 13.

* * * * *